United States Patent
Alig et al.

(10) Patent No.: US 12,391,682 B2
(45) Date of Patent: Aug. 19, 2025

(54) ISOQUINOLINE DERIVATIVES AND THEIR USE FOR THE TREATMENT OF PARASITIC INFECTIONS

(71) Applicant: Elanco Animal Health GmbH, Monheim am Rhein (DE)

(72) Inventors: Bernd Alig, Koenigswinter (DE); Walter Huebsch, Wuppertal (DE); Nils Griebenow, Dormagen (DE); Hans-Georg Schwarz, Dorsten (DE); Wei Zhuang, Monheim am Rhein (DE); Daniel Kulke, Leverkusen (DE); Claudia Boehm, Hannover (DE); Iring Heisler, Duesseldorf (DE); Isa Jana Irina Janssen, Wiesbaden (DE); Kirsten Boerngen, Cologne (DE)

(73) Assignee: Elanco Animal Health GmbH, Monheim am Rhein (DE)

( * ) Notice: Subject to any disclaimer, the term of this patent is extended or adjusted under 35 U.S.C. 154(b) by 810 days.

(21) Appl. No.: 17/630,742

(22) PCT Filed: Jul. 27, 2020

(86) PCT No.: PCT/EP2020/071139
§ 371 (c)(1),
(2) Date: Jan. 27, 2022

(87) PCT Pub. No.: WO2021/018839
PCT Pub. Date: Feb. 4, 2021

(65) Prior Publication Data
US 2022/0274971 A1    Sep. 1, 2022

(30) Foreign Application Priority Data

Jul. 30, 2019    (EP) .................. 19189099

(51) Int. Cl.
C07D 413/14    (2006.01)
C07D 405/12    (2006.01)

(52) U.S. Cl.
CPC ......... *C07D 413/14* (2013.01); *C07D 405/12* (2013.01)

(58) Field of Classification Search
CPC ........................... C07D 413/14; C07D 405/12
See application file for complete search history.

(56) References Cited

U.S. PATENT DOCUMENTS

| | | | |
|---|---|---|---|
| 6,093,730 A | 7/2000 | Weidmann et al. | |
| 11,505,545 B2 * | 11/2022 | Hübsch ............... | C07D 215/54 |
| 2006/0217416 A1 | 9/2006 | Arend et al. | |
| 2012/0101125 A1 | 4/2012 | Mjalli et al. | |
| 2020/0024264 A1 | 1/2020 | Huebsch et al. | |
| 2020/0131175 A1 | 4/2020 | Griebenow et al. | |
| 2020/0377486 A1 | 12/2020 | Griebenow et al. | |
| 2021/0115026 A1 | 4/2021 | Huebsch et al. | |

FOREIGN PATENT DOCUMENTS

| | | |
|---|---|---|
| CN | 113474044 | 10/2021 |
| DE | 19746287 A1 | 4/1999 |
| RU | 2543374 | 2/2015 |
| RU | 2021121071 A | 1/2023 |
| RU | 2794894 C2 | 8/2023 |
| WO | 2004099206 A1 | 11/2004 |
| WO | 2004108681 A1 | 12/2004 |
| WO | 2005014533 A2 | 2/2005 |
| WO | 2007090068 A2 | 8/2007 |
| WO | 2017178416 | 10/2017 |

(Continued)

OTHER PUBLICATIONS

Guest et al. "The calcium-activated potassium channel, SLO-1, is required for the action of the novel cyclo-octadepsipeptide anthelmintic, emodepside, in Caenorhabditis elegans" International Journal for Parasitology 2007, 37, 1577-1588. (Year: 2007).*
International Search Report and Written Opinion received in international application No. PCT/EP2020/071139, mailed Oct. 28, 2020, 7 pages.
A.M. Healy et al., Pharmaceutical solvates, hydrates and amorphous forms: A special emphasis on cocrystals, Advanced Drug Delivery Reviews, 2017, vol. 117, pp. 25-46; doi: 10.1016/j.addr.2017.03.002, p. 27, right column, lines 12-14.

(Continued)

*Primary Examiner* — Joseph K McKane
*Assistant Examiner* — Jalisa Holmes Ferguson
(74) *Attorney, Agent, or Firm* — McBee Moore & Vanik IP, LLC

(57) ABSTRACT

The present invention covers new isoquinoline compounds of general formula (I):

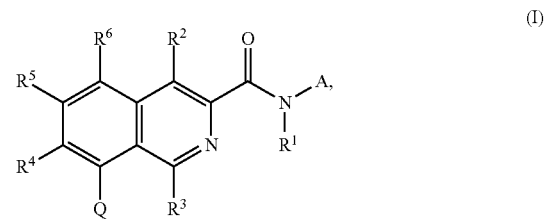

in which A, $R^1$, $R^2$, $R^3$, $R^4$, $R^5$, $R^6$, and Q are as defined herein, methods of preparing the compounds, intermediate compounds useful for preparing the compounds of formula (I), pharmaceutical compositions and combinations comprising the compounds of formula (I) and the use of the compounds of formula (I) for manufacturing pharmaceutical compositions for the treatment, control and/or prevention of diseases, in particular of helminth infections, as a sole agent or in combination with other active ingredients.

15 Claims, No Drawings

(56) References Cited

FOREIGN PATENT DOCUMENTS

| WO | 2018/087036 A1 | 5/2018 | | |
|----|----------------|--------|---|---|
| WO | 2019/002132 A1 | 1/2019 | | |
| WO | 2019/025341 A1 | 2/2019 | | |
| WO | WO-2020131629 A1 | * | 6/2020 | ......... A61K 31/4375 |

OTHER PUBLICATIONS

Z. Wojnarowska et al., On the kinetics of tautomerism in drugs: New application of broadband dielectric spectroscopy, J. Chem. Phys., 2010, vol. 133, 094507, DOI: 10.1063/1.3475688; p. 094507-7, Fig. 5, right column, section D.

L.B. Kier and L.H. Hall, Bioisosterism: Quantitation of Structure and Property Effects, Chemistry & Biodiversity, 2004, vol. 1, pp. 138-151.

Jiang et al., "1-(Phenyl)isoquinoline-3-carboxamides as a novel class of subtype selective inhibitors of thyrotropin-releasing hormone (TRH) receptors," Bioorganic & Medicinal Chemistry Letters 2005, 15(3), pp. 733-736.

Knunyants, IL, et al., Chemical Encyclopedic Dictionary, Soviet Encyclopedia, Moscow, pp. 130-131, 559-560 (1983).

Belikov, VG, et al., "The relationship between the chemical structure, properties of substances and their effect on the body", Pharmaceutical Chemistry, Chapter 2.6, MEDpressinform, Moscow, pp. 27-29 (2007).

Mashkovsky, MD, et al., Medicinal Products, Moscow, OOO Novaya Volna, Publisher S.B. Divov, vol. 1, p. 11 (2001).

* cited by examiner

ISOQUINOLINE DERIVATIVES AND THEIR USE FOR THE TREATMENT OF PARASITIC INFECTIONS

CROSS-REFERENCE TO RELATED APPLICATIONS

This application is the National Stage entry of International Application No. PCT/EP2020/071139, filed 27 Jul. 2020, which claims priority to European Patent Application No. 19189099.5, filed 30 Jul. 2019.

BACKGROUND

Field

The present invention covers new isoquinoline derivatives of general formula (I) as described and defined herein, methods of preparing said compounds, intermediate compounds useful for preparing said compounds, pharmaceutical compositions and combinations comprising said compounds, and the use of said compounds for manufacturing pharmaceutical compositions for the control, treatment and/or prevention of diseases, in particular for the control, treatment and/or prevention of infections with helminths, more particularly of infections with gastro-intestinal and extra-intestinal nematodes, in animals and humans, formulations containing such compounds and methods for the control, treatment and/or prevention of infections with helminths, more particularly of infections with gastro-intestinal and extra-intestinal nematodes, in animals and humans as a sole agent or in combination with other active ingredients.

Description of Related Art

The occurrence of resistances against all commercial anthelmintics seems to be a growing problem in the area of veterinary medicine. The extensive utilisation of anthelmintics to manage the control of nematodes resulted in significant selection of highly resistant worm populations. Therefore, the spread of resistance against all anthelmintic drug classes threatens effective worm control in cattle, goats, sheep and horses. Furthermore, successful prevention of heartworm disease in dogs, which currently solely relies on the utilisation of macrocyclic lactones, is in danger as loss of efficacy for multiple macrocyclic lactones has been described for some regions of the United States of America—especially in those areas where the heartworm challenge for infection is high. Finally, experimental infection studies with *Dirofilaria immitis* larvae from suspected field loss of efficacy cases in the Lower Mississippi Delta provided in vivo confirmation of the existence of macrocyclic lactone resistance.

Although resistance of human helminths against anthelmintics seems currently to be rare, the spread of anthelmintic resistance in the veterinary field as mentioned before needs to be considered in the treatment of human helminthosis as well. Persistent underdosed treatments against filariosis may lead to highly resistant genotypes and resistances have already been described for certain anthelmintics (e.g. praziquantel, benzimidazole and niclosamide).

Therefore, resistance-breaking anthelmintics with new molecular modes of action are urgently required.

It is an object of the present invention to provide compounds which can be used as anthelmintics in the medical, especially veterinary, field with a satisfactory or improved anthelmintic activity against a broad spectrum of helminths, particularly at relatively low dosages, for the control, treatment and/or prevention of infections with helminths in animals and humans, preferably without any adverse toxic effects to the treated organism.

Certain isoquinoline-3-carboxamides are described in DE 19746287/U.S. Pat. No. 6,093,730 as prolyl-4-hydroxylase inhibitors.

Bioorganic & Medicinal Chemistry Letters 2005, 15(3), 733-736 describes 1-(Phenyl)isoquinoline-3-carboxamides as a novel class of subtype selective inhibitors of thyrotropin-releasing hormone (TRH) receptors.

WO 2004099206 claims isoquinoline-3-carboxamides as α7 nicotinic acetylcholine receptor agonists.

WO 2004108681 describes the use of isoquinoline-3-carboxamides in mediating hypoxia inducible factor and increasing endogenous erythropoietin.

WO 2005014533 claims isoquinoline-3-carboxamides as antagonists of factor IX and/or factor XI.

WO 2007090068 claims cyanoisoquinoline-3-carboxamides stabilizing hypoxia inducible factor.

US 20060217416 claims isoquinoline-3-carboxamides suitable for use in mediating hypoxia inducible factor and for treating erythropoietin-associated conditions.

US 20120101125 relates to substituted isoquinoline-3-carboxamides useful as inhibitors of $-secretase.

WO2018087036 describes quinoline-3-carboxamides and their use as anthelmintics in the medical especially veterinary field.

However, the state of the art does not describe the new isoquinoline derivatives of general formula (I) of the present invention as described and defined herein.

It has now been found, and this constitutes the basis of the present invention, that the compounds of the present invention have surprising and advantageous properties.

In particular, the compounds of the present invention have surprisingly been found to effectively interact with Slo-1 calcium-gated potassium channels of nematodes. This interaction is characterised by achieving paralysis/inhibition in particular of gastro-intestinal nematodes, of free-living nematodes, and of filariae, for which data are given in the biological experimental section. Therefore the compounds of the present invention may be used as anthelmintics for the control, treatment and/or prevention of gastro-intestinal and extra-intestinal helminth infections, in particular gastro-intestinal and extra-intestinal infections with nematodes, including filariae. The new compounds of the present invention further exhibit high stability and are thus advantageous compared to other compounds known from the prior art.

SUMMARY

In accordance with a first aspect, the present invention covers compounds of general formula (I):

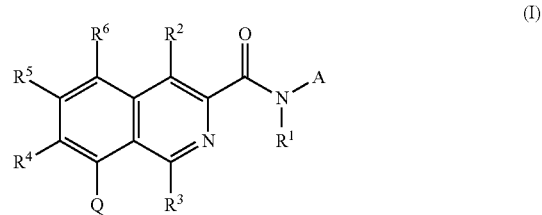

in which:

A is A1 or A2,

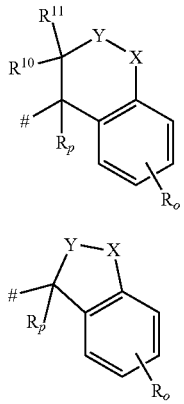

A1

A2 o is 0, 1, 2, 3 or 4,

R is selected from the group consisting of hydrogen, halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl, —S(O)—$C_1$-$C_4$-halogenoalkyl and —$SO_2$-$C_1$-$C_4$-halogenoalkyl having 1 to 5 halogen atoms, $R_p$ is selected from the group consisting of hydrogen, $C_1$-$C_4$-alkyl, X, Y are independently selected from the group consisting of $CR^7R^8$, O, S, and N—$R^9$, wherein at least one of X and Y is $CR^7R^8$, or X, Y form together a ring member selected from the group consisting of —C(O)—O—, —C(O)—$NR^9$—, —S(O)—$NR^9$—, —$SO_2$—$NR^9$— and —$SO_2$—O—, $R^1$ is selected from the group consisting of hydrogen, cyano, —CHO, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, $C_3$-$C_6$-halogenocycloalkyl having 1 to 5 halogen atoms, $C_3$-$C_4$-alkenyl, $C_3$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, —NH—$C_1$-$C_4$-alkyl, —N($C_1$-$C_4$-alkyl)$_2$, $NH_2$-$C_1$-$C_4$-alkyl-, $C_1$-$C_4$-alkyl-NH—$C_1$-$C_4$-alkyl-, ($C_1$-$C_4$-alkyl)$_2$N—$C_1$-$C_4$-alkyl-, $C_1$-$C_4$-alkyl-C(O)—, $C_1$-$C_4$-halogenoalkyl-C(O)— having 1 to 5 halogen atoms, $C_1$-$C_4$-alkoxy-C(O)—, benzyloxy-C(O)—, $C_1$-$C_4$-alkoxy-$C_1$-$C_4$-alkyl-C(O)—, —$SO_2$—$C_1$-$C_4$-alkyl, and —$SO_2$—$C_1$-$C_4$-halogenoalkyl having 1 to 5 halogen atoms;

phenyl-$C_1$-$C_4$-alkyl, optionally substituted by 1, 2, 3, 4 or 5 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^2$ is selected from the group consisting of
hydrogen, halogen, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$;

—$NR^{12}R^{13}$;

—$OR^{14}$;

—$SR^{15}$, —S(O)$R^{15}$, —$SO_2R^{15}$;

$C_1$-$C_6$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted by 1, 2, 3, 4 or 5 substituents independently selected from the group consisting of halogen, —OH, —$NO_2$, cyano, $C_1$-$C_4$-alkyl-C(O)—, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, —$NH_2$, —NH($C_1$-$C_4$-alkyl), —N($C_1$-$C_4$-alkyl)$_2$, —NH(C(O)—$C_1$-$C_4$-alkyl), —N($C_1$-$C_4$-alkyl)(C(O)—$C_1$-$C_4$-alkyl), —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$-$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, heterospirocycloalkyl, 5-membered heteroaryl and 6-membered heteroaryl, each of which is optionally substituted by 1, 2, 3 or 4 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-alkyl-C(O)—, $C_1$-$C_4$-halogenoalkyl having 1 to 5 halogen atoms, $C_1$-$C_4$-alkoxy, hydroxy-$C_1$-$C_4$-alkyl, $C_1$-$C_4$-alkoxy-$C_1$-$C_4$-alkyl-, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms, and 4- to 10-membered heterocycloalkyl, $R^3$ is hydrogen or $C_1$-$C_4$-alkyl, $R^4$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-halogenoalkoxy having 1 to 5 halogen atoms, $C_1$-$C_4$-alkyl-C(O)—, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, preferably hydrogen and halogen, more preferably fluorine and chlorine, $R^5$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-halogenoalkoxy having 1 to 5 halogen atoms, $C_1$-$C_4$-alkyl-C(O)—, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, $R^6$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-halogenoalkoxy having 1 to 5 halogen atoms, $C_1$-$C_4$-alkyl-C(O)—, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, $R^7$ is selected from the group consisting of hydrogen, —OH, fluorine, $C_1$-$C_4$-alkyl and $C_1$-$C_4$-alkoxy, $R^8$ is selected from the group consisting of hydrogen, —OH, fluorine, $C_1$-$C_4$-alkyl and $C_1$-$C_4$-alkoxy, or $R^7$ and $R^8$ together form an oxo group (=O), or $R^7$ and $R^8$ form, together with the carbon atom to which they are attached, a 3- to 6-membered ring selected from the group consisting of $C_3$-$C_6$-cycloalkyl and 3- to 6-membered heterocycloalkyl, $R^9$ is selected from the group consisting of hydrogen, $C_1$-$C_4$-alkyl, $C_1$-$C_4$-halogenoalkyl having 1 to 5 halogen atoms and $C_1$-$C_4$-alkoxy, $R^{10}$ is selected from the group consisting of hydrogen, —OH, $C_1$-$C_4$-alkyl and $C_1$-$C_4$-alkoxy, $R^{11}$ is selected from the group consisting of hydrogen, $C_1$-$C_4$-alkyl and $C_1$-$C_4$-alkoxy, or $R^{10}$ and $R^{11}$ form, together with the carbon atom to which they are attached, a 3- to 6-membered ring selected from the group consisting of $C_3$-$C_6$-cycloalkyl and 3- to 6-membered heterocycloalkyl, $R^{12}$ and $R^{13}$ are independently selected from the group consisting of
hydrogen, —OH, —$NH_2$, —NH($C_1$-$C_4$-alkyl), —N($C_1$-$C_4$-alkyl)$_2$, —NH(—C(O)—$C_1$-$C_4$-alkyl), —N($C_1$-$C_4$-alkyl)(-C(O)—$C_1$-$C_4$-alkyl), $C_1$-$C_4$-alkoxy, $C_1$-$C_4$-alkoxy-C(O)—;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, —NH—C(O)—$C_1$-$C_4$-alkyl, —N($C_1$-$C_4$-alkyl)(-C(O)—$C_1$-$C_4$-alkyl), $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms and ($C_1$-$C_4$-alkoxy)$_2$P(=O)—;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, benzo-$C_5$-$C_6$-cycloalkyl, each of which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

a monocyclic or a bicyclic heterocycle selected from the group of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH (C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$-C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms, $R^{14}$ is selected from the group consisting of
—NH$_2$, —NH(C$_1$-C$_4$-alkyl), —N(C$_1$-C$_4$-alkyl)$_2$;

C$_1$-C$_4$-alkyl, C$_3$-C$_6$-cycloalkyl, phenyl-C$_1$-C$_4$-alkyl, each of which is optionally substituted by 1, 2 or 3 substituents independently selected from the group consisting of halogen, —OH, cyano, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms;

heterocyclyl-C$_1$-C$_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, C$_1$-C$_4$-alkyl, C$_1$-C$_4$-halogenoalkyl having 1 to 5 halogen atoms, C$_1$-C$_4$-alkoxy, hydroxy-C$_1$-C$_4$-alkyl, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms;

phenyl, which is optionally substituted by 1, 2 or 3 substituents independently selected from the group consisting of halogen, cyano, nitro, —OH, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$-C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms; and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, C$_1$-C$_4$-alkyl, C$_1$-C$_4$-halogenoalkyl having 1 to 5 halogen atoms, C$_1$-C$_4$-alkoxy, hydroxy-C$_1$-C$_4$-alkyl, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-

C$_4$-alkyl)$_2$, —S—C$_1$-C$_4$-alkyl, —S(O)—C$_1$-C$_4$-alkyl, —SO$_2$-C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms, $R^{15}$ is selected from the group consisting of
hydrogen;

C$_1$-C$_4$-alkyl, C$_3$-C$_6$-cycloalkyl, phenyl-C$_1$-C$_4$-alkyl, each of which is optionally substituted by 1, 2 or 3 substituents independently selected from the group consisting of halogen, —OH, cyano, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms;

heterocyclyl-C$_1$-C$_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, C$_1$-C$_4$-alkyl, C$_1$-C$_4$-halogenoalkyl having 1 to 5 halogen atoms, C$_1$-C$_4$-alkoxy, hydroxy-C$_1$-C$_4$-alkyl, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms;

phenyl, which is optionally substituted by 1, 2 or 3 substituents independently selected from the group consisting of halogen, cyano, nitro, —OH, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$-C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms; and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, C$_1$-C$_4$-alkyl, C$_1$-C$_4$-halogenoalkyl having 1 to 5 halogen atoms, C$_1$-C$_4$-alkoxy, hydroxy-C$_1$-C$_4$-alkyl, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-

$C_4$-alkyl)$_2$, —S—$C_1$-$C_4$-alkyl, —S(O)—$C_1$-$C_4$-alkyl, —SO$_2$-$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —SO$_2$—$C_1$-$C_4$-halogenoalkyl having 1 to 5 halogen atoms, Q is selected from the group consisting of 6- or 10-membered aryl and 5- to 10-membered heteroaryl, each of which is optionally substituted by 1, 2, 3, 4 or 5 substituents selected from the group consisting of halogen, SF$_5$, cyano, —CHO, nitro, oxo, $C_1$-$C_4$-alkyl, $C_1$-$C_4$-hydroxyalkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH—SO$_2$—($C_1$-$C_4$-alkyl), —N(SO$_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocyclyl, which is optionally substituted with 1 or 2 substituents selected from the group consisting of fluorine, chlorine, bromine, methyl and cyano, —CH$_2$—O—($C_1$-$C_4$-alkyl), —CH$_2$—NH($C_1$-$C_4$-alkyl), —CH$_2$—N($C_1$-$C_4$-alkyl)$_2$, methyl substituted with a 4- to 6-membered heterocyclyl which itself is optionally substituted with 1 or 2 substituents selected from the group consisting of fluorine, chlorine, bromine, methyl and cyano, —CH$_2$—S—($C_1$-$C_4$-alkyl), —CH$_2$—S(O)—($C_1$-$C_4$-alkyl), —CH$_2$—SO$_2$—($C_1$-$C_4$-alkyl), —S—($C_1$-$C_4$-alkyl), —S(O)—($C_1$-$C_4$-alkyl), —SO$_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —SO$_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), —NHCO($C_1$-$C_4$-halogenoalkyl) having 1 to 5 halogen atoms, wherein when Y is O, S or N—$R^9$, none of $R^7$, $R^8$, $R^{10}$ and $R^{11}$ is —OH or $C_1$-$C_4$-alkoxy, and wherein when X is O, S or N—$R^9$, none of $R^7$ and $R^8$ is —OH or $C_1$-$C_4$-alkoxy;

and stereoisomers, tautomers, N-oxides, hydrates, solvates, and salts thereof, and mixtures of same.

DETAILED DESCRIPTION OF A PREFERRED EMBODIMENT

Definitions

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon or nitrogen atom. Commonly, it is possible for the number of optional substituents, when present, to be 1, 2, 3, 4 or 5, in particular 1, 2 or 3.

As used herein, the term "one or more", e.g. in the definition of the substituents of the compounds of general formula (I) of the present invention, means "1, 2, 3, 4 or 5, particularly 1, 2, 3 or 4, more particularly 1, 2 or 3, even more particularly 1 or 2".

As used herein, an oxo substituent represents an oxygen atom, which is bound to a carbon atom or to a sulfur atom via a double bond.

The term "ring substituent" means a substituent attached to an aromatic or nonaromatic ring which replaces an available hydrogen atom on the ring.

Should a composite substituent be composed of more than one parts, e.g. ($C_1$-$C_4$-alkoxy)-($C_1$-$C_4$-alkyl)-, it is possible for the position of a given part to be at any suitable position of said composite substituent, i.e. the $C_1$-$C_4$-alkoxy part can be attached to any carbon atom of the $C_1$-$C_4$-alkyl part of said ($C_1$-$C_4$-alkoxy)-($C_1$-$C_4$-alkyl)-group. A hyphen at the beginning or at the end of such a composite substituent indicates the point of attachment of said composite substituent to the rest of the molecule. Should a ring, comprising carbon atoms and optionally one or more heteroatoms, such as nitrogen, oxygen or sulfur atoms for example, be substituted with a substituent, it is possible for said substituent to be bound at any suitable position of said ring, be it bound to a suitable carbon atom and/or to a suitable heteroatom.

As used herein, the position via which a respective substituent is connected to the rest of the molecule may in a drawn structure be depicted by a hash sign (#) or a dashed line in said substituent.

The term "comprising" when used in the specification includes "consisting of".

If within the present text any item is referred to as "as mentioned herein", it means that it may be mentioned anywhere in the present text.

The terms as mentioned in the present text have the following meanings:

The term "halogen atom" means a fluorine, chlorine, bromine or iodine atom, particularly a fluorine, chlorine or bromine atom, more preferably fluorine or chlorine.

The term "$C_1$-$C_6$-alkyl" means a linear or branched, saturated, monovalent hydrocarbon group having 1, 2, 3, 4, 5 or 6 carbon atoms. The term "$C_1$-$C_4$-alkyl" means a linear or branched, saturated, monovalent hydrocarbon group having 1, 2, 3, or 4 carbon atoms, e.g. a methyl, ethyl, n-propyl, isopropyl, n-butyl, sec-butyl, isobutyl or a tert-butyl group, or an isomer thereof. Particularly, said group has 1, 2 or 3 carbon atoms ("$C_1$-$C_3$-alkyl"), e.g. a methyl, ethyl, n-propyl or isopropyl group. Also a tert-butyl group is preferred.

The term "$C_1$-$C_4$-hydroxyalkyl" means a linear or branched, saturated, monovalent hydrocarbon group in which the term "$C_1$-$C_4$-alkyl" is defined supra, and in which 1 or 2 hydrogen atoms are replaced with a hydroxy group, e.g. a hydroxymethyl, 1-hydroxyethyl, 2-hydroxyethyl, 1,2-dihydroxyethyl, 3-hydroxypropyl, 2-hydroxypropyl, 1-hydroxypropyl, 1-hydroxypropan-2-yl, 2-hydroxypropan-2-yl, 2,3-dihydroxypropyl, 1,3-dihydroxypropan-2-yl, 3-hydroxy-2-methyl-propyl, 2-hydroxy-2-methyl-propyl, 1-hydroxy-2-methyl-propyl group.

The term "—NH($C_1$-$C_4$-alkyl)" or "—N($C_1$-$C_4$-alkyl)$_2$" means a linear or branched, saturated, monovalent group in which the term "$C_1$-$C_4$-alkyl" is as defined supra, e.g. a methylamino, ethylamino, n-propylamino, isopropylamino, N,N-dimethylamino, N-methyl-N-ethylamino or N,N-diethylamino group.

The term "—S—$C_1$-$C_4$-alkyl", "—S(O)—$C_1$-$C_4$-alkyl" or "—SO$_2$—$C_1$-$C_4$-alkyl" means a linear or branched, saturated group in which the term "$C_1$-$C_4$-alkyl" is as defined supra, e.g. a methylsulfanyl, ethylsulfanyl, n-propylsulfanyl, isopropylsulfanyl, n-butylsulfanyl, sec-butylsulfanyl, isobutylsulfanyl or tert-butylsulfanyl group, a methylsulfinyl, ethylsulfinyl, n-propylsulfinyl, isopropylsulfinyl, n-butylsulfinyl, sec-butylsulfinyl, isobutylsulfinyl or tert-butylsulfinyl group, or a methylsulfonyl, ethylsulfonyl, n-propylsulfonyl, isopropylsulfonyl, n-butylsulfonyl, sec-butylsulfonyl, isobutylsulfonyl or tert-butylsulfonyl group.

The term "$C_1$-$C_4$-halogenoalkyl" means a linear or branched, saturated, monovalent hydrocarbon group in which the term "$C_1$-$C_4$-alkyl" is as defined supra, and in which one or more of the hydrogen atoms are replaced, identically or differently, with a halogen atom. Particularly, said halogen atom is a fluorine atom. More particularly, all said halogen atoms are fluorine atoms ("$C_1$-$C_4$-fluoroalkyl"). Said $C_1$-$C_4$-halogenoalkyl group is, for example, fluoromethyl, difluoromethyl, trifluoromethyl, 2-fluoroethyl, 2,2-difluoroethyl, 2,2,2-trifluoroethyl, pentafluoroethyl, 3,3,3-trifluoropropyl or 1,3-difluoropropan-2-yl.

The term "—S—$C_1$-$C_4$-halogenoalkyl", "—S(O)—$C_1$-$C_4$-halogenoalkyl" or "—$SO_2$—$C_1$-$C_4$-halogenoalkyl" means a linear or branched, saturated group in which the term "$C_1$-$C_4$-halogenoalkyl" is as defined supra, e.g. a mono-, di- or tri-fluoromethylsulfanyl, mono-, di- or tri-chloromethylsulfanyl, mono-, di- or tri-fluoroethylsulfanyl, mono-, di- or tri-chloroethylsulfanyl, mono-, di- or tri-fluoropropylsulfanyl, mono-, di- or tri-chloropropylsulfanyl, mono-, di- or tri-fluorobutylsulfanyl, mono-, di- or tri-chlorobutylsulfanyl group, or a mono-, di- or tri-fluoromethylsulfinyl, mono-, di- or tri-chloromethylsulfinyl, mono-, di- or tri-fluoroethylsulfinyl, mono-, di- or tri-chloroethylsulfinyl, mono-, di- or tri-fluoropropylsulfinyl, mono-, di- or tri-chloropropylsulfinyl, mono-, di- or tri-fluorobutylsulfinyl, mono-, di- or tri-chlorobutylsulfinyl group, or a mono-, di- or tri-fluoromethylsulfonyl, mono-, di- or tri-chloromethylsulfonyl, mono-, di- or tri-fluoroethylsulfonyl, mono-, di- or tri-chloroethylsulfonyl, mono-, di- or tri-fluoropropylsulfonyl, mono-, di- or tri-chloropropylsulfonyl, mono-, di- or tri-fluorobutylsulfonyl, mono-, di- or tri-chlorobutylsulfonyl group.

The term "$C_1$-$C_4$-alkoxy" means a linear or branched, saturated, monovalent group of formula ($C_1$-$C_4$-alkyl)-O—, in which the term "$C_1$-$C_4$-alkyl" is as defined supra, e.g. a methoxy, ethoxy, n-propoxy, isopropoxy, n-butoxy, sec-butoxy, isobutoxy or tert-butoxy group, or an isomer thereof.

The term "$C_1$-$C_4$-halogenoalkoxy" means a linear or branched, saturated, monovalent $C_1$-$C_4$-alkoxy group, as defined supra, in which one or more of the hydrogen atoms is replaced, identically or differently, with a halogen atom. Particularly, said halogen atom is a fluorine atom. Said $C_1$-$C_4$-halogenoalkoxy group is, for example, fluoromethoxy, difluoromethoxy, trifluoromethoxy, 2,2,2-trifluoroethoxy or pentafluoroethoxy.

The term "$C_2$-$C_4$-alkenyl" means a linear or branched, monovalent hydrocarbon group, which contains one double bond, and which has 2, 3 or 4 carbon atoms. Said $C_2$-$C_4$-alkenyl group is, for example, an ethenyl (or "vinyl"), a prop-2-en-1-yl (or "allyl"), prop-1-en-1-yl, but-3-enyl, but-2-enyl, but-1-enyl, prop-1-en-2-yl (or "isopropenyl"), 2-methylprop-2-enyl, 1-methylprop-2-enyl, 2-methylprop-1-enyl or a 1-methylprop-1-enyl, group. Particularly, said group is allyl.

The term "$C_2$-$C_4$-alkynyl" means a linear monovalent hydrocarbon group which contains one triple bond, and which contains 2, 3 or 4 carbon atoms. Said $C_2$-$C_4$-alkynyl group is, for example, an ethynyl, a prop-1-ynyl, prop-2-ynyl (or "propargyl"), but-1-ynyl, but-2-ynyl, but-3-ynyl or 1-methylprop-2-ynyl, group. Particularly, said alkynyl group is prop-1-ynyl or prop-2-ynyl.

The term "$C_3$-$C_6$-cycloalkyl" means a saturated, monovalent, monocyclic hydrocarbon ring which contains 3, 4, 5 or 6 carbon atoms ("$C_3$-$C_6$-cycloalkyl"). Said $C_3$-$C_6$-cycloalkyl group is for example, a monocyclic hydrocarbon ring, e.g. a cyclopropyl, cyclobutyl, cyclopentyl or cyclohexyl group.

The term "$C_3$-$C_6$-halogenocycloalkyl" means a saturated, monovalent, monocyclic hydrocarbon ring in which the term "$C_3$-$C_6$-cycloalkyl" is as defined supra, and in which one or more of the hydrogen atoms are replaced, identically or differently, with a halogen atom. Particularly, said halogen atom is a fluorine or chlorine atom. Said $C_3$-$C_6$-halogenocycloalkyl group is for example, a monocyclic hydrocarbon ring substituted with one or two fluorine or chlorine atoms, e.g. a 1-fluoro-cyclopropyl, 2-fluorocyclopropyl, 2,2-difluorocyclopropyl, 2,3-difluorocyclopropyl, 1-chlorocyclopropyl, 2-chlorocyclopropyl, 2,2-dichlorocyclopropyl, 2,3-dichlorocyclopropyl, 2-fluoro-2-chlorocyclopropyl and 2-fluoro-3-chlorocyclopropyl group.

The term "benzo-$C_5$-$C_6$-cycloalkyl" means a monovalent, bicyclic hydrocarbon ring wherein a saturated, monovalent, monocyclic hydrocarbon ring which contains 5 or 6 carbon atoms ("$C_5$-$C_6$-cycloalkyl") is annelated to a phenyl ring. Said benzo-$C_5$-$C_6$-cycloalkyl group is for example, a bicyclic hydrocarbon ring, e.g. an indane (i.e. 2,3-dihydro-1H-indene) or tetraline (i.e. 1,2,3,4-tetrahydronaphthalene) group.

The term "spirocycloalkyl" means a saturated, monovalent bicyclic hydrocarbon group in which the two rings share one common ring carbon atom, and wherein said bicyclic hydrocarbon group contains 5, 6, 7, 8, 9, 10 or 11 carbon atoms, it being possible for said spirocycloalkyl group to be attached to the rest of the molecule via any one of the carbon atoms except the spiro carbon atom. Said spirocycloalkyl group is, for example, spiro[2.2]pentyl, spiro[2.3]hexyl, spiro[2.4]heptyl, spiro[2.5]octyl, spiro[2.6]nonyl, spiro[3.3]heptyl, spiro[3.4]octyl, spiro[3.5]nonyl, spiro[3.6]decyl, spiro[4.4]nonyl, spiro[4.5]decyl, spiro[4.6]undecyl or spiro[5.5]undecyl.

The term "heterocycloalkyl" means a monocyclic or bicyclic, saturated or partially saturated heterocycle with 4, 5, 6, 7, 8, 9 or 10 ring atoms in total (a "4- to 10-membered heterocycloalkyl" group), particularly 4, 5 or 6 ring atoms (a "4- to 6-membered heterocycloalkyl" group), which contains one or two identical or different ring heteroatoms from the series N, O and S, it being possible for said heterocycloalkyl group to be attached to the rest of the molecule via any one of the carbon atoms or, if present, a nitrogen atom.

Said heterocycloalkyl group, without being limited thereto, can be a 4-membered ring, such as azetidinyl, oxetanyl or thietanyl, for example; or a 5-membered ring, such as tetrahydrofuranyl, oxolanyl, 1,3-dioxolanyl, thiolanyl, pyrrolidinyl, imidazolidinyl, pyrazolidinyl, 1,1-dioxidothiolanyl, 1,2-oxazolidinyl, 1,3-oxazolidinyl, 1,3-thiazolidinyl or 1,2,4-triazolidinyl, for example; or a 6-membered ring, such as tetrahydropyranyl, tetrahydrothiopyranyl, piperidinyl, morpholinyl, dithianyl, thiomorpholinyl, piperazinyl, oxanyl, 1,3-dioxanyl, 1,4-dioxanyl or 1,2-oxazinanyl, for example; or a 7-membered ring, such as azepanyl, 1,4-diazepanyl or 1,4-oxazepanyl, for example; or a bicyclic 7-membered ring, such as 6-oxa-3-azabicyclo[3.1.1]heptan, for example; or a bicyclic 8-membered ring, such as 5,6-dihydro-4H-furo[2,3-c]pyrrole or 8-oxa-3-azabicyclo[3.2.1]octan, for example; or a bicyclic 9-membered ring, such as octahydro-1H-pyrrolo[3,4-b]pyridine, 1,3-dihydro-isoindol, 2,3-dihydro-indol or 3,9-dioxa-7-azabicyclo[3.3.1]nonan, for example; or a bicyclic 10-membered ring, such as decahydroquinoline or 3,4-dihydroisoquinolin, for example.

The term "heterospirocycloalkyl" means a bicyclic, saturated heterocycle with 6, 7, 8, 9, 10 or 11 ring atoms in total, in which the two rings share one common ring carbon atom, which "heterospirocycloalkyl" contains one or two identical or different ring heteroatoms from the series: N, O, S; it being possible for said heterospirocycloalkyl group to be attached to the rest of the molecule via any one of the carbon atoms, except the spiro carbon atom, or, if present, a nitrogen atom.

Said heterospirocycloalkyl group is, for example, azaspiro[2.3]hexyl, azaspiro[3.3]heptyl, oxaazaspiro[3.3]heptyl, thiaazaspiro[3.3]heptyl, oxaspiro[3.3]heptyl, oxazaspiro[5.3]nonyl, oxazaspiro[4.3]octyl, oxaazaspiro[2.5]octyl, azaspiro[4.5]decyl, oxazaspiro[5.5]undecyl, diazaspiro[3.3]heptyl, thiazaspiro[3.3]heptyl, thiazaspiro[4.3]octyl, azaspiro[5.5]undecyl, or one of the further homologous scaffolds such as spiro[3.4]-, spiro[4.4]-, spiro[2.4]-, spiro[2.5]-, spiro[2.6]-, spiro[3.5]-, spiro[3.6]-, spiro[4.5]- and spiro[4.6]-.

The term "6- or 10-membered aryl" means a monovalent, monocyclic or bicyclic aromatic ring having 6 or 10 carbon ring atoms, e.g. a phenyl or naphthyl group.

The term "heteroaryl" means a monovalent, monocyclic, bicyclic or tricyclic aromatic ring having 5, 6, 9 or 10 ring atoms (a "5- to 10-membered heteroaryl" group), particularly 5 or 6 ring atoms (a "5- to 6-membered heteroaryl" group), which contains at least one ring heteroatom and optionally one, two or three further ring heteroatoms from the series: N, O and/or S, and which is bound via a ring carbon atom or optionally via a ring nitrogen atom (if allowed by valency).

Said heteroaryl group can be a 5-membered heteroaryl group, such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, such as, for example, pyridinyl, dihydropyridinyl, pyridazinyl, pyrimidinyl, tetrahydropyrimidinyl, pyrazinyl or triazinyl.

The term "heterocyclyl" means a heterocycle selected from the group consisting of heterocycloalkyl and heteroaryl. Particularly, the term "4- to 6-membered heterocyclyl" means a heterocycle selected from the group consisting of 4- to 6-membered heterocycloalkyl and 5- to 6-membered heteroaryl.

In general, and unless otherwise mentioned, the heteroaryl or heteroarylene groups include all possible isomeric forms thereof, e.g.: tautomers and positional isomers with respect to the point of linkage to the rest of the molecule. Thus, for some illustrative non-restricting examples, the term pyridinyl includes pyridin-2-yl, pyridin-3-yl and pyridin-4-yl; or the term thienyl includes thien-2-yl and thien-3-yl.

The term "$C_1$-$C_4$", as used in the present text, e.g. in the context of the definition of "$C_1$-$C_4$-alkyl", "$C_1$-$C_4$-halogenoalkyl", "$C_1$-$C_4$-hydroxyalkyl", "$C_1$-$C_4$-alkoxy" or "$C_1$-$C_4$-halogenoalkoxy" means an alkyl group having a finite number of carbon atoms of 1 to 4, i.e. 1, 2, 3 or 4 carbon atoms.

Further, as used herein, the term "$C_3$-$C_6$", as used in the present text, e.g. in the context of the definition of "$C_3$-$C_6$-cycloalkyl" or $C_3$-$C_6$-halogenocycloalkyl, means a cycloalkyl group having a finite number of carbon atoms of 3 to 6, i.e. 3, 4, 5 or 6 carbon atoms.

When a range of values is given, said range encompasses each value and sub-range within said range.

For example:
"$C_1$-$C_4$" encompasses $C_1$, $C_2$, $C_3$, $C_4$, $C_1$-$C_4$, $C_1$-$C_3$, $C_1$-$C_2$, $C_2$-$C_4$, $C_2$-$C_3$, and $C_3$-$C_4$;

"$C_2$-$C_6$" encompasses $C_2$, $C_3$, $C_4$, $C_5$, $C_6$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$;

"$C_3$-$C_4$" encompasses $C_3$, $C_4$, and $C_3$-$C_4$;

"$C_3$-$C_{10}$" encompasses $C_3$, $C_4$, $C_5$, $C_6$, $C_7$, $C_8$, $C_9$, $C_{10}$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_4$-$C_{10}$, $C_4$-$C_9$, $C_4$-$C_8$, $C_4$-$C_7$, $C_4$-$C_6$, $C_4$-$C_8$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$;

"$C_3$-$C_8$" encompasses $C_3$, $C_4$, $C_5$, $C_6$, $C_7$, $C_8$, $C_3$-$C_8$, $C_3$-$C_7$, $C_3$-$C_6$, $C_3$-$C_5$, $C_3$-$C_4$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;

"$C_3$-$C_6$" encompasses $C_3$, $C_4$, $C_5$, $C_6$, $C_3$-$C_6$, $C_3$-$C_5$, $C_3$-$C_4$, $C_4$-$C_6$, $C_4$-$C_5$, and $C_5$-$C_6$;

"$C_4$-$C_8$" encompasses $C_4$, $C_5$, $C_6$, $C_7$, $C_8$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;

"$C_4$-$C_7$" encompasses $C_4$, $C_5$, $C_6$, $C_7$, $C_4$-$C_7$, $C_4$-$C_6$, $C_4$-$C_5$, $C_5$-$C_7$, $C_5$-$C_6$ and $C_6$-$C_7$;

"$C_4$-$C_6$" encompasses $C_4$, $C_5$, $C_6$, $C_4$-$C_6$, $C_4$-$C_5$ and $C_5$-$C_6$;

"$C_5$-$C_{10}$" encompasses $C_5$, $C_6$, $C_7$, $C_8$, $C_9$, $C_{10}$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$;

"$C_6$-$C_{10}$" encompasses $C_6$, $C_7$, $C_8$, $C_9$, $C_{10}$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$.

As used herein, the term "leaving group" means an atom or a group of atoms that is displaced in a chemical reaction as stable species taking with it the bonding electrons. In particular, such a leaving group is selected from the group comprising: halide, in particular fluoride, chloride, bromide or iodide, (methylsulfonyl)oxy, [(trifluoromethyl)sulfonyl]oxy, [(nonafluorobutyl)sulfonyl]oxy, (phenylsulfonyl)oxy, [(4-methylphenyl)sulfonyl]oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butyl-phenyl)sulfonyl]oxy and [(4-methoxyphenyl)sulfonyl]oxy.

An oxo substituent in the context of the invention means an oxygen atom, which is bound to a carbon atom via a double bond.

It is possible for the compounds of general formula (I) to exist as isotopic variants. The invention therefore includes one or more isotopic variant(s) of the compounds of general formula (I), particularly deuterium-containing compounds of general formula (I).

The term "Isotopic variant" of a compound or a reagent is defined as a compound exhibiting an unnatural proportion of one or more of the isotopes that constitute such a compound.

The term "Isotopic variant of the compound of general formula (I)" is defined as a compound of general formula (I) exhibiting an unnatural proportion of one or more of the isotopes that constitute such a compound.

The expression "unnatural proportion" means a proportion of such isotope which is higher than its natural abundance. The natural abundances of isotopes to be applied in this context are described in "Isotopic Compositions of the Elements 1997", Pure Appl. Chem., 70(1), 217-235, 1998.

Examples of such isotopes include stable and radioactive isotopes of hydrogen, carbon, nitrogen, oxygen, phosphorus, sulfur, fluorine, chlorine, bromine and iodine, such as $^{2}$H (deuterium), $^{3}$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{125}$I, $^{129}$I and $^{131}$I, respectively.

With respect to the treatment and/or prevention of the disorders specified herein the isotopic variant(s) of the compounds of general formula (I) preferably contain deuterium ("deuterium-containing compounds of general formula (I)"). Isotopic variants of the compounds of general formula (I) in which one or more radioactive isotopes, such as $^{3}$H or $^{14}$C, are incorporated are useful e.g. in drug and/or substrate tissue distribution studies. These isotopes are particularly preferred for the ease of their incorporation and detectability. Positron emitting isotopes such as $^{18}$F or $^{11}$C may be incorporated into a compound of general formula (I). These isotopic variants of the compounds of general formula (I) are useful for in vivo imaging applications. Deuterium-containing and $^{13}$C-containing compounds of general formula (I) can be used in mass spectrometry analyses in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from $D_2O$ can be incorporated either directly into the compounds or into reagents that are useful for synthesizing such compounds. Deuterium gas is also a useful reagent for incorporating deuterium into molecules. Catalytic deuteration of olefinic bonds and acetylenic bonds is a rapid route for incorporation of deuterium. Metal catalysts (i.e. Pd, Pt, and Rh) in the presence of deuterium gas can be used to directly exchange deuterium for hydrogen in functional groups containing hydrocarbons. A variety of deuterated reagents and synthetic building blocks are commercially available from companies such as for example C/D/N Isotopes, Quebec, Canada; Cambridge Isotope Laboratories Inc., Andover, MA, USA; and CombiPhos Catalysts, Inc., Princeton, NJ, USA.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490], basicity [C. L. Perrin et al., J. Am. Chem. Soc., 2005, 127, 9641], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome $P_{450}$.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The compounds of the present invention optionally contain one or more asymmetric centres, depending upon the location and nature of the various substituents desired. It is possible that one or more asymmetric carbon atoms are present in the (R) or (S) configuration, which can result in racemic mixtures in the case of a single asymmetric centre, and in diastereomeric mixtures in the case of multiple asymmetric centres. In certain instances, it is possible that asymmetry also be present due to restricted rotation about a given bond, for example, the central bond adjoining two substituted aromatic rings of the specified compounds.

Preferred compounds are those which produce the more desirable biological activity. Separated, pure or partially purified isomers and stereoisomers or racemic or diastereomeric mixtures of the compounds of the present invention are also included within the scope of the present invention.

The purification and the separation of such materials can be accomplished by standard techniques known in the art.

Preferred isomers are those which produce the more desirable biological activity. These separated, pure or partially purified isomers or racemic mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers.

Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R)- or (S)-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also covers useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention contain polar solvents, in particular water, methanol or ethanol for example, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, it is possible for the compounds of the present invention to exist in free form, e.g. as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethanesulfonic, dodecylsulfuric, ethanesulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethyl-glucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quarternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

Those skilled in the art will further recognise that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae relating to salts, such as "hydrochloride", "trifluoroacetate", "sodium salt", or "x HCl", "x CF$_3$COOH", "x Na$^+$", for example, mean a salt form, the stoichiometry of which salt form not being specified.

This applies analogously to cases in which synthesis intermediates or example compounds or salts thereof have been obtained, by the preparation and/or purification processes described, as solvates, such as hydrates, with (if defined) unknown stoichiometric composition.

Furthermore, the present invention includes all possible crystalline forms, or polymorphs, of the compounds of the present invention, either as single polymorph, or as a mixture of more than one polymorph, in any ratio.

Moreover, the present invention also includes prodrugs of the compounds according to the invention. The term "prodrugs" here designates compounds which themselves can be biologically active or inactive, but are converted (for example metabolically or hydrolytically) into compounds according to the invention during their residence time in the body.

In accordance with a second embodiment of the first aspect, the present invention covers compounds of general formula (I), supra, in which:

A is A1 or A2,

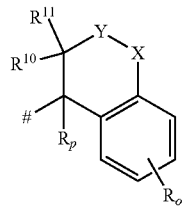

A1

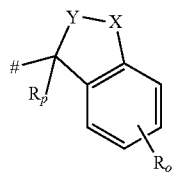

A2 o is 0, 1, 2, 3 or 4,

R is selected from the group consisting of hydrogen, halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, —S—$C_1$-$C_4$-halogenoalkyl, —S(O)—$C_1$-$C_4$-halogenoalkyl and —SO$_2$-$C_1$-$C_4$-halogenoalkyl having 1 to 5 halogen atoms, $R_p$ is selected from the group consisting of hydrogen, $C_1$-$C_4$-alkyl, X, Y are independently selected from the group consisting of CR$^7$R$^8$, O, S, and N—R$^9$, wherein at least one of X and Y is CR$^7$R$^8$, or X, Y form together a ring member selected from the group consisting of —C(O)—O—, —C(O)—NR$^9$—, —S(O)—NR$^9$—, —SO$_2$—NR$^9$— and —SO$_2$—O—, R$^1$ is selected from the group consisting of hydrogen, cyano, —CHO, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, $C_3$-$C_6$-halogenocycloalkyl having 1 to 5 halogen atoms, $C_3$-$C_4$-alkenyl, $C_3$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, —NH—$C_1$-$C_4$-alkyl, —N($C_1$-$C_4$-alkyl)$_2$, NH$_2$-$C_1$-$C_4$-alkyl-, $C_1$-$C_4$-alkyl-NH—$C_1$-$C_4$-alkyl-, ($C_1$-$C_4$-alkyl)$_2$N—$C_1$-$C_4$-alkyl-, $C_1$-$C_4$-alkyl-C(O)—, $C_1$-$C_4$-halogenoalkyl-C(O)— having 1 to 5 halogen atoms, $C_1$-$C_4$-alkoxy-C(O)—, benzyloxy-C(O)—, $C_1$-$C_4$-alkoxy-$C_1$-$C_4$-alkyl-C(O)—, —SO$_2$—$C_1$-$C_4$-alkyl, and —SO$_2$—$C_1$-$C_4$-halogenoalkyl having 1 to 5 halogen atoms;

phenyl-$C_1$-$C_4$-alkyl, optionally substituted by 1, 2, 3, 4 or 5 substituents independently selected from the group consisting of halogen, —OH, —NO$_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —SO$_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —NO$_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —SO$_2$—$C_1$-$C_4$-halogenoalkyl having 1 to 5 halogen atoms, R$^2$ is selected from the group consisting of
hydrogen, halogen, cyano, —COOH, $C_1$-$C_4$-alkoxy-C(O)—, —C(O)—NH$_2$, —C(O)—NH($C_1$-$C_4$-alkyl), —C(O)—N($C_1$-$C_4$-alkyl)$_2$;
—NR$^{12}$R$^{13}$;
—OR$^{14}$;
—SR$^{15}$, —S(O)R$^{15}$, —SO$_2$R$^{15}$;
$C_1$-$C_6$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted by 1, 2, 3, 4 or 5 substituents independently selected from the group consisting of halogen, —OH, —NO$_2$, cyano, $C_1$-$C_4$-alkyl-C(O)—, $C_1$-$C_4$-alkoxy-C(O)—, —C(O)—NH$_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, —NH$_2$, —NH($C_1$-$C_4$-alkyl), —N($C_1$-$C_4$-alkyl)$_2$, —NH(C(O)—$C_1$-$C_4$-alkyl), —N($C_1$-$C_4$-alkyl)(C(O)—$C_1$-$C_4$-alkyl), —S—$C_1$-$C_4$-alkyl, —S(O)—$C_1$-$C_4$-alkyl, —SO$_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —SO$_2$—C$_1$-C$_4$-halogenoalkyl having 1 to 5 halogen atoms;

heterocyclyl-C$_1$-C$_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —NO$_2$, cyano, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms;

phenyl which is optionally substituted by 1, 2 or 3 substituents independently selected from the group consisting of halogen, cyano, nitro, —OH, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$-C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms; and a monocyclic or a bicyclic heterocycle selected from the group consisting of 4- to 10-membered heterocycloalkyl, heterospirocycloalkyl, 5-membered heteroaryl and 6-membered heteroaryl, each of which is optionally substituted by 1, 2, 3 or 4 substituents independently selected from the group consisting of halogen, cyano, nitro, —OH, oxo, thiono, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, C$_1$-C$_4$-alkyl, C$_1$-C$_4$-alkyl-C(O)—, C$_1$-C$_4$-halogenoalkyl having 1 to 5 halogen atoms, C$_1$-C$_4$-alkoxy, hydroxy-C$_1$-C$_4$-alkyl, C$_1$-C$_4$-alkoxy-C$_1$-C$_4$-alkyl-, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms, —SO$_2$—C$_1$-C$_4$-halogenoalkyl having 1 to 5 halogen atoms and 4- to 10-membered heterocycloalkyl, R$^3$ is hydrogen, or C$_1$-C$_4$-alkyl, R$^4$ is selected from the group consisting of hydrogen, halogen, —OH, cyano, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, —NH$_2$, —NH(C$_1$-C$_4$-alkyl), —N(C$_1$-C$_4$-alkyl)$_2$, preferably hydrogen and halogen, more preferably fluorine and chlorine, R$^5$ is selected from the group consisting of hydrogen, halogen, —OH, cyano, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, —NH$_2$, —NH(C$_1$-C$_4$-alkyl), —N(C$_1$-C$_4$-alkyl)$_2$, R$^6$ is selected from the group consisting of hydrogen, halogen, —OH, cyano, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, —NH$_2$, —NH(C$_1$-C$_4$-alkyl), —N(C$_1$-C$_4$-alkyl)$_2$, R$^7$ is selected from the group consisting of hydrogen, —OH, fluorine, C$_1$-C$_4$-alkyl and C$_1$-C$_4$-alkoxy, R$^8$ is selected from the group consisting of hydrogen, —OH, fluorine, C$_1$-C$_4$-alkyl and C$_1$-C$_4$-alkoxy, or R$^7$ and R$^8$ together form an oxo group (=O), R$^9$ is selected from the group consisting of hydrogen, C$_1$-C$_4$-alkyl, C$_1$-C$_4$-halogenoalkyl having 1 to 5 halogen atoms and C$_1$-C$_4$-alkoxy, R$^{10}$ is selected from the group consisting of hydrogen, —OH, C$_1$-C$_4$-alkyl and C$_1$-C$_4$-alkoxy, R$^{11}$ is selected from the group consisting of hydrogen, C$_1$-C$_4$-alkyl and C$_1$-C$_4$-alkoxy, R$^{12}$ and R$^{13}$ are independently selected from the group consisting of hydrogen, —OH, —NH$_2$, —NH(C$_1$-C$_4$-alkyl), —N(C$_1$-C$_4$-alkyl)$_2$, —NH(—C(O)—C$_1$-C$_4$-alkyl), C$_1$-C$_4$-alkoxy;

C$_1$-C$_4$-alkyl, C$_3$-C$_6$-cycloalkyl, phenyl-C$_1$-C$_4$-alkyl, each of which is optionally substituted by 1, 2 or 3 substituents independently selected from the group consisting of halogen, —OH, cyano, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, —NH—C(O)—C$_1$-C$_4$-alkyl, —N(C$_1$-C$_4$-alkyl)-(—C(O)—C$_1$-C$_4$-alkyl), C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms, —SO$_2$—C$_1$-C$_4$-halogenoalkyl having 1 to 5 halogen atoms and (C$_1$-C$_4$-alkoxy)$_2$P(=O)—;

heterocyclyl-C$_1$-C$_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, C$_1$-C$_4$-alkyl, C$_1$-C$_4$-halogenoalkyl having 1 to 5 halogen atoms, C$_1$-C$_4$-alkoxy, hydroxy-C$_1$-C$_4$-alkyl, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms;

phenyl, benzo-C$_5$-C$_6$-cycloalkyl, each of which is optionally substituted by 1, 2 or 3 substituents independently selected from the group consisting of halogen, cyano, nitro, —OH, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms; and a monocyclic or a bicyclic heterocycle selected from the group of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$-$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^{14}$ is selected from the group consisting of
—$NH_2$, —NH($C_1$-$C_4$-alkyl), —N($C_1$-$C_4$-alkyl)$_2$;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substitutent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$-$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$-$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^{15}$ is selected from the group consisting of
hydrogen;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$-$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —SO$_2$—C$_1$-C$_4$-halogenoalkyl having 1 to 5 halogen atoms; and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, C$_1$-C$_4$-alkyl, C$_1$-C$_4$-halogenoalkyl having 1 to 5 halogen atoms, C$_1$-C$_4$-alkoxy, hydroxy-C$_1$-C$_4$-alkyl, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms, Q is a substituted phenyl ring of the formula (Q1)

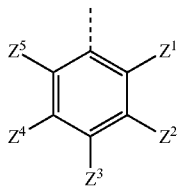

(Q1)

in which:

Z$^1$, Z$^2$, Z$^3$, Z$^4$, and Z$^5$ are independently selected from the group consisting of hydrogen, halogen, SF$_5$, cyano, —CHO, nitro, C$_1$-C$_4$-alkyl, C$_1$-C$_4$-halogenoalkyl having 1 to 5 halogen atoms, hydroxy, C$_1$-C$_4$-alkoxy, C$_3$-C$_6$-cycloalkyl-C$_1$-C$_4$-alkoxy, cyano-C$_1$-C$_4$-alkoxy, C$_1$-C$_4$-halogenoalkoxy having 1 to 5 halogen atoms, —NH(C$_1$-C$_4$-alkyl), —N(C$_1$-C$_4$-alkyl)$_2$, —NH—SO$_2$—(C$_1$-C$_4$-alkyl), —N(SO$_2$—[C$_1$-C$_4$-alkyl])(C$_1$-C$_4$-alkyl), (C$_1$-C$_4$-alkoxyimino)-C$_1$-C$_4$-alkyl, 4- to 6-membered heterocyclyl, which is optionally substituted with 1 or 2 substituents selected from the group consisting of fluorine, chlorine, bromine, methyl and cyano, —CH$_2$—O—(C$_1$-C$_4$-alkyl), —CH$_2$—NH(C$_1$-C$_4$-alkyl), —CH$_2$—N(C$_1$-C$_4$-alkyl)$_2$, methyl substituted with a 4- to 6-membered heterocyclyl which itself is optionally substituted with 1 or 2 substituents selected from the group consisting of fluorine, chlorine, bromine, methyl and cyano, —CH$_2$—S—(C$_1$-C$_4$-alkyl), —CH$_2$—S(O)—(C$_1$-C$_4$-alkyl), —CH$_2$—SO$_2$—(C$_1$-C$_4$-alkyl), —S—(C$_1$-C$_4$-alkyl), —S(O)—(C$_1$-C$_4$-alkyl), —SO$_2$—(C$_1$-C$_4$-alkyl), —S—(C$_1$-C$_4$-halogenoalkyl) having 1 to 5 halogen atoms, —S(O)—(C$_1$-C$_4$-halogenoalkyl) having 1 to 5 halogen atoms, —SO$_2$—(C$_1$-C$_4$-halogenoalkyl) having 1 to 5 halogen atoms, —CONH(C$_1$-C$_4$-alkyl), —CONH(C$_3$-C$_6$-cycloalkyl), —NHCO(C$_1$-C$_4$-alkyl), —NHCO(C$_3$-C$_6$-cycloalkyl), —NHCO(C$_1$-C$_4$-halogenoalkyl) having 1 to 5 halogen atoms, or Z$^1$ and Z$^2$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two substituents selected from the group consisting of methyl, fluorine and oxo, and Z$^3$, Z$^4$, and Z$^5$ are independently selected from the group consisting of hydrogen, halogen, SF$_5$, cyano, CHO, nitro, C$_1$-C$_4$-alkyl, C$_1$-C$_4$-halogenoalkyl having 1 to 5 halogen atoms, hydroxy, C$_1$-C$_4$-alkoxy, C$_3$-C$_6$-cycloalkyl-C$_1$-C$_4$-alkoxy, cyano-C$_1$-C$_4$-alkoxy, C$_1$-C$_4$-alkoxy-C(O)—, C$_1$-C$_4$-halogenoalkoxy having 1 to 5 halogen atoms, —NH(C$_1$-C$_4$-alkyl), —N(C$_1$-C$_4$-alkyl)$_2$, —NH—SO$_2$—(C$_1$-C$_4$-alkyl), —N(SO$_2$—[C$_1$-C$_4$-alkyl])(C$_1$-C$_4$-alkyl), (C$_1$-C$_4$-alkoxyimino)-C$_1$-C$_4$-alkyl, 4- to 6-membered heterocycloalkyl which is optionally substituted with 1 or 2 substituents selected from the group consisting of fluorine, methyl or cyano, —CH$_2$—O—(C$_1$-C$_4$-alkyl), —CH$_2$—NH(C$_1$-C$_4$-alkyl), —CH$_2$—N(C$_1$-C$_4$-alkyl)$_2$, methyl substituted with a 4- to 6-membered heterocycloalkyl which itself is optionally substituted with 1 or 2 substituents selected from the group consisting of fluorine, methyl or cyano, —CH$_2$—S—(C$_1$-C$_4$-alkyl), —CH$_2$—S(O)—(C$_1$-C$_4$-alkyl), —CH$_2$—SO$_2$—(C$_1$-C$_4$-alkyl), —S—(C$_1$-C$_4$-alkyl), —S(O)—(C$_1$-C$_4$-alkyl), —SO$_2$—(C$_1$-C$_4$-alkyl), —S—(C$_1$-C$_4$-halogenoalkyl) having 1 to 5 halogen atoms, —S(O)—(C$_1$-C$_4$-halogenoalkyl) having 1 to 5 halogen atoms, —SO$_2$—(C$_1$-C$_4$-halogenoalkyl) having 1 to 5 halogen atoms, —CONH(C$_1$-C$_4$-alkyl), —CONH(C$_3$-C$_6$-cycloalkyl), —NHCO(C$_1$-C$_4$-alkyl), —NHCO(C$_3$-C$_6$-cycloalkyl), —NHCO(C$_1$-C$_4$-halogenoalkyl) having 1 to 5 halogen atoms, or Z$^2$ and Z$^3$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two substituents selected from the group consisting of methyl, fluorine and oxo, and Z$^1$, Z$^4$, and Z$^5$ are independently selected from the group consisting of hydrogen, halogen, SF$_5$, cyano, CHO, nitro, C$_1$-C$_4$-alkyl, C$_1$-C$_4$-halogenoalkyl having 1 to 5 halogen atoms, hydroxy, C$_1$-C$_4$-alkoxy, C$_3$-C$_6$-cycloalkyl-C$_1$-C$_4$-alkoxy, cyano-C$_1$-C$_4$-alkoxy, C$_1$-C$_4$-halogenoalkoxy having 1 to 5 halogen atoms, —NH(C$_1$-C$_4$-alkyl), —N(C$_1$-C$_4$-alkyl)$_2$, —NH—SO$_2$—(C$_1$-C$_4$-alkyl), —N(SO$_2$—[C$_1$-C$_4$-alkyl])(C$_1$-C$_4$-alkyl), (C$_1$-C$_4$-alkoxyimino)-C$_1$-C$_4$-alkyl, 4- to 6-membered heterocycloalkyl which is optionally substituted with 1 or 2 substituents selected from the group consisting of fluorine, methyl or cyano, —CH$_2$—O—(C$_1$-C$_4$-alkyl), —CH$_2$—NH(C$_1$-C$_4$-alkyl), —CH$_2$—N(C$_1$-C$_4$-alkyl)$_2$, methyl substituted with a 4- to 6-membered heterocycloalkyl which itself is optionally substituted with 1 or 2 substituents selected from the group consisting of fluorine, methyl or cyano, —CH$_2$—S—(C$_1$-C$_4$-alkyl), —CH$_2$—S(O)—(C$_1$-C$_4$-alkyl), —CH$_2$—SO$_2$—(C$_1$-C$_4$-alkyl), —S—(C$_1$-C$_4$-alkyl), —S(O)—(C$_1$-C$_4$-alkyl), —SO$_2$—(C$_1$-C$_4$-alkyl), —S—(C$_1$-C$_4$-halogenoalkyl) having 1 to 5 halogen atoms, —S(O)—(C$_1$-C$_4$-halogenoalkyl) having 1 to 5 halogen atoms, —SO$_2$—(C$_1$-C$_4$-halogenoalkyl) having 1 to 5 halogen atoms, —CONH(C$_1$-C$_4$-alkyl), —CONH(C$_3$-C$_6$-cycloalkyl), —NHCO(C$_1$-C$_4$- alkyl), —NHCO(C$_3$-C$_6$-cycloalkyl), —NHCO(C$_1$-C$_4$-halogenoalkyl) having 1 to 5 halogen atoms, or Q is a pyridine ring of the formula (Q2)

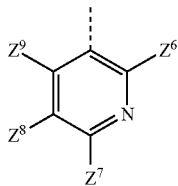

(Q2)

in which:
Z$^6$, Z$^7$, Z$^8$ and Z$^9$ are independently selected from the group consisting of hydrogen, halogen, cyano, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, —NH(C$_1$-C$_4$-alkyl), —N(C$_1$-C$_4$-alkyl)$_2$, or Q is a pyrimidine ring of the formula (Q3)

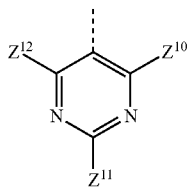

(Q3)

in which:
Z$^{10}$, Z$^{11}$ and Z$^{12}$ are independently selected from the group consisting of hydrogen, halogen, cyano, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, —NH(C$_1$-C$_4$-alkyl), —N(C$_1$-C$_4$-alkyl)$_2$, or Q is a pyridine ring of the formula (Q4)

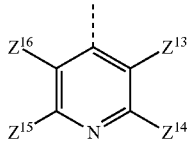

(Q4)

in which:
Z$^{13}$, Z$^{14}$, Z$^{15}$ and Z$^{16}$ are independently selected from the group consisting of hydrogen halogen, cyano, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, C$_1$-C$_4$-hydroxyalkyl, NH$_2$, —NH(C$_1$-C$_4$-alkyl), —N(C$_1$-C$_4$-alkyl)$_2$, —NH—CO—C$_1$-C$_4$-alkyl, and monocyclic heterocycles selected from the group of 4- to 7-membered heterocycloalkyl or 5-membered heteroaryls having at least one nitrogen atom via which the heteroaryl ring is connected to the pyridine ring, each of which is optionally substituted with 1, 2 or 3 substituents independently selected from the group consisting of halogen, cyano, nitro, —OH, oxo, thiono, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—(C$_1$-C$_4$-halogenoalkyl) having 1 to 5 halogen atoms, —S(O)—(C$_1$-C$_4$-halogenoalkyl) having 1 to 5 halogen atoms, —SO$_2$—(C$_1$-C$_4$-halogenoalkyl) having 1 to 5 halogen atoms, or Q is a pyridine ring of the formula (Q5)

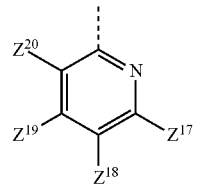

(Q5)

in which:
Z$^{17}$, Z$^{18}$, Z$^{19}$ and Z$^{20}$ are independently selected from the group consisting of hydrogen, halogen, cyano, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, —NH(C$_1$-C$_4$-alkyl), —N(C$_1$-C$_4$-alkyl)$_2$, or Q is a 5-membered aromatic heterocycle of the formula (Q6)

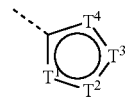

(Q6)

in which:
T$^1$-T$^4$ are independently selected from the group consisting of N, O, S, C—Z$^{21}$ and N—Z$^{22}$, wherein not more than one of T$^1$-T$^4$ is O, not more than one of T$^1$-T$^4$ is S, not more than one of T$^1$-T$^4$ is N—Z$^{22}$, and wherein
each Z$^{21}$ is independently selected from the group consisting of hydrogen, halogen, cyano, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, and
each Z$^{22}$ is independently selected from the group consisting of hydrogen, C$_1$-C$_4$-alkyl, C$_1$-C$_4$-halogenoalkyl having 1 to 5 halogen atoms, C$_1$-C$_4$-alkyl-C$_3$-C$_6$-cycloalkyl, C$_1$-C$_4$-alkoxy-C$_1$-C$_4$-alkyl, or Q is a 5-membered aromatic heterocycle of the formula (Q7)

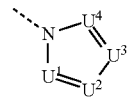

(Q7)

in which:
U$^1$-U$^4$ are independently selected from the group consisting of N and C—Z$^{23}$, wherein not more than three of U$^1$-U$^4$ are N, and wherein each $Z^{23}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, wherein when Y is O, S or N—$R^9$, none of $R^7$, $R^8$, $R^{10}$ and $R^{11}$ is —OH, and wherein when X is O, S or N—$R^9$, none of $R^7$ and $R^8$ is —OH, and stereoisomers, tautomers, N-oxides, hydrates, solvates, and salts thereof, and mixtures of same.

In accordance with a third embodiment of the first aspect, the present invention covers compounds of general formula (I), supra, in which:

A is A1 or A2,

A1

A2 o is 0, 1 or 2,

R is selected from the group consisting of halogen, $C_1$-$C_4$-alkyl and $C_1$-$C_4$-alkoxy, cyano, $C_1$-$C_4$-halogenoalkyl having 1 to 5 halogen atoms, $R_p$ is selected from the group consisting of hydrogen, $C_1$-$C_4$-alkyl, X, Y are independently selected from the group consisting of $CR^7R^8$, O, S, and N—$R^9$, wherein at least one of X and Y is $CR^7R^8$, $R^1$ is selected from the group consisting of hydrogen, $C_1$-$C_4$-alkyl, $C_3$-$C_6$-cycloalkyl, $C_3$-$C_4$-alkenyl, $C_3$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, $R^2$ is selected from the group consisting of
hydrogen, halogen, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$;
—$NR^{12}R^{13}$;
—$OR^{14}$;
—$SR^{15}$, —S(O)$R^{15}$, —$SO_2R^{15}$;
$C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted by 1, 2, 3, 4 or 5 substituents independently selected from the group consisting of halogen, —OH, cyano, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, —$NH_2$, —NH($C_1$-$C_4$-alkyl), —N($C_1$-$C_4$-alkyl)$_2$, —NH(C(O)—$C_1$-$C_4$-alkyl), —N($C_1$-$C_4$-alkyl)(C(O)—$C_1$-$C_4$-alkyl), —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, heterospirocycloalkyl, 5-membered heteroaryl and 6-membered heteroaryl, each of which is optionally substituted by 1, 2, 3 or 4 substituents independently selected from the group consisting of halogen, cyano, —OH, oxo, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-alkyl-C(O)—, $C_1$-$C_4$-halogenoalkyl having 1 to 5 halogen atoms, $C_1$-$C_4$-alkoxy, hydroxy-$C_1$-$C_4$-alkyl, $C_1$-$C_4$-alkoxy-$C_1$-$C_4$-alkyl-, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, and 4- to 10-membered heterocycloalkyl, $R^3$ is hydrogen or $C_1$-$C_4$-alkyl, $R^4$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, preferably hydrogen and halogen, more preferably fluorine and chlorine, $R^5$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, $R^6$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, $R^7$ is selected from the group consisting of hydrogen and $C_1$-$C_4$-alkyl, $R^8$ is selected from the group consisting of hydrogen and $C_1$-$C_4$-alkyl, or $R^7$ and $R^8$ together form an oxo group (=O), $R^9$ is $C_1$-$C_4$-alkyl, $R^{10}$ is selected from the group consisting of —OH, $C_1$-$C_4$-alkyl and $C_1$-$C_4$-alkoxy, $R^{11}$ is hydrogen, $R^{12}$ and $R^{13}$ are independently selected from the group consisting of
hydrogen, —NH(—C(O)—$C_1$-$C_4$-alkyl), $C_1$-$C_4$-alkoxy;
$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, —NH—C(O)—$C_1$-$C_4$-alkyl, —N($C_1$-$C_4$-alkyl)-(—C(O)—$C_1$-$C_4$-alkyl), $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms and ($C_1$-$C_4$-alkoxy)$_2$P(=O)—;

heterocyclyl-$C_1$-$C_4$-alkyl, wherein the heterocyclyl substitutent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

phenyl, benzo-$C_5$-$C_6$-cycloalkyl, each of which is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms; and a monocyclic or a bicyclic heterocycle selected from the group of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $R^{14}$ is selected from the group consisting of $C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl; and heterocyclyl-$C_1$-$C_4$-alkyl, wherein the heterocyclyl substitutent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

$R^{15}$ is selected from the group consisting of hydrogen;

$C_1$-$C_4$-alkyl, phenyl-$C_1$-$C_4$-alkyl, each of which is optionally substituted by 1, 2 or 3 substituents independently selected from the group consisting of halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

Q is a substituted phenyl ring of the formula (Q1)

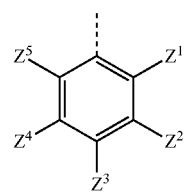

(Q1)

in which:

$Z^1$, $Z^2$, $Z^3$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, hydroxy, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, 4- to 6-membered heterocyclyl, which is optionally substituted with 1 or 2 substituents selected from the group consisting of fluorine, chlorine, bromine, methyl and cyano, —S—($C_1$-$C_4$-alkyl), —S(O)—($C_1$-$C_4$-alkyl), —SO$_2$—($C_1$-$C_4$-alkyl), S—($C_1$-$C_4$-halogenoalkyl) having 1 to 5 halogen atoms, —S(O)—($C_1$-$C_4$-halogenoalkyl) having 1 to 5 halogen atoms, —SO$_2$—($C_1$-$C_4$-halogenoalkyl) having 1 to 5 halogen atoms, or $Z^1$ and $Z^2$ form, together with the carbon atoms that they are connected to, a 5- or 6-membered heterocycloalkyl, a 5-membered heteroaryl, or a 6-membered heteroaryl, each of which may be optionally substituted with one or two substituents selected from the group consisting of methyl, fluorine and oxo, and $Z^3$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-alkoxy-C(O)—, $C_1$-$C_4$-halogenoalkoxy having 1 to 5 halogen atoms, or $Z^2$ and $Z^3$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two substituents selected from the group consisting of methyl, fluorine and oxo, and $Z^1$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, and stereoisomers, tautomers, N-oxides, hydrates, solvates, and salts thereof, and mixtures of same.

In accordance with a fourth embodiment of the first aspect, the present invention covers compounds of general formula (I), supra, in which:

A is A1 or A2,

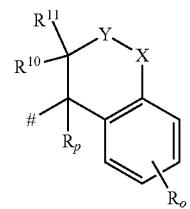

A1

-continued

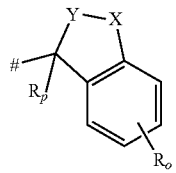
(A2)

o is 0, 1 or 2,

R is selected from the group consisting of halogen, $C_1$-$C_4$-alkyl and $C_1$-$C_4$-alkoxy, $R_p$ is selected from the group consisting of hydrogen, $C_1$-$C_4$-alkyl, X is selected from the group consisting of $CR^7R^8$, O, S, and N—$R^9$, Y is $CR^7R^8$ or O, $R^1$ is hydrogen or $C_1$-$C_4$-alkyl, $R^2$ is selected from the group consisting of
hydrogen, halogen, —C(O)—N($C_1$-$C_4$-alkyl)$_2$;
—$NR^{12}R^{13}$;
—$OR^{14}$;
—$SR^{15}$, —S(O)$R^{15}$, —SO$_2R^{15}$;
$C_1$-$C_4$-alkyl, $C_3$-$C_6$-cycloalkyl, $C_2$-$C_4$-alkenyl or $C_3$-$C_6$-cycloalkenyl, each of which is optionally substituted by 1, 2, 3, 4 or 5 substituents independently selected from the group consisting of halogen, —OH, cyano, $C_1$-$C_4$-alkoxy-C(O)— and —C(O)—NH$_2$, $C_1$-$C_4$-alkoxy, —NH$_2$, —N($C_1$-$C_4$-alkyl)$_2$, —N($C_1$-$C_4$-alkyl)(C(O)—$C_1$-$C_4$-alkyl); and
a monocyclic or a bicyclic heterocycle selected from the group consisting of 4- to 10-membered heterocycloalkyl, heterospirocycloalkyl, 5-membered heteroaryl, and 6-membered heteroaryl, each of which is optionally substituted by 1, 2, 3 or 4 substituents independently selected from the group consisting of halogen, —OH, oxo, —COOH, $C_1$-$C_4$-alkoxy-C(O)—, —C(O)—NH$_2$, $C_1$-$C_4$-alkyl, $C_1$-$C_4$-alkyl-C(O)—, $C_1$-$C_4$-halogenoalkyl having 1 to 5 halogen atoms, hydroxy-$C_1$-$C_4$-alkyl-, $C_1$-$C_4$-alkoxy-$C_1$-$C_4$-alkyl-, —NH$_2$, —N($C_1$-$C_4$-alkyl)$_2$, and 4- to 10-membered heterocycloalkyl, $R^3$ is hydrogen or $C_1$-$C_4$-alkyl, $R^4$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH$_2$, preferably hydrogen and halogen, more preferably fluorine and chlorine, $R^5$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $R^6$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $R^7$ is selected from the group consisting of hydrogen and $C_1$-$C_4$-alkyl, $R^8$ is selected from the group consisting of hydrogen and $C_1$-$C_4$-alkyl, or $R^7$ and $R^8$ together form an oxo group (=O), $R^9$ is $C_1$-$C_4$-alkyl, $R^{10}$ is selected from the group consisting of hydrogen, —OH and $C_1$-$C_4$-alkyl, $R^{11}$ is hydrogen, $R^{12}$ and $R^{13}$ are independently selected from the group consisting of
hydrogen, —NH(—C(O)—$C_1$-$C_4$-alkyl), $C_1$-$C_4$-alkoxy;
$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, —COOH, $C_1$-$C_4$-alkoxy-C(O)—, —C(O)—NH$_2$, —C(O)—N($C_1$-$C_4$-alkyl)$_2$, —NH—C(O)—$C_1$-$C_4$-alkyl, $C_1$-$C_4$-alkyl, $C_1$-$C_4$-alkoxy, $C_3$-$C_6$-cycloalkyl, —NH$_2$, —N($C_1$-$C_4$-alkyl)$_2$, —S—$C_1$-$C_4$-alkyl, —S(O)—$C_1$-$C_4$-alkyl, —SO$_2$-$C_1$-$C_4$-alkyl, and ($C_1$-$C_4$-alkoxy)$_2$P(=O)—;
heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms and $C_1$-$C_4$-alkoxy;
phenyl and benzo-$C_5$-$C_6$-cycloalkyl, each of which is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms; and
a monocyclic or a bicyclic heterocycle selected from the group of 4- to 10-membered heterocycloalkyl, 5-membered heteroaryl and 6-membered heteroaryl each of which is optionally substituted by 1, 2 or 3 substituents independently selected from the group consisting of halogen, —OH, oxo, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $R^{14}$ is selected from the group consisting of
$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, $C_1$-$C_4$-alkyl, $C_1$-$C_4$-alkoxy and $C_3$-$C_6$-cycloalkyl; and
4- to 10-membered heterocycloalkyl, $R^{15}$ is selected from the group consisting of
hydrogen;
$C_1$-$C_4$-alkyl, which is optionally substituted by 1, 2 or 3 substituents independently selected from the group consisting of —OH and —COOH; and
a 6-membered heteroaryl, Q is a substituted phenyl ring of the formula (Q1)

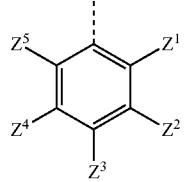
(Q1)

in which:

$Z^1$ and $Z^5$ are independently selected from the group consisting of hydrogen, halogen, $C_1$-$C_4$-alkyl, $C_1$-$C_4$-alkoxy, $C_1$-$C_4$-halogenoalkyl having 1 to 5 halogen atoms $Z^2$ and $Z^4$ are independently selected from the group consisting of hydrogen, halogen, cyano, —OH, $C_1$-$C_4$-alkyl, $C_1$-$C_4$-alkoxy, —NH($C_1$-$C_4$-alkyl), —N($C_1$-$C_4$-alkyl)$_2$, $C_1$-$C_4$-halogenoalkyl having 1 to 5 halogen atoms, $C_1$-$C_4$-halogenoalkoxy having 1 to 5 halogen atoms, —S—($C_1$-$C_4$-alkyl) S—($C_1$-$C_4$-halogenoalkyl) having 1 to 5 halogen atoms, and a 4- to 6-membered heterocycloalkyl, and $Z^3$ is selected from the group consisting of hydrogen, halogen, $C_1$-$C_4$-alkyl, $C_1$-$C_4$-alkoxy, $C_1$-$C_4$-halogenoalkoxy having 1 to 5 halogen atoms, and —N($C_1$-$C_4$-alkyl)$_2$, or $Z^1$ and $Z^2$ form, together with the carbon atoms that they are connected to, a 5-membered heterocycloalkyl or a 5-membered heteroaryl, each of which may be optionally substituted with one or two substituents selected from the group consisting of methyl, fluorine and oxo, $Z^3$ and $Z^5$ are hydrogen, and $Z^4$ is selected from the group consisting of hydrogen and $C_1$-$C_4$-alkoxy-C(O)—, and stereoisomers, tautomers, N-oxides, hydrates, solvates, and salts thereof, and mixtures of same.

In accordance with a fifth embodiment of the first aspect, the present invention covers compounds of general formula (I), supra, in which:

A is selected from the group consisting of

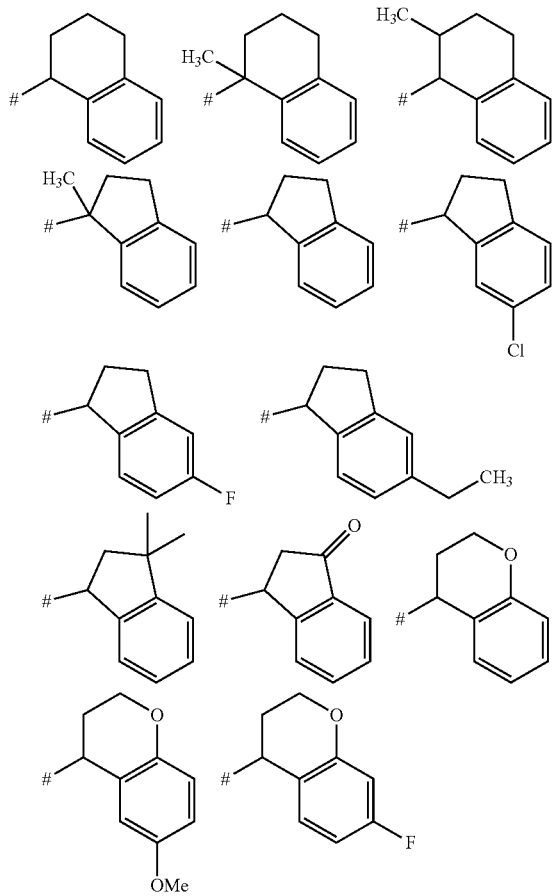
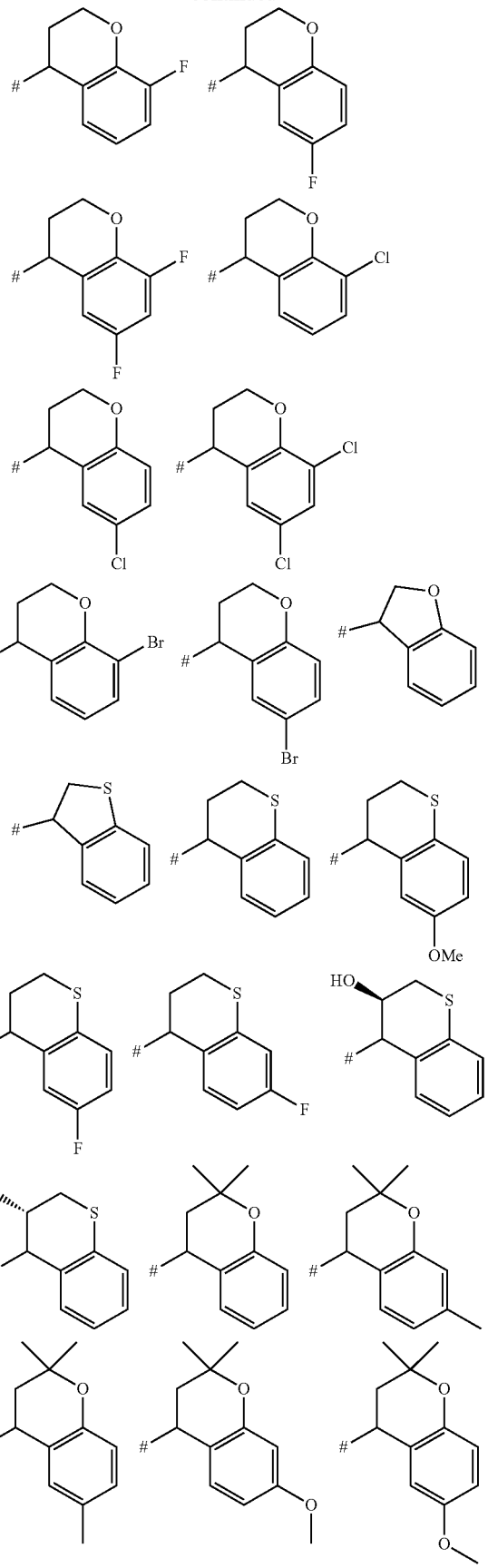

-continued

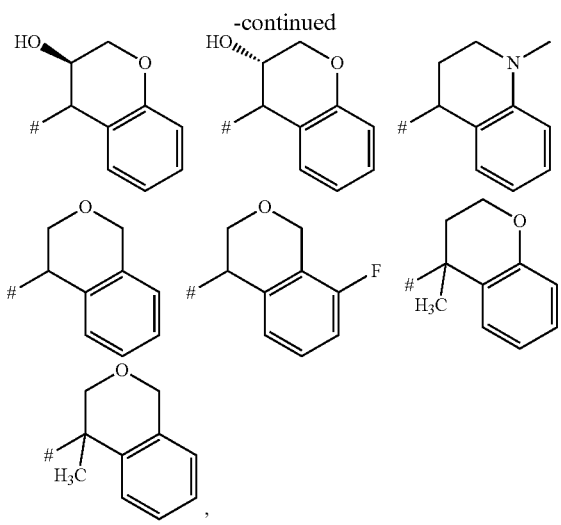

R¹ is hydrogen or methyl,
R² is selected from the group consisting of
  hydrogen, chlorine, iodine, —C(O)—N(CH₃)₂,
    —NR¹²R¹³;
  —OR¹⁴;
  —SR¹⁵, —S(O)R¹⁵, —SO₂R¹⁵;
  methyl, ethyl, propyl, isopropyl, cyclopropyl, cyclobutyl, cyclopentyl, cyclohexyl, ethenyl, propenyl, cyclopentenyl, cyclohexenyl, each of which is optionally substituted by 1 or 2 substituents independently selected from the group consisting of —OH, cyano, ethoxy-C(O)—, —C(O)—NH₂, methoxy, NH₂, N(CH₃)₂, N(CH₃)(C(O)CH₃); and
  a monocyclic or a bicyclic heterocycle selected from the group consisting of azetidine, oxetane, pyrrolidine, tetrahydrofurane, pyrazolidine, imidazolidine, 1,2,4-triazolidine, piperidine, piperazine, tetrahydropyrane, tetrahydropyridine, dihydro-2H-pyrane, 1,2-oxazolidine, 1,2-oxazine, morpholine, thiomorpholine, 3,4-dihydroisoquinoline, 2,3-dihydro-indole, 1,3-dihydro-isoindoel, 3,9-dioxa-7-azabicyclo[3.3.1]nonane, 6-oxa-3-azabicyclo[3.1.1]heptane, 8-oxa-3-azabicyclo[3.2.1]octane, thiophene, imidazole, pyrazole, 1,2,4-triazole, 1,2,3-triazole, 1,2,3,4-tetrazole, pyridine, dihydropyridine, pyrimidine, tetrahydropyrimidine, 4-oxa-7-azaspiro[2.5]octane, each of which is optionally substituted by 1, 2, 3 or 4 substituents independently selected from the group consisting of fluorine, chlorine, cyano, —OH, oxo, —COOH, methoxy-C(O)—, ethoxy-C(O)—, tert-butoxy-C(O)—, —C(O)—NH₂, methyl, methyl-C(O)—, difluoromethyl, trifluoromethyl, hydroxymethyl-, methoxymethyl-, —NH₂, —NMe₂, pyrrolidine,
R³ is hydrogen or methyl,
R⁴ is selected from the group consisting of hydrogen, fluorine, chlorine, —OH, cyano, methyl, methoxy, trifluoromethyl, trifluoromethoxy and NH₂, preferably hydrogen, fluorine and chlorine,
R⁵ is selected from the group consisting of hydrogen, fluorine, chlorine, —OH, cyano, methyl, methoxy and trifluoromethyl,
R⁶ is selected from the group consisting of hydrogen, fluorine, chlorine, —OH, cyano, methyl and methoxy, R¹² and R¹³ are independently selected from the group consisting of
  hydrogen, —NH(—C(O)-methyl), methoxy;
  methyl, ethyl, propyl, isopropyl, butyl, isobutyl, cyclopropyl, cyclobutyl, benzyl, 1-phenylethyl, each of which is optionally substituted by 1, 2 or 3 substituents independently selected from the group consisting of fluorine, —OH, —COOH, methoxy-C(O)—, ethoxy-C(O)—, tert-butoxy-C(O)—, —C(O)—NH₂, —C(O)—NMe₂, —NH—C(O)-methyl, methyl, methoxy, cyclopropyl, —NH₂, NMe₂, S-methyl, S(O)-methyl, SO₂-methyl, and (EtO)₂P(=O)—;
  heterocyclyl-methyl, heterocyclyl-ethyl, wherein the heterocyclyl substituent is selected from the group consisting of oxetane, tetrahydrofurane, tetrahydropyrane pyrrolidine, morpholine, pyrazole, imidazole, 1,2,4-oxadiazole, pyridine, each of which is optionally substituted by 1 substituent independently selected from the group consisting of fluorine, chlorine, —OH, oxo and methyl;
  phenyl;
  2,3-dihydro-1H-indene, and
  a monocyclic or a bicyclic heterocycle selected from the group of oxetane, thietane, pyrrolidine, morpholine, tetrahydropyrane, pyridine and pyrazole, each of which is optionally substituted by 1 or 2 substituents independently selected from the group consisting of fluorine, chlorine, —OH, oxo, methyl;
R¹⁴ is selected from the group consisting of
  methyl, ethyl, isopropyl, butyl, cyclopentyl, benzyl, each of which is optionally substituted by 1 or 2 substituents independently selected from the group consisting of fluorine, —OH, methyl, methoxy and cyclopentyl; and
  a monocyclic or a bicyclic heterocycle selected from the group consisting of pyrrolidin and tetrahydropyran,
R¹⁵ is selected from the group consisting of
  methyl and ethyl, each of which is optionally substituted by 1 substituent independently selected from the group consisting of —OH and —COOH; and
  pyridine,
Q is a substituted phenyl ring of the formula (Q1)

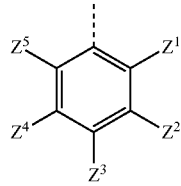

(Q1)

in which:
Z¹ and Z⁵ are independently selected from the group consisting of hydrogen, fluorine, chlorine, methyl, trifluoromethyl and methoxy,
Z² and Z⁴ are independently selected from the group consisting of hydrogen, fluorine, chlorine, —OH, cyano, methyl, ethyl, tert-butyl, —NHMe, —NMe₂, trifluoromethyl, methoxy, trifluoromethoxy, —SMe, 2,2,2-trifluoroethyl)sulfanyl and morpholinyl, and
Z³ is independently selected from the group consisting of hydrogen, fluorine, chlorine, methyl, methoxy, difluoromethoxy and —NMe₂, and stereoisomers, tautomers, N-oxides, hydrates, solvates, and salts thereof, and mixtures of same.

In accordance with a sixth embodiment of the first aspect, the present invention covers compounds of general formula (I), supra, in which:

A is selected from the group consisting of

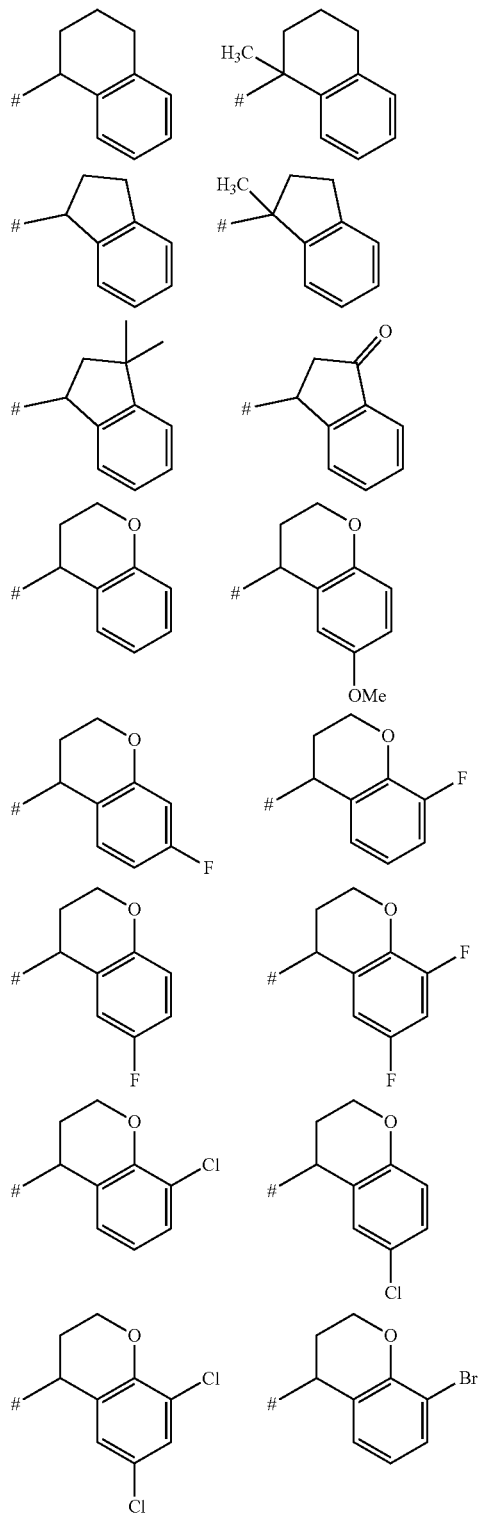

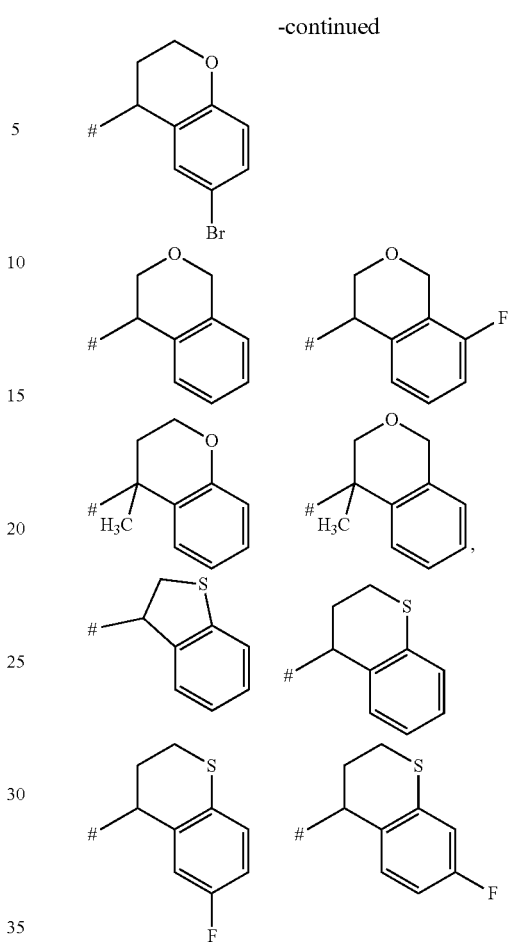

$R^1$ is hydrogen or methyl,
$R^2$ is selected from the group consisting of
  chlorine, iodine, —C(O)—N(CH$_3$)$_2$,
  —NR$^{12}$R$^{13}$;
  —OR$^{14}$;
  —SR$^{15}$, —S(O)R$^{15}$, —SO$_2$R$^{15}$;
  methyl, ethyl, propyl, isopropyl, cyclopropyl, cyclobutyl, cyclopentyl, ethenyl, propenyl, each of which is optionally substituted by 1 or 2 substituents independently selected from the group consisting of —OH, cyano, ethoxy-C(O)—, —C(O)—NH$_2$, methoxy, NH$_2$, N(CH$_3$)$_2$, N(CH$_3$)(C(O)CH$_3$); and
  a monocyclic or a bicyclic heterocycle selected from the group consisting of azetidine, oxetane, pyrrolidine, tetrahydrofurane, pyrazolidine, imidazolidine, 1,2,4-triazolidine, piperidine, piperazine, tetrahydropyrane, dihydro-2H-pyrane, 1,2-oxazolidine, morpholine, thiomorpholine, 3,4-dihydroisoquinoline, 2,3-dihydro-indoel, 1,3-dihydro-isoindole, 3,9-dioxa-7-azabicyclo[3.3.1]nonane, 6-oxa-3-azabicyclo[3.1.1]heptane, 8-oxa-3-azabicyclo[3.2.1]octane, thiophene, imidazole, pyrazole, 1,2,3-triazole, 1,2,3,4-tetrazole, pyridine, dihydropyridine, pyrimidine, tetrahydropyrimidine, each of which is optionally substituted by 1, 2, 3 or 4 substituents independently selected from the group consisting of fluorine, —OH, oxo, —COOH, methoxy-C(O)—, ethoxy-C(O)—, tert-butoxy-C(O)—, —C(O)—NH$_2$, methyl, methyl-C(O)—, difluoromethyl, trifluoromethyl, hydroxymethyl-, methoxymethyl-, —NH$_2$, —NMe$_2$, pyrrolidine, R³ is hydrogen or methyl,
R⁴ is selected from the group consisting of hydrogen, chlorine, fluorine, methyl, methoxy and trifluoromethyl, preferably hydrogen, fluorine and chlorine,
R⁵ is selected from the group consisting of hydrogen, chlorine, fluorine, —OH, cyano, methyl, trifluoromethoxy and NH₂,
R⁶ is selected from the group consisting of hydrogen, fluorine, chlorine, —OH, cyano, methyl and methoxy,
R¹² and R¹³ are independently selected from the group consisting of
  hydrogen, —NH(—C(O)-methyl), methoxy;
  methyl, ethyl, propyl, isopropyl, butyl, isobutyl, cyclopropyl, cyclobutyl, benzyl, 1-phenylethyl, each of which is optionally substituted by 1, 2 or 3 substituents independently selected from the group consisting of fluorine, —OH, —COOH, methoxy-C(O)—, ethoxy-C(O)—, tert-butoxy-C(O)—, —C(O)—NH₂, —C(O)—NMe₂, —NH—C(O)-methyl, methyl, methoxy, cyclopropyl, —NH₂, —NMe₂, SO₂-methyl and (EtO)₂P(=O)—;
  heterocyclyl-methyl, heterocyclyl-ethyl, wherein the heterocycyl substituent is selected from the group consisting of oxetane, tetrahydrofurane, tetrahydropyrane, pyrrolidine, pyrazole, imidazole, 1,2,4-oxadiazole, morpholine, pyridine, each of which is optionally substituted by 1 substituent independently selected from the group consisting of oxo and methyl;
  phenyl;
  2,3-dihydro-1H-indene, and
  a monocyclic or a bicyclic heterocycle selected from the group of oxetane, morpholine, tetrahydropyrane, pyridine and pyrazole;
R¹⁴ is selected from the group consisting of
  methyl, ethyl, isopropyl, butyl, cyclopentyl, benzyl, each of which is optionally substituted by 1 or 2 substituents independently selected from the group consisting of fluorine, —OH, methyl, methoxy and cyclopentyl; and
  a monocyclic or a bicyclic heterocycle selected from the group consisting of pyrrolidin and tetrahydropyran,
R¹⁵ is selected from the group consisting of
  methyl and ethyl, each of which is optionally substituted by 1 substituent independently selected from the group consisting of —OH and —COOH; and
  pyridine,
Q is a substituted phenyl ring of the formula (Q1)

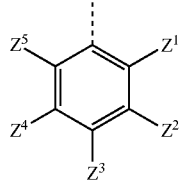

(Q1)

in which:
Z¹ and Z⁵ are independently selected from the group consisting of hydrogen, fluorine, chlorine, methyl, methoxy and trifluoromethyl,
Z² and Z⁴ are independently selected from the group consisting of hydrogen, fluorine, chlorine, —OH, cyano, methyl, ethyl, tert-butyl, —NHMe, —NMe₂, trifluoromethyl, methoxy, trifluoromethoxy, —SMe, 2,2,2-trifluoroethyl)sulfanyl and morpholinyl, and
Z³ is independently selected from the group consisting of hydrogen, fluorine, chlorine, methyl, methoxy, difluoromethoxy and —NMe₂, and stereoisomers, tautomers, N-oxides, hydrates, solvates, and salts thereof, and mixtures of same.

In accordance with a seventh embodiment of the first aspect, the present invention covers compounds of general formula (I), supra, in which:

A is selected from the group consisting of

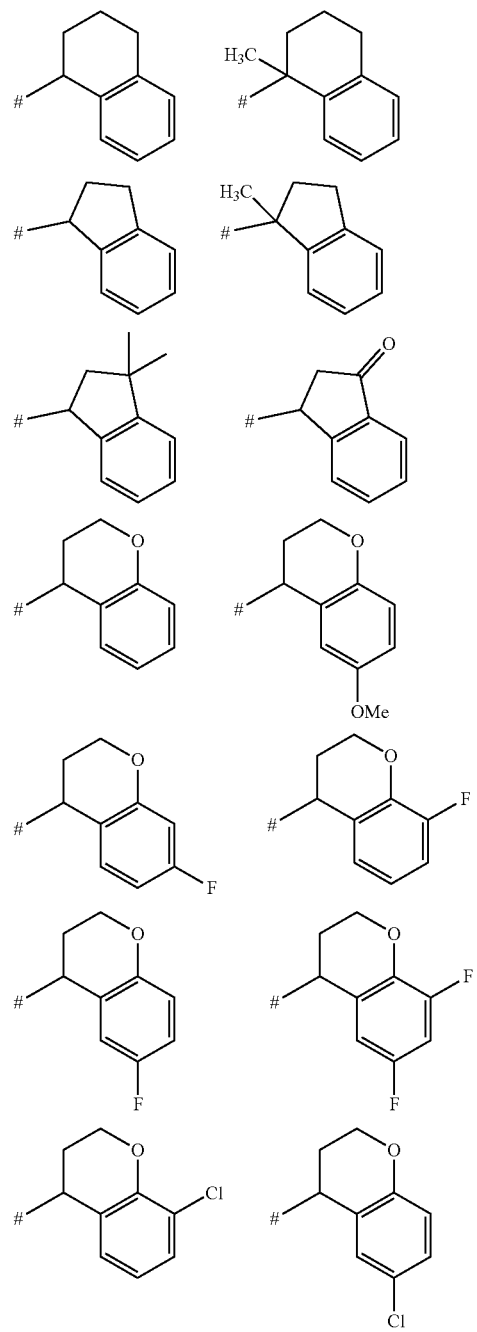

-continued

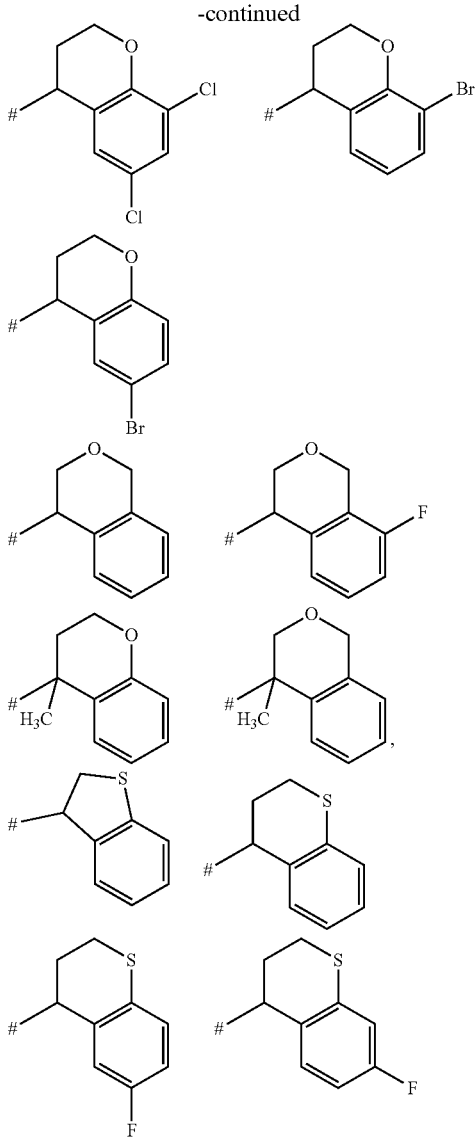

R[1] is hydrogen or methyl,
R[2] is selected from the group consisting of hydrogen, (2-amino-2-oxoethyl)amino, (2-aminoethyl)amino, (2-hydroxyethyl)amino, hydroxymethyl, methoxymethyl, 2-hydroxyethyl, (2-hydroxyethyl)oxy, (2-methoxy-2-oxoethyl)amino, (3-methoxy-3-oxopropyl)-methylamino, (2-methoxyethyl)(methyl)amino, (2-methoxyethyl)amino, (2-methoxyethyl)oxy, (2R, 6S)-2,6-dimethylmorpholin-4-yl, 2-(trifluoromethyl)morpholin-4-yl, (2S)-2-methylmorpholin-4-yl, 2,2-difluoroethyl(methyl)amino, (3,3,3-trifluoropropyl)amino, (3-methoxybenzyl)oxy, (3rac,4rac)-3-amino-4-fluoropyrrolidin-1-yl, (3S)-3-(hydroxymethyl)pyrrolidin-1-yl, (carboxyethyl)amino, (cyclopentylmethyl)oxy, (pyridin-2-ylmethyl)amino, (rac)-3-hydroxypyrrolidin-1-yl, [2-(dimethylamino)ethyl]amino, 1,1-dioxidothiomorpholin-4-yl, 1,2-oxazolidin-2-yl, 1H-1,2,3-triazol-1-yl, 1H-imidazol-1-yl, 1H-pyrazol-1-yl, 1H-pyrazol-4-yl, 2,2-dimethylmorpholin-4-yl, 2,2-dimethylpyrrolidin-1-yl, 2,4-dimethyl-3,5-dioxo-1,2,4-triazolidin-1-yl, 2-amino-2-oxoethyl, 2H-1,2,3-triazol-2-yl, 1H-tetrazol-5-yl, 3-(pyrrolidin-1-yl)azetidin-1-yl, 3,3-difluoroazetidin-1-yl, 3,3-difluoropyrrolidin-1-yl, 3-fluoroazetidin-1-yl, 3-hydroxyazetidin-1-yl, 3-methylazetidin-1-yl, 3-oxopyrazolidin-1-yl, 1-(difluoromethyl)-1H-pyrazol-4-yl, 4-(trifluoromethyl)-1H-pyrazol-1-yl, 1-methyl-piperidin-4-yl, 4-fluoropiperidin-1-yl, 4,4-difluoropiperidin-1-yl, 4-oxoimidazolidin-1-yl, amino, anilino, azetidin-1-yl, benzyl(methyl)amino, chlorine, iodine, cyanomethyl, cyclobutyl(methyl)amino, cyclopentyloxy, cyclopropyl, cyclobutyl, cyclopentyl, cyclopropyl(ethyl)amino, cyclopropyl(methyl)amino, cyclopropylamino, diethylamino, dimethylamino, dimethylaminocarbonyl, aminomethyl, 2-aminoethyl, (dimethylamino)methyl, 2-(dimethylamino)ethyl, ethenyl, ethyl, ethylamino, ethyloxy, ethylsulfanyl, ethylsulfinyl, ethylsulfonyl, isopropyl, isopropyloxy, methoxyamino, methyl, methyl(2,2,2-trifluoroethyl)amino, oxetan-3-ylmethylamino, methyl(oxetan-3-yl)amino, methylamino, methyloxy, methylsulfanyl, morpholin-4-yl, morpholin-4-ylamino, nitrilomethyl, prop-1-en-2-yl, propyl, propylamino, pyridin-4-yloxetan-3-yl, tetrahydrofuran-3-yl, 3,6-dihydro-2H-pyran-4-yl, tetrahydropyran-4-yl, tetrahydro-2H-pyran-4-yloxy, 3-thienyl and thiomorpholin-4-yl,
R[3] is hydrogen or methyl,
R[4] is selected from the group consisting of hydrogen, chlorine, fluorine, —OH, cyano, methyl, methoxy, trifluoromethyl, trifluoromethoxy and NH$_2$, preferably hydrogen, fluorine and chlorine,
R[5] is selected from the group consisting of hydrogen, chlorine, fluorine, —OH, cyano, methyl, methoxy and trifluoromethyl,
R[6] is selected from the group consisting of hydrogen, fluorine, chlorine, —OH, cyano, methyl and methoxy,
Q is selected from the group consisting of phenyl, 2,5-bis(trifluoromethyl)phenyl, 2,3,4-trifluorophenyl, 2,3,5-trichlorophenyl, 2,3,5-trifluorophenyl, 2,3,6-trifluorophenyl, 2,3-dichlorophenyl, 2,3-dichloro-5-cyanophenyl, 2,3-dichloro-5-hydroxyphenyl, 2,3-difluorophenyl, 2,4,5-trifluorophenyl, 2,4,6-trifluoro-3-methoxyphenyl, 2,4-difluoro-3-hydroxyphenyl, 2,4-difluoro-3-methoxyphenyl, 2,5-dichlorophenyl, 2-chloro-5-cyanophenyl, 2-chloro-5-methylphenyl, 2,5-difluoro-4-methoxyphenyl, 2,6-difluorophenyl, 2-chloro-3-fluorophenyl, 2-chloro-4-(dimethylamino)phenyl, 2-chloro-4-fluorophenyl, 2-chloro-5-fluorophenyl, 2-chloro-6-fluorophenyl, 2-chlorophenyl, 3,5-difluoropyridin-4-yl, 2-chloro-3-fluoropyridin-4-yl, 2-fluoro-5-methylphenyl, 3-fluoro-5-methylphenyl, 2-fluoro-3-(trifluoromethoxy)phenyl, 2-fluoro-3-(trifluoromethyl)phenyl, 5-fluoro-2-(trifluoromethyl)phenyl, 3-cyano-5-methylphenyl, 3-(trifluoromethyly)phenyl, 3-(trifluoromethoxy)phenyl, 3,4,5-trifluorophenyl, 3,4-dichlorophenyl, 3,4-difluoro-2-methoxyphenyl, 3,4-difluorophenyl, 3,5-dichloro-4-(dimethylamino)phenyl, 3,5-dichloro-4-fluorophenyl, 3,5-dichlorophenyl, 3,5-difluorophenyl, 4-(difluoromethoxy)-3,5-difluorophenyl, 2,5-dimethylphenyl, 3,5-dimethylphenyl, 3-tert-butyl-5-methylphenyl, 5-tert-butyl-2-chloro-3-methylphenyl, 3-chloro-2-fluoro-5-methylphenyl, 3-chloro-2-fluorophenyl, 3-chloro-2-methylphenyl, 3-chloro-4-fluorophenyl, 3-chloro-4-methylphenyl, 2-chloro-3-(trifluoromethyl)phenyl, 2-methyl-5-(trifluoromethyl)phenyl, 3-chloro-5-(trifluoromethyl)phenyl, 3-chloro-5-ethylphenyl, 3-chloro-5-fluorophenyl, 3-chloro-5-methoxyphenyl, 3-chloro-5-methylphenyl, 3-chlorophenyl, 3-fluoro-2-methylphenyl, 3-fluoro-4- methoxyphenyl, 3-fluoro-5-methylphenyl, 4-fluoro-3-methoxyphenyl, 5-chloro-2,4-difluorophenyl, 5-chloro-2-fluoro-3-methylphenyl, 5-chloro-2-fluoro-4-methylphenyl, 5-chloro-2-fluorophenyl, 5-chloro-2-methoxyphenyl, 5-fluoro-2-methylphenyl, 5-fluoro-2-methoxyphenyl, 3,5-diethylphenyl, 2-chloro-3,5-diethylphenyl, 3-chloro-2-thienyl, 4-chloro-2-thienyl, 5-chloro-2-thienyl, 2,5-dichloro-3-thienyl, 5-fluoro-2-thienyl, 5-cyano-2-thienyl, 5-cyano-4-methyl-2-thienyl, 5-methyl-2-thienyl, 2,5-dimethyl-3-thienyl, 5-(trifluoromethyl)-2-thienyl 3-tert-butyl-5-fluorophenyl, and 3-tert-butyl-5-chlorophenyl and stereoisomers, tautomers, N-oxides, hydrates, solvates, and salts thereof, and mixtures of same.

In accordance with an eighth embodiment of the first aspect, the present invention covers compounds of general formula (I), supra, in which:

A is A3 or A4

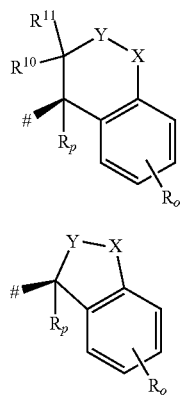

o is 0 or 1,

R is selected from the group consisting of halogen, $C_1$-$C_4$-alkyl and $C_1$-$C_4$-alkoxy, $R_p$ is selected from the group consisting of hydrogen, $C_1$-$C_4$-alkyl, X is selected from the group consisting of $CR^7R^8$, O, S, and N—$R^9$, Y is $CR^7R^8$ or O, $R^1$ is hydrogen or $C_1$-$C_4$-alkyl, $R^2$ is selected from the group consisting of
hydrogen, halogen, —C(O)—N($C_1$-$C_4$-alkyl)$_2$; —N$R^{12}R^{13}$;
—O$R^{14}$;
—S$R^{15}$, —S(O)$R^{15}$, —SO$_2R^{15}$;
$C_1$-$C_4$-alkyl, $C_3$-$C_6$-cycloalkyl, $C_2$-$C_4$-alkenyl or $C_3$-$C_6$-cycloalkenyl, each of which is optionally substituted by 1, 2, 3, 4 or 5 substituents independently selected from the group consisting of halogen, —OH, cyano, $C_1$-$C_4$-alkoxy-C(O)— and —C(O)—NH$_2C_1$-$C_4$-alkoxy, —NH$_2$, —N($C_1$-$C_4$-alkyl)$_2$, —N($C_1$-$C_4$-alkyl)(C(O)—$C_1$-$C_4$-alkyl), and a monocyclic or a bicyclic heterocycle selected from the group consisting of 4- to 10-membered heterocycloalkyl, heterospirocycloalkyl, 5-membered heteroaryl, and 6-membered heteroaryl, each of which is optionally substituted by 1, 2, 3 or 4 substituents independently selected from the group consisting of halogen, —OH, oxo, —COOH, $C_1$-$C_4$-alkoxy-C(O)—, —C(O)—NH$_2$, $C_1$-$C_4$-alkyl, $C_1$-$C_4$-alkyl-C(O)—, $C_1$-$C_4$-halogenoalkyl having 1 to 5 halogen atoms, hydroxy-$C_1$-$C_4$-alkyl-, $C_1$-$C_4$-alkoxy-$C_1$-$C_4$-alkyl-, —NH$_2$, —N($C_1$-$C_4$-alkyl)$_2$, and 4- to 10-membered heterocycloalkyl, $R^3$ is hydrogen or $C_1$-$C_4$-alkyl, $R^4$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, NH$_2$, preferably hydrogen and halogen, more preferably fluorine and chlorine, $R^5$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $R^6$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $R^7$ is selected from the group consisting of hydrogen and $C_1$-$C_4$-alkyl, $R^8$ is selected from the group consisting of hydrogen and $C_1$-$C_4$-alkyl, or $R^7$ and $R^8$ together form an oxo group (=O), $R^9$ is $C_1$-$C_4$-alkyl, $R^{10}$ is selected from the group consisting of hydrogen, —OH and $C_1$-$C_4$-alkyl, $R^{11}$ is hydrogen, $R^{12}$ and $R^{13}$ are independently selected from the group consisting of
hydrogen, —NH(—C(O)—$C_1$-$C_4$-alkyl), $C_1$-$C_4$-alkoxy;
$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, —COOH, $C_1$-$C_4$-alkoxy-C(O)—, —C(O)—NH$_2$, —C(O)—N($C_1$-$C_4$-alkyl)$_2$, —NH—C(O)—$C_1$-$C_4$-alkyl, $C_1$-$C_4$-alkyl, $C_1$-$C_4$-alkoxy, $C_3$-$C_6$-cycloalkyl, —NH$_2$, —N($C_1$-$C_4$-alkyl)$_2$, —S—$C_1$-$C_4$-alkyl, —S(O)—$C_1$-$C_4$-alkyl, —SO$_2$-$C_1$-$C_4$-alkyl, and ($C_1$-$C_4$-alkoxy)$_2$P(=O)—;
heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms and $C_1$-$C_4$-alkoxy;
phenyl and benzo-$C_5$-$C_6$-cycloalkyl, each of which is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms; and a monocyclic or a bicyclic heterocycle selected from the group of 4- to 10-membered heterocycloalkyl, 5-membered heteroaryl and 6-membered heteroaryl each of which is optionally substituted by 1, 2 or 3 substituents independently selected from the group consisting of halogen, —OH, oxo, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $R^{14}$ is selected from the group consisting of
  $C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, $C_1$-$C_4$-alkyl, $C_1$-$C_4$-alkoxy and $C_3$-$C_6$-cycloalkyl; and
  4- to 10-membered heterocycloalkyl,
$R^{15}$ is selected from the group consisting of
  hydrogen;
  $C_1$-$C_4$-alkyl, which is optionally substituted by 1, 2 or 3 substituents independently selected from the group consisting of —OH and —COOH; and
  a 6-membered heteroaryl,
Q is a substituted phenyl ring of the formula (Q1)

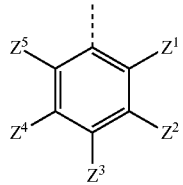

(Q1)

in which:
$Z^1$ and $Z^5$ are independently selected from the group consisting of hydrogen, halogen, $C_1$-$C_4$-alkyl, $C_1$-$C_4$-alkoxy and $C_1$-$C_4$-halogenoalkyl having 1 to 5 halogen atoms,
$Z^2$ and $Z^4$ are independently selected from the group consisting of hydrogen, halogen, cyano, —OH, $C_1$-$C_4$-alkyl, $C_1$-$C_4$-alkoxy, —NH($C_1$-$C_4$-alkyl), —N($C_1$-$C_4$-alkyl)$_2$, $C_1$-$C_4$-halogenoalkyl having 1 to 5 halogen atoms, $C_1$-$C_4$-halogenoalkoxy having 1 to 5 halogen atoms, —S—($C_1$-$C_4$-alkyl), S—($C_1$-$C_4$-halogenoalkyl) having 1 to 5 halogen atoms and a 4- to 6-membered heterocycloalkyl, and
$Z^3$ is selected from the group consisting of hydrogen, halogen, $C_1$-$C_4$-alkyl, $C_1$-$C_4$-alkoxy, $C_1$-$C_4$-halogenoalkoxy having 1 to 5 halogen atoms and —N($C_1$-$C_4$-alkyl)$_2$, or
$Z^1$ and $Z^2$ form, together with the carbon atoms that they are connected to, a 5-membered heterocycloalkyl or a 5-membered heteroaryl, each of which may be optionally substituted with one or two substituents selected from the group consisting of methyl, fluorine and oxo,
$Z^3$ and $Z^5$ are hydrogen, and
$Z^4$ is selected from the group consisting of hydrogen and $C_1$-$C_4$-alkoxy-C(O)—, or
Q is a pyridine ring of the formula (Q4)

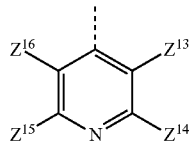

(Q4)

in which:
$Z^3$, $Z^{14}$, $Z^{15}$ and $Z^{16}$ are independently selected from the group consisting of hydrogen, halogen, cyano, $C_1$-$C_4$-alkyl, $C_1$-$C_4$-alkoxy, $C_1$-$C_4$-hydroxyalkyl, NH$_2$, —NH($C_1$-$C_4$-alkyl), —N($C_1$-$C_4$-alkyl)$_2$, —NH—CO—$C_1$-$C_4$-alkyl, and monocyclic heterocycles selected from the group of 4- to 7-membered heterocycloalkyl or 5-membered heteroaryls having at least one nitrogen atom via which the heteroaryl ring is connected to the pyridine ring, each of which is optionally substituted with 1, 2 or 3 substituents independently selected from the group consisting of halogen, cyano, nitro, —OH, oxo, thiono, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, —S—($C_1$-$C_4$-halogenoalkyl) having 1 to 5 halogen atoms, —S(O)—($C_1$-$C_4$-halogenoalkyl) having 1 to 5 halogen atoms, —SO$_2$—($C_1$-$C_4$-halogenoalkyl) having 1 to 5 halogen atoms, or
Q is a pyridine ring of the formula (Q5)

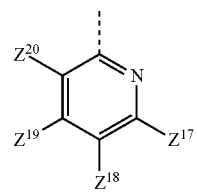

(Q5)

in which:
$Z^{17}$, $Z^{18}$, and $Z^{19}$ are hydrogen, and
$Z^{20}$ is halogen, or
Q is a 5-membered aromatic heterocycle of the formula (Q6)

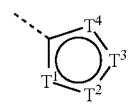

(Q6)

in which:
$T^1$-$T^4$ are independently selected from the group consisting of N, O, S, C—$Z^{21}$ and N—$Z^{22}$, wherein not more than one of $T^1$-$T^4$ is O, not more than one of $T^1$-$T^4$ is S, not more than one of $T^1$-$T^4$ is N—$Z^{22}$, and wherein
each $Z^{21}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and
each $Z^{22}$ is independently selected from the group consisting of hydrogen, $C_1$-$C_4$-alkyl, $C_1$-$C_4$-halogenoalkyl having 1 to 5 halogen atoms, $C_1$-$C_4$-alkyl-$C_3$-$C_6$-cycloalkyl, $C_1$-$C_4$-alkoxy-$C_1$-$C_4$-alkyl, or
Q is a 5-membered aromatic heterocycle of the formula (Q7)

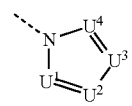

(Q7)

in which:

U$^1$-U$^4$ are independently selected from the group consisting of N and C—Z$^{23}$, wherein not more than three of U$^1$-U$^4$ are N, and wherein each Z$^{23}$ is independently selected from the group consisting of hydrogen, halogen, cyano, C$_1$-C$_4$-alkyl, C$_1$-C$_4$-halogenoalkyl having 1 to 5 halogen atoms, C$_1$-C$_4$-alkoxy, and stereoisomers, tautomers, N-oxides, hydrates, solvates, and salts thereof, and mixtures of same.

Further Embodiments of the First Aspect of the Present Invention

In a further embodiment of the first aspect, the present invention covers compounds of formula (I), supra, in which:

A is A1 or A2,

A1

A2 o is 0, 1 or 2,

R is selected from the group consisting of halogen, C$_1$-C$_4$-alkyl and C$_1$-C$_4$-alkoxy, cyano, C$_1$-C$_4$-halogenoalkyl having 1 to 5 halogen atoms, R$_p$ is selected from the group consisting of hydrogen, C$_1$-C$_4$-alkyl, X, Y are independently selected from the group consisting of CR$^7$R$^8$, O, S, and N—R$^9$, wherein at least one of X and Y is CR$^7$R$^8$, R$^7$ is selected from the group consisting of hydrogen and C$_1$-C$_4$-alkyl, R$^8$ is selected from the group consisting of hydrogen and C$_1$-C$_4$-alkyl, or R$^7$ and R$^8$ together form an oxo group (=O), R$^9$ is C$_1$-C$_4$-alkyl, R$^{10}$ is selected from the group consisting of hydrogen, —OH, C$_1$-C$_4$-alkyl and C$_1$-C$_4$-alkoxy, and R$^{11}$ is hydrogen, wherein when Y is O, S or N—R$^9$, R$^{10}$ is not —OH or C$_1$-C$_4$-alkoxy, and stereoisomers, tautomers, N-oxides, hydrates, solvates, and salts thereof, and mixtures of same.

In a further embodiment of the first aspect, the present invention covers compounds of formula (I), supra, in which:

A is A1 or A2,

A1

A2 o is 0, 1 or 2,

R is selected from the group consisting of halogen, C$_1$-C$_4$-alkyl and C$_1$-C$_4$-alkoxy, cyano, C$_1$-C$_4$-halogenoalkyl having 1 to 5 halogen atoms, R$_p$ is hydrogen, X, Y are independently selected from the group consisting of CR$^7$R$^8$, O, and S, wherein at least one of X and Y is CR$^7$R$^8$, R$^7$ is selected from the group consisting of hydrogen and C$_1$-C$_4$-alkyl, R$^8$ is selected from the group consisting of hydrogen and C$_1$-C$_4$-alkyl, or R$^7$ and R$^8$ together form an oxo group (=O), R$^{10}$ is selected from the group consisting of hydrogen, —OH, C$_1$-C$_4$-alkyl and C$_1$-C$_4$-alkoxy, and R$^{11}$ is hydrogen, wherein when Y is O, S or N—R$^9$, R$^{10}$ is not —OH, and stereoisomers, tautomers, N-oxides, hydrates, solvates, and salts thereof, and mixtures of same.

In a further embodiment of the first aspect, the present invention covers compounds of formula (I), supra, in which:

A is A1 or A2,

A1

A2 o is 0 or 1,

R is selected from the group consisting of halogen, C$_1$-C$_4$-alkyl and C$_1$-C$_4$-alkoxy, R$_p$ is selected from the group consisting of hydrogen, C$_1$-C$_4$-alkyl, X is selected from the group consisting of CR$^7$R$^8$, O, S, and N—R$^9$, Y is CR⁷R⁸ or O,
R⁷ is selected from the group consisting of hydrogen and C₁-C₄-alkyl,
R⁸ is selected from the group consisting of hydrogen and C₁-C₄-alkyl,
or R⁷ and R⁸ together form an oxo group (=O),
R⁹ is C₁-C₄-alkyl,
R¹⁰ is selected from the group consisting of hydrogen, —OH and C₁-C₄-alkyl, and
R¹¹ is hydrogen,
and stereoisomers, tautomers, N-oxides, hydrates, solvates, and salts thereof, and mixtures of same.

In a further embodiment of the first aspect, the present invention covers compounds of formula (I), supra, in which:

A is A1 or A2,

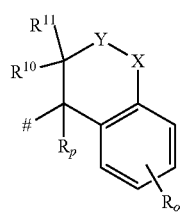

A1

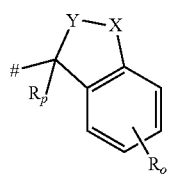

A2 o is 0 or 1,
R is selected from the group consisting of halogen, C₁-C₄-alkyl and C₁-C₄-alkoxy,
$R_p$ is hydrogen,
X is selected from the group consisting of CR⁷R⁸, O and S,
Y is CR⁷R⁸ or O,
R⁷ is selected from the group consisting of hydrogen and C₁-C₄-alkyl,
R⁸ is selected from the group consisting of hydrogen and C₁-C₄-alkyl,
or R⁷ and R⁸ together form an oxo group (=O),
R¹⁰ is selected from the group consisting of hydrogen, —OH and C₁-C₄-alkyl, and
R¹¹ is hydrogen,
and stereoisomers, tautomers, N-oxides, hydrates, solvates, and salts thereof, and mixtures of same.

In a further embodiment of the first aspect, the present invention covers compounds of formula (I), supra, in which:

A is selected from the group consisting of

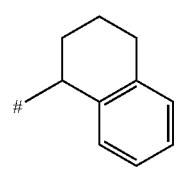 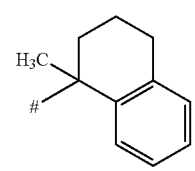

-continued

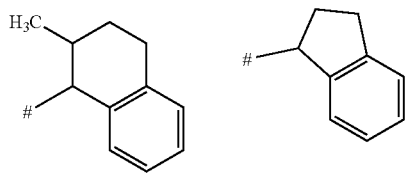

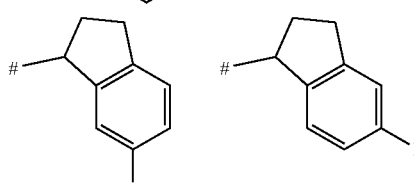

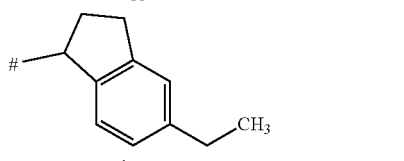

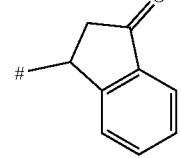

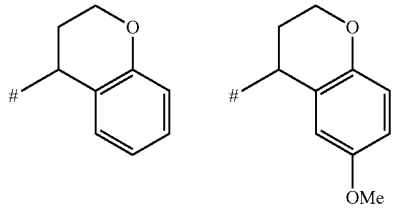

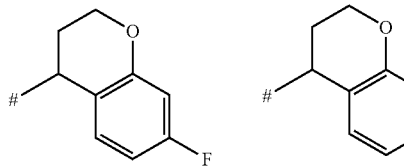

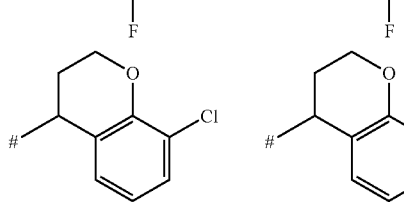

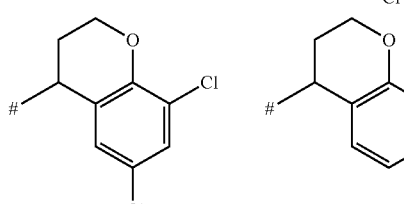

-continued

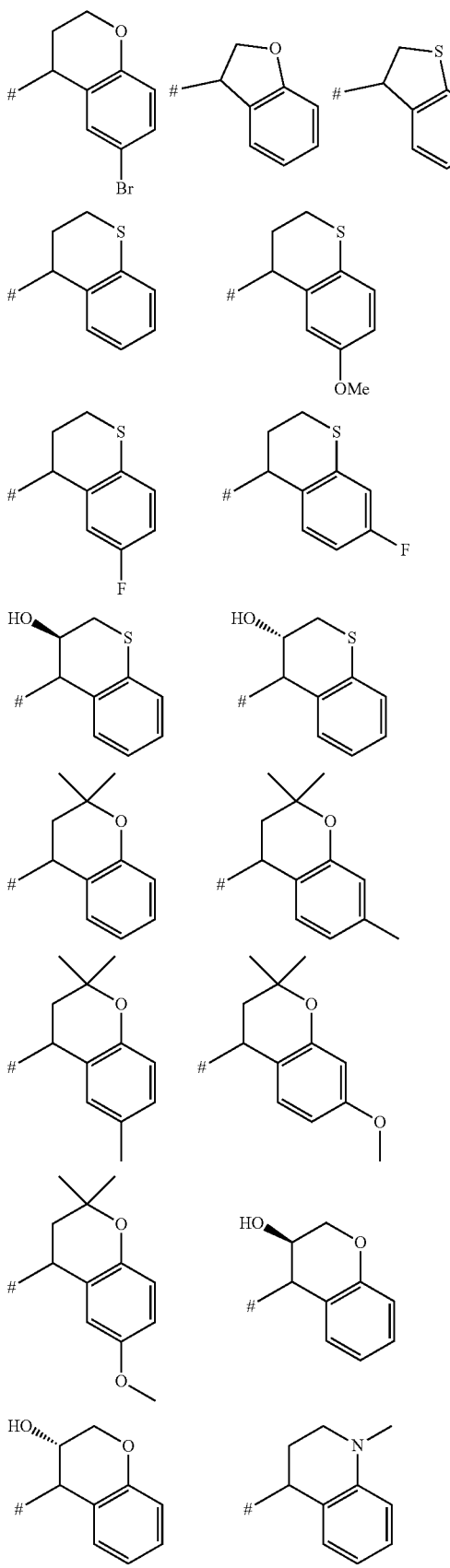

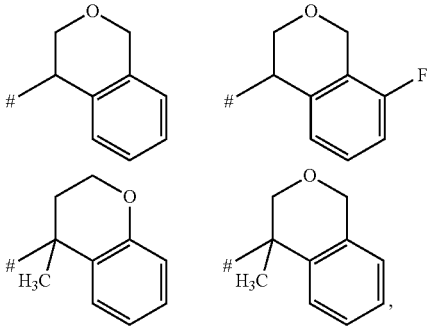

and stereoisomers, tautomers, N-oxides, hydrates, solvates, and salts thereof, and mixtures of same.

In a further embodiment of the first aspect, the present invention covers compounds of formula (I), supra, in which:
A is selected from the group consisting of

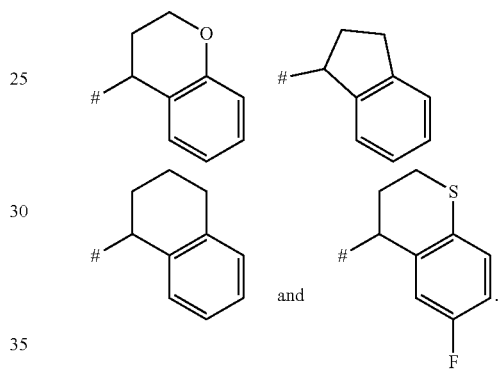

In a further embodiment of the first aspect, the present invention covers compounds of formula (I), supra, in which:
$R_p$ is hydrogen or $C_1$-$C_4$-alkyl, preferably methyl,
and stereoisomers, tautomers, N-oxides, hydrates, solvates, and salts thereof, and mixtures of same.

In a further embodiment of the first aspect, the present invention covers compounds of formula (I), supra, in which:
$R^2$ is selected from the group consisting of hydrogen, (2-amino-2-oxoethyl)amino, (2-aminoethyl)amino, (2-hydroxyethyl)amino, hydroxymethyl, methoxymethyl, 2-hydroxyethyl, (2-hydroxyethyl)oxy, (2-methoxy-2-oxoethyl)amino, (3-methoxy-3-oxopropyl)-methylamino, (2-methoxyethyl)(methyl)amino, (2-methoxyethyl)amino, (2-methoxyethyl)oxy, (2R,6S)-2,6-dimethylmorpholin-4-yl, 2-(trifluoromethyl)morpholin-4-yl, (2S)-2-methylmorpholin-4-yl, 2,2-difluoroethyl(methyl)amino, (3,3,3-trifluoropropyl)amino, (3-methoxybenzyl)oxy, (3rac,4rac)-3-amino-4-fluoropyrrolidin-1-yl, (3S)-3-(hydroxymethyl)pyrrolidin-1-yl, (carboxyethyl)amino, (cyclopentylmethyl)oxy, (pyridin-2-ylmethyl)amino, (rac)-3-hydroxypyrrolidin-1-yl, [2-(dimethylamino)ethyl]amino, 1,1-dioxidothiomorpholin-4-yl, 1,2-oxazolidin-2-yl, 1H-1,2,3-triazol-1-yl, 1H-imidazol-1-yl, 1H-pyrazol-1-yl, 1H-pyrazol-4-yl, 2,2-dimethylmorpholin-4-yl, 2,2-dimethylpyrrolidin-1-yl, 2,4-dimethyl-3,5-dioxo-1,2,4-triazolidin-1-yl, 2-amino-2-oxoethyl, 2H-1,2,3-triazol-2-yl, 1H-tetrazol-5-yl, 3-(pyrrolidin-1-yl)azetidin-1-yl, 3,3-difluoroazetidin-1-yl, 3,3-difluoropyrrolidin-1-yl, 3-fluoroazetidin-1-yl, 3-hydroxyazetidin-1-yl, 3-methylazetidin-1-yl, 3-oxopyrazolidin-1-yl, 1-(difluoromethyl)-1H-pyrazol-4-yl, 4-(trifluoromethyl)-1H-pyrazol-1-yl, 1-methyl-piperidin-4-yl, 4-fluoropiperidin-1-yl, 4,4-difluoropiperidin-1-yl, 4-oxoimidazolidin-1-yl, amino, anilino, azetidin-1-yl, benzyl(methyl)amino, chlorine, iodine, cyanomethyl, cyclobutyl(methyl)amino, cyclopentyloxy, cyclopropyl, cyclobutyl, cyclopentyl, cyclopropyl(ethyl)amino, cyclopropyl(methyl)amino, cyclopropylamino, diethylamino, dimethylamino, dimethylaminocarbonyl, aminomethyl, 2-aminoethyl, (dimethylamino)methyl, 2-(dimethylamino)ethyl, ethenyl, ethyl, ethylamino, ethyloxy, ethylsulfanyl, ethylsulfinyl, ethylsulfonyl, isopropyl, isopropyloxy, methoxyamino, methyl, methyl(2,2,2-trifluoroethyl)amino, oxetan-3-ylmethylamino, methyl(oxetan-3-yl)amino, methylamino, methyloxy, methylsulfanyl, morpholin-4-yl, morpholin-4-ylamino, nitrilomethyl, prop-1-en-2-yl, propyl, propylamino, pyridin-4-yloxetan-3-yl, tetrahydrofuran-3-yl, 3,6-dihydro-2H-pyran-4-yl, tetrahydropyran-4-yl, tetrahydro-2H-pyran-4-yloxy, 3-thienyl and thiomorpholin-4-y, and stereoisomers, tautomers, N-oxides, hydrates, solvates, and salts thereof, and mixtures of same.

In a further embodiment of the first aspect, the present invention covers compounds of formula (I), supra, in which:
$R^2$ is selected from the group consisting of hydrogen, 3-(pyrrolidin-1-yl)azetidin-1-yl, 3,3-difluoroazetidin-1-yl, 3-fluoroazetidin-1-yl, 3-hydroxyazetidin-1-yl, 3-methylazetidin-1-yl, azetidin-1-yl, dimethylamino, isopropyl, methyl and morpholin-4-yl, and stereoisomers, tautomers, N-oxides, hydrates, solvates, and salts thereof, and mixtures of same.

In a further embodiment of the first aspect, the present invention covers compounds of formula (I), supra, in which:
$R^3$ is hydrogen or $C_1$-$C_4$-alkyl, preferably methyl, and stereoisomers, tautomers, N-oxides, hydrates, solvates, and salts thereof, and mixtures of same.

In a further embodiment of the first aspect, the present invention covers compounds of formula (I), supra, in which:
$R^4$ is selected from the group consisting of hydrogen, halogen, preferably chlorine and fluorine, —OH, cyano, $C_1$-$C_4$-alkyl, preferably methyl, $C_1$-$C_4$-halogenoalkyl having 1 to 5 halogen atoms, preferably trifluoromethyl, $C_1$-$C_4$-alkoxy, preferably methoxy, $C_1$-$C_4$-halogenoalkoxy having 1 to 5 halogen atoms, preferably trifluoromethoxy, and $NH_2$, and stereoisomers, tautomers, N-oxides, hydrates, solvates, and salts thereof, and mixtures of same.

In a further embodiment of the first aspect, the present invention covers compounds of formula (I), supra, in which:
$R^5$ is selected from the group consisting of hydrogen, halogen, preferably chlorine and fluorine, —OH, cyano, $C_1$-$C_4$-alkyl, preferably methyl, $C_1$-$C_4$-halogenoalkyl having 1 to 5 halogen atoms, preferably trifluoromethyl, $C_1$-$C_4$-alkoxy, preferably methoxy, $C_1$-$C_4$-halogenoalkoxy having 1 to 5 halogen atoms, and stereoisomers, tautomers, N-oxides, hydrates, solvates, and salts thereof, and mixtures of same.

In a further embodiment of the first aspect, the present invention covers compounds of formula (I), supra, in which:
$R^6$ is selected from the group consisting of hydrogen, halogen, preferably chlorine and fluorine, —OH, cyano, $C_1$-$C_4$-alkyl, preferably methyl, $C_1$-$C_4$-halogenoalkyl having 1 to 5 halogen atoms, $C_1$-$C_4$-alkoxy, preferably methoxy, $C_1$-$C_4$-halogenoalkoxy having 1 to 5 halogen atoms, and stereoisomers, tautomers, N-oxides, hydrates, solvates, and salts thereof, and mixtures of same.

In a further embodiment of the first aspect, the present invention covers compounds of formula (I), supra, in which:
Q is a substituted phenyl ring of the formula (Q1)

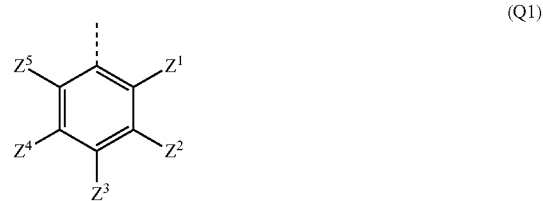

(Q1)

in which:
$Z^1$, $Z^2$, $Z^3$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, hydroxy, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, 4- to 6-membered heterocyclyl, which is optionally substituted with 1 or 2 substituents selected from the group consisting of fluorine, chlorine, bromine, methyl and cyano, —S—($C_1$-$C_4$-alkyl), —S(O)—($C_1$-$C_4$-alkyl), —SO$_2$—($C_1$-$C_4$-alkyl),), —S—($C_1$-$C_4$-halogenoalkyl) having 1 to 5 halogen atoms, —S(O)—($C_1$-$C_4$-halogenoalkyl) having 1 to 5 halogen atoms, —SO$_2$—($C_1$-$C_4$-halogenoalkyl) having 1 to 5 halogen atoms, or $Z^1$ and $Z^2$ form, together with the carbon atoms that they are connected to, a 5- or 6-membered heterocycloalkyl, a 5-membered heteroaryl, or a 6-membered heteroaryl, each of which may be optionally substituted with one or two substituents selected from the group consisting of methyl, fluorine and oxo, and $Z^3$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-alkoxy-C(O)—, $C_1$-$C_4$-halogenoalkoxy having 1 to 5 halogen atoms, or $Z^2$ and $Z^3$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two substituents selected from the group consisting of methyl, fluorine and oxo, and $Z^1$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

or in the formula (Q1)
$Z^1$ and $Z^5$ are independently selected from the group consisting of hydrogen, halogen, $C_1$-$C_4$-alkyl, $C_1$-$C_4$-alkoxy and $C_1$-$C_4$-halogenoalkyl having 1 to 5 halogen atoms $Z^2$ and $Z^4$ are independently selected from the group consisting of hydrogen, halogen, cyano, —OH, $C_1$-$C_4$-alkyl, $C_1$-$C_4$-alkoxy, —NH($C_1$-$C_4$-alkyl), —N($C_1$-$C_4$-alkyl)$_2$, $C_1$-$C_4$-halogenoalkyl having 1 to 5 halogen atoms, $C_1$-$C_4$-halogenoalkoxy having 1 to 5 halogen atoms, —S—($C_1$-$C_4$-alkyl), S—($C_1$-$C_4$-halogenoalkyl) having 1 to 5 halogen atoms and a 4- to 6-membered heterocycloalkyl, and $Z^3$ is selected from the group consisting of hydrogen, halogen, $C_1$-$C_4$-alkyl, $C_1$-$C_4$-alkoxy, $C_1$-$C_4$-halogenoalkoxy having 1 to 5 halogen atoms and —N($C_1$-$C_4$-alkyl)$_2$, or $Z^1$ and $Z^2$ form, together with the carbon atoms that they are connected to, a 5-membered heterocycloalkyl or a 5-membered heteroaryl, each of which may be optionally substituted with one or two substituents selected from the group consisting of methyl, fluorine and oxo, $Z^3$ and $Z^5$ are hydrogen, and $Z^4$ is selected from the group consisting of hydrogen and $C_1$-$C_4$-alkoxy-C(O)—, or $Z^1$ and $Z^5$ are independently selected from the group consisting of hydrogen, fluorine, chlorine, methyl, methoxy and trifluoromethyl, $Z^2$ and $Z^4$ are independently selected from the group consisting of hydrogen, fluorine, chlorine, —OH, cyano, methyl, ethyl, tert-butyl, —NHMe, —NMe$_2$, trifluoromethyl, methoxy, trifluoromethoxy, —SMe, 2,2,2-trifluoroethyl)sulfanyl and morpholinyl, and $Z^3$ is independently selected from the group consisting of hydrogen, fluorine, chlorine, methyl, methoxy, difluoromethoxy and —NMe$_2$.

In a further aspect of the present invention in the formula (I) as defined in any of the embodiments described supra Q may have one of the following meanings:

Q is a pyridine ring of the formula (Q2)

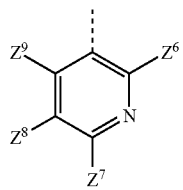

(Q2)

in which:

$Z^6$, $Z^7$, $Z^8$ and $Z^9$ are independently selected from the group consisting of hydrogen halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$; or Q is a pyrimidine ring of the formula (Q3)

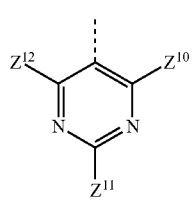

(Q3)

in which:

$Z^{10}$, $Z^{11}$ and $Z^{12}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$; or Q is a pyridine ring of the formula (Q4)

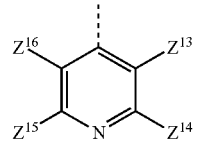

(Q4)

in which:

$Z^{13}$, $Z^{14}$, $Z^{11}$ and $Z^{16}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_1$-$C_4$-hydroxyalkyl, NH$_2$, —NH($C_1$-$C_4$-alkyl), —N($C_1$-$C_4$-alkyl)$_2$, —NH—CO—$C_1$-$C_4$-alkyl, and monocyclic heterocycles selected from the group of 4- to 7-membered heterocycloalkyl or 5-membered heteroaryls having at least one nitrogen atom via which the heteroaryl ring is connected to the pyridine ring, each of which is optionally substituted with 1, 2 or 3 substituents independently selected from the group consisting of halogen, cyano, nitro, —OH, oxo, thiono, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, —S—($C_1$-$C_4$-halogenoalkyl) having 1 to 5 halogen atoms, —S(O)—($C_1$-$C_4$-halogenoalkyl) having 1 to 5 halogen atoms, —SO$_2$—($C_1$-$C_4$-halogenoalkyl) having 1 to 5 halogen atoms;

or in the formula (Q4)

$Z^{13}$, $Z^{14}$, $Z^{15}$ and $Z^{16}$ are independently selected from the group consisting of hydrogen, halogen, cyano, $C_1$-$C_4$-alkyl, $C_1$-$C_4$-alkoxy, $C_1$-$C_4$-hydroxyalkyl, NH$_2$, —NH($C_1$-$C_4$-alkyl), —N($C_1$-$C_4$-alkyl)$_2$, —NH—CO—$C_1$-$C_4$-alkyl, and monocyclic heterocycles selected from the group of 4- to 7-membered heterocycloalkyl or 5-membered heteroaryls having at least one nitrogen atom via which the heteroaryl ring is connected to the pyridine ring, each of which is optionally substituted with 1, 2 or 3 substituents independently selected from the group consisting of halogen, cyano, nitro, —OH, oxo, thiono, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, —S—($C_1$-$C_4$-halogenoalkyl) having 1 to 5 halogen atoms, —S(O)—($C_1$-$C_4$-halogenoalkyl) having 1 to 5 halogen atoms, —SO$_2$—($C_1$-$C_4$-halogenoalkyl) having 1 to 5 halogen atoms;

or $Z^{13}$, $Z^{14}$, $Z^5$ and $Z^{16}$ are independently selected from the group consisting of hydrogen, fluorine, chlorine, cyano, methyl, methoxy, ethoxy, isopropoxy, hydroxymethyl, NH$_2$, —NHMe —NMe$_2$, —NH—C(O)-Me, morpholinyl; or Q is a pyridine ring of the formula (Q5)

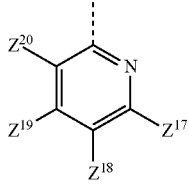

(Q5)

in which:

$Z^{17}$, $Z^{18}$, $Z^{19}$ and $Z^{20}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$;

or in the formula (Q5)

$Z^{17}$, $Z^{18}$, and $Z^{19}$ are hydrogen, and $Z^{20}$ is halogen;

or $Z^{17}$, $Z^{18}$, and $Z^{19}$ are hydrogen, and $Z^{20}$ is fluorine, chlorine; or Q is a 5-membered aromatic heterocycle of the formula (Q6)

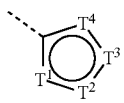

(Q6)

in which:

$T^1$-$T^4$ are independently selected from the group consisting of N, O, S, C—$Z^{21}$ and N—$Z^{22}$, wherein not more than one of $T^1$-$T^4$ is O, not more than one of $T^1$-$T^4$ is S, not more than one of $T^1$-$T^4$ is N—$Z^{22}$, and wherein each $Z^{21}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and each $Z^{22}$ is independently selected from the group consisting of hydrogen, $C_1$-$C_4$-alkyl, $C_1$-$C_4$-halogenoalkyl having 1 to 5 halogen atoms, $C_1$-$C_4$-alkyl-$C_3$-$C_6$-cycloalkyl, $C_1$-$C_4$-alkoxy-$C_1$-$C_4$-alkyl or in the formula (Q6)

$T^1$-$T^4$ are independently selected from the group consisting of N, O, S, C—$Z^{21}$ and N—$Z^{22}$, wherein not more than one of $T^1$-$T^4$ is O, not more than one of $T^1$-$T^4$ is S, not more than one of $T^1$-$T^4$ is N—$Z^{22}$, and wherein each $Z^{21}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and each $Z^{22}$ is independently selected from the group consisting of hydrogen, $C_1$-$C_4$-alkyl, $C_1$-$C_4$-halogenoalkyl having 1 to 5 halogen atoms, $C_1$-$C_4$-alkyl-$C_3$-$C_6$-cycloalkyl, $C_1$-$C_4$-alkoxy-$C_1$-$C_4$-alkyl, or Q is selected from the group consisting of

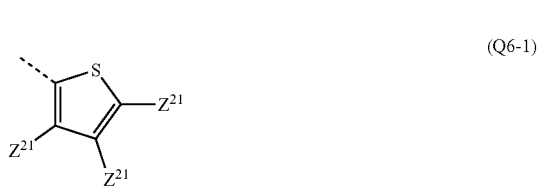

(Q6-1)

(Q6-2)

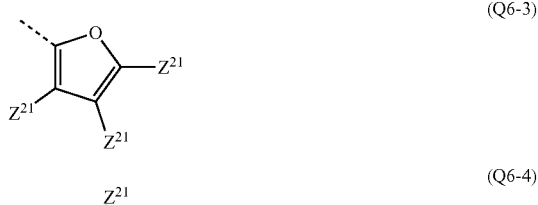

(Q6-3)

(Q6-4)

(Q6-5)

(Q6-6)

(Q6-7)

(Q6-8)

(Q6-9)

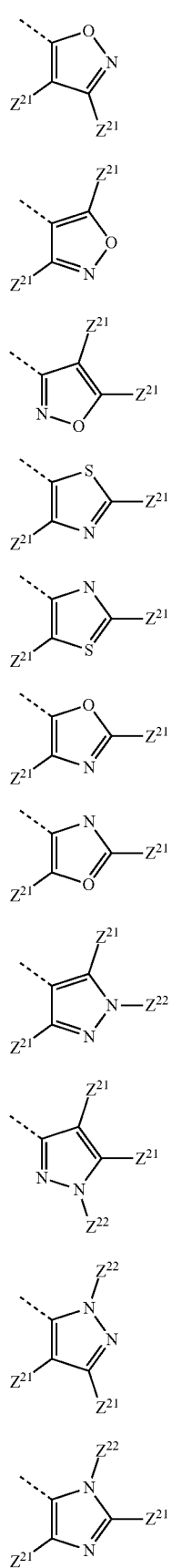
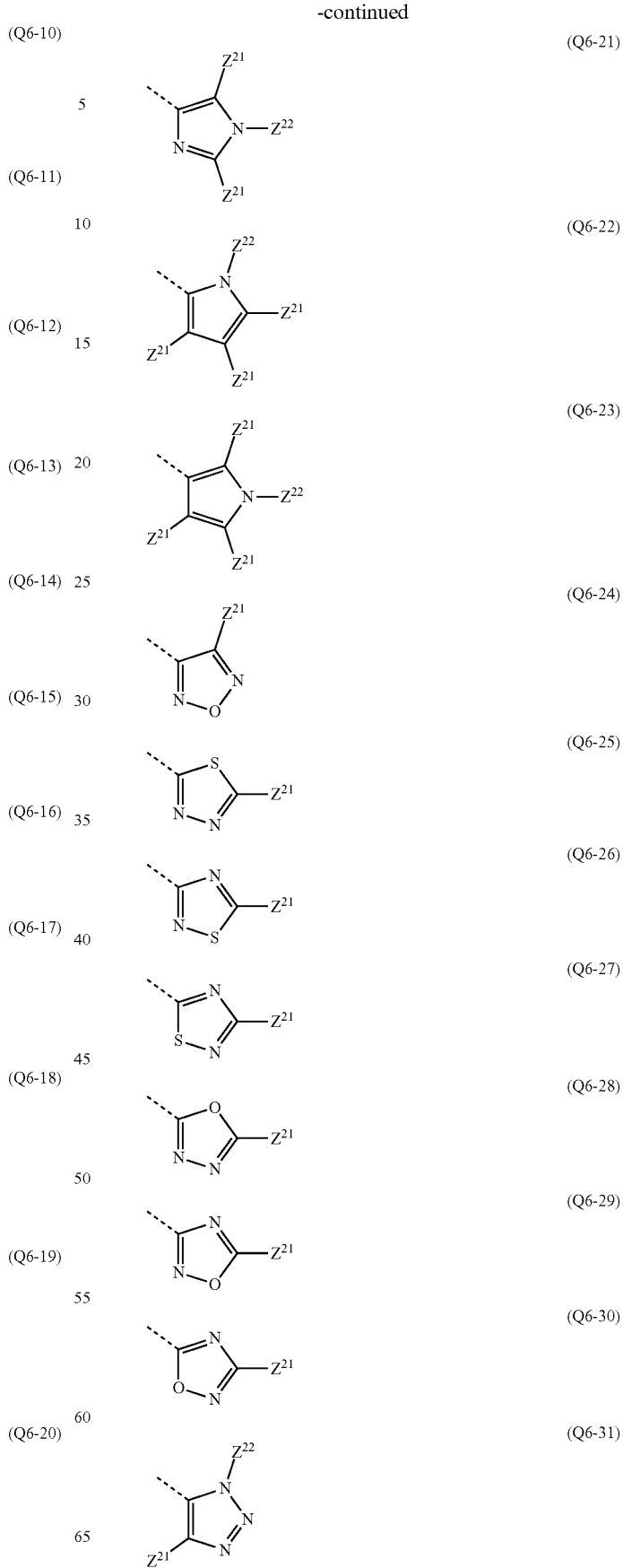

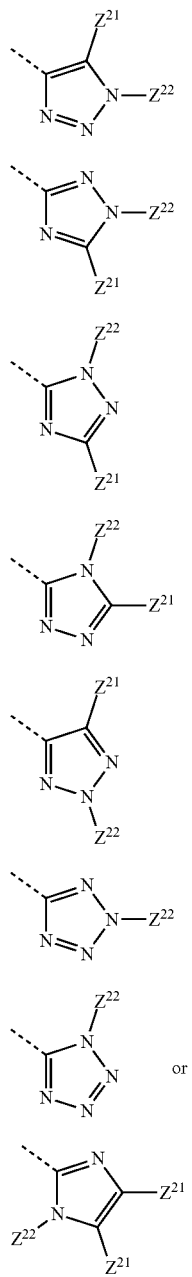

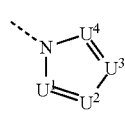

in which:
each $Z^{21}$ is independently selected from the group consisting of hydrogen, fluorine, chlorine, cyano, methyl, trifluoromethyl, methoxy and
$Z^{22}$ is hydrogen, methyl; or
Q is a 5-membered aromatic heterocycle of the formula (Q7)

in which:
$U^1$-$U^4$ are independently selected from the group consisting of N and C—$Z^{23}$, wherein not more than three of $U^1$-$U^4$ are N, and wherein
each $Z^{23}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy;
or in the formula (Q7)
$U^1$-$U^4$ are independently selected from the group consisting of N and C—$Z^{23}$, wherein not more than three of $U^1$-$U^4$ are N, and wherein
each $Z^{23}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy;
or
Q is selected from the group consisting of

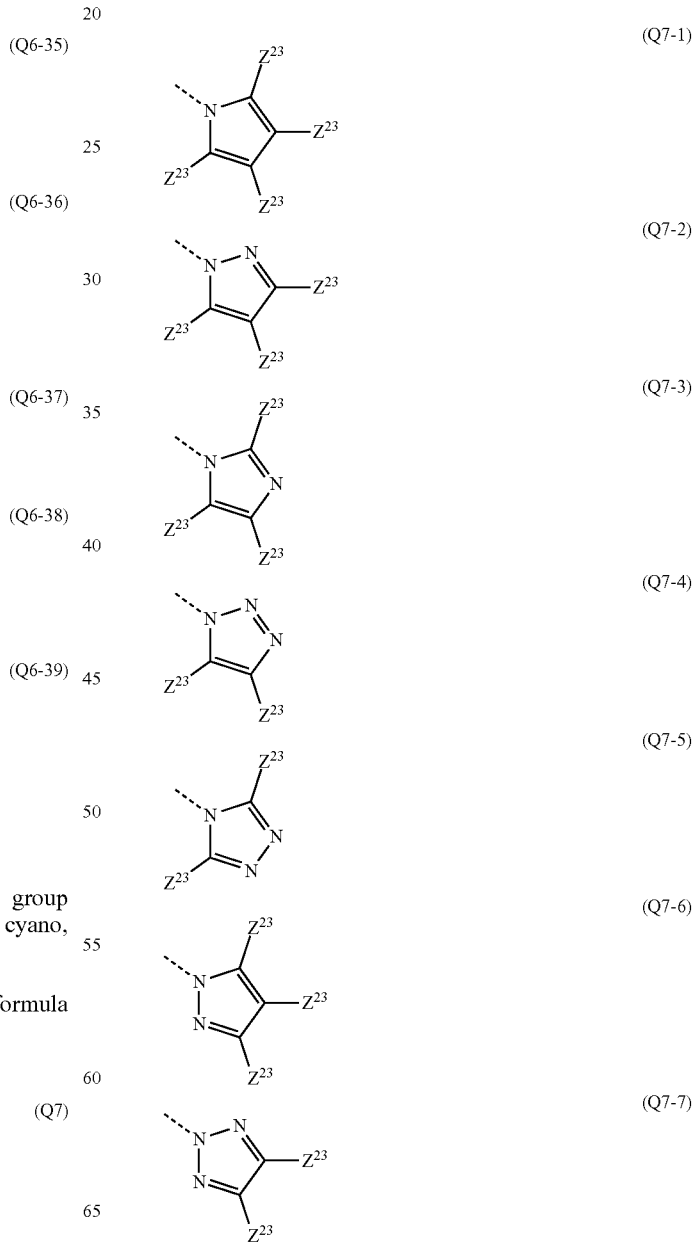

-continued

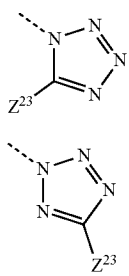

(Q7-8)

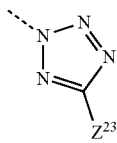

(Q7-9)

in which:
each $Z^{23}$ is independently selected from the group consisting of hydrogen, fluorine, chlorine, cyano, methyl, trifluoromethyl, methoxy.

In a further embodiment of the first aspect, the present invention covers compounds of formula (I), supra in which Q is selected from the group consisting of phenyl, 2,5-bis(trifluoromethyl)phenyl, 2,3,4-trifluorophenyl, 2,3,5-trichlorophenyl, 2,3,5-trifluorophenyl, 2,3,6-trifluorophenyl, 2,3-dichlorophenyl, 2,3-dichloro-5-cyanophenyl, 2,3-dichloro-5-hydroxyphenyl, 2,3-difluorophenyl, 2,4,5-trifluorophenyl, 2,4,6-trifluoro-3-methoxyphenyl, 2,4-difluoro-3-hydroxyphenyl, 2,4-difluoro-3-methoxyphenyl, 2,5-dichlorophenyl, 2-chloro-5-cyanophenyl, 2-chloro-5-methylphenyl, 2,5-difluoro-4-methoxyphenyl, 2,6-difluorophenyl, 2-chloro-3-fluorophenyl, 2-chloro-4-(dimethylamino)phenyl, 2-chloro-4-fluorophenyl, 2-chloro-5-fluorophenyl, 2-chloro-6-fluorophenyl, 2-chlorophenyl, 3,5-difluoropyridin-4-yl, 2-chloro-3-fluoropyridin-4-yl, 2-fluoro-5-methylphenyl, 3-fluoro-5-methylphenyl, 2-fluoro-3-(trifluoromethoxy)phenyl, 2-fluoro-3-(trifluoromethyl)phenyl, 5-fluoro-2-(trifluoromethyl)phenyl, 3-cyano-5-methylphenyl, 3-(trifluoromethyly)phenyl, 3-(trifluoromethoxy)phenyl, 3,4,5-trifluorophenyl, 3,4-dichlorophenyl, 3,4-difluoro-2-methoxyphenyl, 3,4-difluorophenyl, 3,5-dichloro-4-(dimethylamino)phenyl, 3,5-dichloro-4-fluorophenyl, 3,5-dichlorophenyl, 3,5-difluorophenyl, 4-(difluoromethoxy)-3,5-difluorophenyl, 2,5-dimethylphenyl, 3,5-dimethylphenyl, 3-tert-butyl-5-methylphenyl, 5-tert-butyl-2-chloro-3-methylphenyl, 3-chloro-2-fluoro-5-methylphenyl, 3-chloro-2-fluorophenyl, 3-chloro-2-methylphenyl, 3-chloro-4-fluorophenyl, 3-chloro-4-methylphenyl, 2-chloro-3-(trifluoromethyl)phenyl, 2-methyl-5-(trifluoromethyl)phenyl, 3-chloro-5-(trifluoromethyl)phenyl, 3-chloro-5-ethylphenyl, 3-chloro-5-fluorophenyl, 3-chloro-5-methoxyphenyl, 3-chloro-5-methylphenyl, 3-chlorophenyl, 3-fluoro-2-methylphenyl, 3-fluoro-4-methoxyphenyl, 3-fluoro-5-methylphenyl, 4-fluoro-3-methoxyphenyl, 5-chloro-2,4-difluorophenyl, 5-chloro-2-fluoro-3-methylphenyl, 5-chloro-2-fluoro-4-methylphenyl, 5-chloro-2-fluorophenyl, 5-chloro-2-methoxyphenyl, 5-fluoro-2-methylphenyl, 5-fluoro-2-methoxyphenyl, 3,5-diethylphenyl, 2-chloro-3,5-diethylphenyl, 3-chloro-2-thienyl, 4-chloro-2-thienyl, 5-chloro-2-thienyl, 2,5-dichloro-3-thienyl, 5-fluoro-2-thienyl, 5-cyano-2-thienyl, 5-cyano-4-methyl-2-thienyl, 5-methyl-2-thienyl, 2,5-dimethyl-3-thienyl, 5-(trifluoromethyl)-2-thienyl 3-tert-butyl-5-fluorophenyl, and 3-tert-butyl-5-chlorophenyl.

In a further embodiment of the first aspect, the present invention covers compounds of formula (I), supra in which Q is selected from the group consisting of 2,3,5-trifluorophenyl, 3,5-dichlorophenyl, 3-tert-butyl-5-fluorophenyl, and 3-tert-butyl-5-chlorophenyl.

According to the present invention it is most preferred that in the compounds of formula (I), supra,
Q is a substituted phenyl ring of the formula (Q1) as defined anywhere herein.

In a further embodiment of the first aspect, the present invention covers compounds of formula (I), supra, in which A is A3 or A4

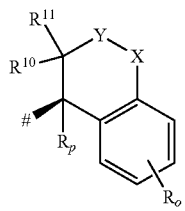

A3

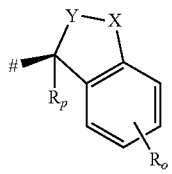

A4 wherein
$R_p$ is selected from the group consisting of hydrogen, $C_1$-$C_4$-alkyl; preferably hydrogen, and stereoisomers, tautomers, N-oxides, hydrates, solvates, and salts thereof, and mixtures of same.

In a particular further embodiment of the first aspect, the present invention covers combinations of two or more of the above mentioned embodiments under the heading "further embodiments of the first aspect of the present invention".

The present invention covers any sub-combination within any embodiment or aspect of the present invention of compounds of general formula (I), supra.

The present invention covers the compounds of general formula (I) which are disclosed in the Example Section of this text, infra.

The compounds according to the invention of general formula (I) can be prepared according to schemes 1-2 as shown in the Experimental Section to the present invention (General Procedures). The schemes and procedures described illustrate synthetic routes to the compounds of general formula (I) of the invention and are not intended to be limiting. It is clear to the person skilled in the art that the order of transformations as exemplified in schemes 1-2 can be modified in various ways. The order of transformations exemplified in these schemes is therefore not intended to be limiting. In addition, interconversion of any of the substituents, Q, A, $R^1$, $R^2$, $R^3$, $R^4$, $R^5$ or $R^6$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in

*Protective Groups in Organic Synthesis*, 3$^{rd}$ edition, Wiley 1999). Specific examples are described in the subsequent paragraphs.

In accordance with a second aspect, the present invention covers methods of preparing compounds of general formula (I) as defined supra, said methods comprising the step of allowing an intermediate compound of general formula 1C:

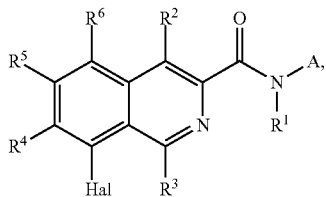

1C in which A, $R^1$, $R^2$, $R^3$, $R^4$, $R^5$, and $R^6$ are as defined for the compound of general formula (I) as defined supra, and Hal is halogen, particularly chlorine and bromine, to react with a compound of general formula 1D:

1D in which each R may be individually H or Me or both R are pinacolate,
thereby giving a compound of general formula (I)

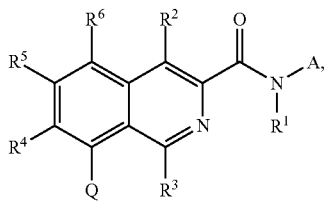

(I)

in which A, $R^1$, $R^2$, $R^3$, $R^4$, $R^5$, $R^6$, and Q are as defined supra, then optionally converting said compound into solvates, salts and/or solvates of such salts using the corresponding (i) solvents and/or (ii) bases or acids.

In accordance with a third aspect, the present invention covers intermediate compounds which are useful for the preparation of the compounds of general formula (I), supra.

Particularly, the inventions covers the intermediate compounds of general formula 1A:

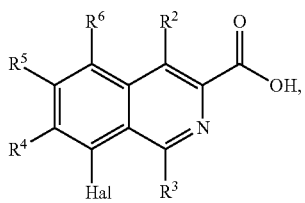

1A in which
$R^2$ is as defined for the compound of general formula (I) supra,
$R^3$, $R^4$, $R^5$, and $R^6$, are as defined for the compound of general formula (I) supra, and
Hal is bromine or chlorine,
and stereoisomers, tautomers, N-oxides, hydrates, solvates, and salts thereof, and mixtures of same.

Further, the inventions covers the intermediate compounds of general formula 1C:

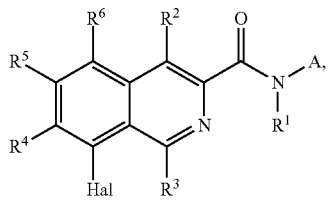

1C in which
A, $R^1$, $R^2$, $R^3$, $R^4$, $R^5$, and $R^6$, are as defined for the compound of general formula (I) supra, and
Hal is bromine or chlorine,
and stereoisomers, tautomers, N-oxides, hydrates, solvates, and salts thereof, and mixtures of same.

In particular, the inventions covers the intermediate compounds of general formula 1C infra, preferably those of formula 1C-1 to 1C-9 according to Table 2 infra.

In accordance with a fourth aspect, the present invention covers the use of said intermediate compounds for the preparation of a compound of general formula (I) as defined supra.

The present invention covers the intermediate compounds which are disclosed in the Example Section of this text, infra.

The compounds of general formula (I) of the present invention can be converted to any salt, preferably pharmaceutically acceptable salts, as described herein, by any method which is known to the person skilled in the art. Similarly, any salt of a compound of general formula (I) of the present invention can be converted into the free compound, by any method which is known to the person skilled in the art.

Compounds of general formula (I) of the present invention demonstrate a valuable pharmacological spectrum of action, which could not have been predicted. Compounds of the present invention have surprisingly been found to effectively interact with Slo-1 and it is possible therefore that said compounds be used for the treatment or prevention of diseases, preferably helminthic infections, particularly of gastro-intestinal and extra-intestinal helminth infections, more particularly of gastro-intestinal and extra-intestinal infections with nematodes in humans and animals.

Compounds of the present invention can be utilized to control, treat and/or prevent helminth infections, in particular gastro-intestinal and extra-intestinal helminth infections. This method comprises administering to a mammal in need thereof an amount of a compound of this invention, or a pharmaceutically acceptable salt, isomer, polymorph, metabolite, hydrate, solvate or ester thereof; which is effective to treat the disorder.

In an alternative aspect, this method comprises administering to birds, namely cage birds or in particular poultry, in need thereof an amount of a compound of this invention, or a pharmaceutically acceptable salt, isomer, polymorph, metabolite, hydrate, solvate or ester thereof; which is effective to treat the disorder.

Specifically in the field of veterinary medicine, compounds of the the present invention are suitable, with favourable toxicity in warm blooded animals, for controlling parasites, in particular helminths, which occur in animal breeding and animal husbandry in livestock, breeding, zoo, laboratory, experimental and domestic animals. They are active against all or specific stages of development of the parasites, in particular of the helminths.

Agricultural livestock include, for example, mammals, such as, sheep, goats, horses, donkeys, camels, buffaloes, rabbits, reindeers, fallow deers, and in particular cattle and pigs; or poultry, such as turkeys, ducks, geese, and in particular chickens; or fish or crustaceans, e.g. in aquaculture.

Domestic animals include, for example, mammals, such as hamsters, guinea pigs, rats, mice, chinchillas, ferrets or in particular dogs, cats; cage birds; reptiles; amphibians or aquarium fish.

The present invention also provides methods of treating helminth infections, particularly gastro-intestinal and extra-intestinal helminth infections, more particularly gastro-intestinal and extra-intestinal infections with nematodes.

These disorders have been well characterized in animals, and can be treated by administering pharmaceutical compositions of the present invention.

The term "treating" or "treatment" as used in the present text is used conventionally, e.g., the management or care of a subject for the purpose of combating, alleviating, reducing, relieving, improving the condition of a disease or disorder, such as a nematode infection. In particular, and particularly in the animal health or veterinary field, the term "treating" or "treatment" includes prophylactic, metaphylactic or therapeutical treatment.

Helminths pathogenic for humans or animals include, for example, acanthocephala, nematodes, pentastoma and platyhelmintha (e.g. monogenea, cestodes and trematodes).

Exemplary helminths include, without any limitation:

Monogenea: e.g.: *Dactylogyrus* spp., *Gyrodactylus* spp., *Microbothrium* spp., *Polystoma* spp., *Troglocephalus* spp.

Cestodes: from the order of the Pseudophyllidea, for example: *Bothridium* spp., *Diphyllobothrium* spp., *Diplogonoporus* spp., *Ichthyobothrium* spp., *Ligula* spp., *Schistocephalus* spp., *Spirometra* spp.

from the order of the Cyclophyllida, for example: *Andyra* spp., *Anoplocephala* spp., *Avitellina* spp., *Bertiella* spp., *Cittotaenia* spp., *Davainea* spp., *Diorchis* spp., *Diplopylidium* spp., *Dipylidium* spp., *Echinococcus* spp., *Echinocotyle* spp., *Echinolepis* spp., *Hydatigera* spp., *Hymenolepis* spp., *Joyeuxiella* spp., *Mesocestoides* spp., *Moniezia* spp., *Paranoplocephala* spp., *Raillietina* spp., *Stilesia* spp., *Taenia* spp., *Thysaniezia* spp., *Thysanosoma* spp.

Trematodes: from the class of the Digenea, for example: *Austrobilharzia* spp., *Brachylaima* spp., *Calicophoron* spp., *Catatropis* spp., *Clonorchis* spp. *Collyriclum* spp., *Cotylophoron* spp., *Cyclocoelum* spp., *Dicrocoelium* spp., *Diplostomum* spp., *Echinochasmus* spp., *Echinoparyphium* spp., *Echinostoma* spp., *Eurytrema* spp., *Fasciola* spp., *Fasciolides* spp., *Fasciolopsis* spp., *Fischoederius* spp., *Gastrothylacus* spp., *Gigantobilharzia* spp., *Gigantocotyle* spp., *Heterophyes* spp., *Hypoderaeum* spp., *Leucochloridium* spp., *Metagonimus* spp., *Metorchis* spp., *Nanophyetus* spp., *Notocotylus* spp., *Opisthorchis* spp., *Ornithobilharzia* spp., *Paragonimus* spp., *Paramphistomum* spp., *Plagiorchis* spp., *Posthodiplostomum* spp., *Prosthogonimus* spp., *Schistosoma* spp., *Trichobilharzia* spp., *Troglotrema* spp., *Typhlocoelum* spp.

Nematodes: from the order of the Trichinellida, for example: *Capillaria* spp., *Eucoleus* spp., *Paracapillaria* spp., *Trichinella* spp., *Trichomosoides* spp., *Trichuris* spp.

from the order of the Tylenchida, for example: *Micronema* spp., *Parastrongyloides* spp., *Strongyloides* spp.

from the order of the Rhabditina, for example: *Aelurostrongylus* spp., *Amidostomum* spp., *Ancylostoma* spp., *Angiostrongylus* spp., *Bronchonema* spp., *Bunostomum* spp., *Chabertia* spp., *Cooperia* spp., *Cooperioides* spp., *Crenosoma* spp., *Cyathostomum* spp., *Cyclococercus* spp., *Cyclodontostomum* spp., *Cylicocyclus* spp., *Cylicostephanus* spp., *Cylindropharynx* spp., *Cystocaulus* spp., *Dictyocaulus* spp., *Elaphostrongylus* spp., *Filaroides* spp., *Globocephalus* spp., *Graphidium* spp., *Gyalocephalus* spp., *Haemonchus* spp., *Heligmosomoides* spp., *Hyostrongylus* spp., *Marshallagia* spp., *Metastrongylus* spp., *Muellerius* spp., *Necator* spp., *Nematodirus* spp., *Neostrongylus* spp., *Nippostrongylus* spp., *Obeliscoides* spp., *Oesophagodontus* spp., *Oesophagostomum* spp., *Ollulanus* spp.; *Ornithostrongylus* spp., *Oslerus* spp., *Ostertagia* spp., *Paracooperia* spp., *Paracrenosoma* spp., *Parafilaroides* spp., *Parelaphostrongylus* spp., *Pneumocaulus* spp., *Pneumostrongylus* spp., *Poteriostomum* spp., *Protostrongylus* spp., *Spicocaulus* spp., *Stephanurus* spp., *Strongylus* spp., *Syngamus* spp., *Teladorsagia* spp., *Trichonema* spp., *Trichostrongylus* spp., *Triodontophorus* spp., *Troglostrongylus* spp., *Uncinaria* spp.

from the order of the Spirurida, for example: *Acanthocheilonema* spp., *Anisakis* spp., *Ascaridia* spp.; *Ascaris* spp., *Ascarops* spp., *Aspiculuris* spp., *Baylisascaris* spp., *Brugia* spp., *Cercopithifilaria* spp., *Crassicauda* spp., *Dipetalonema* spp., *Dirofilaria* spp., *Dracunculus* spp.; *Draschia* spp., *Enterobius* spp., *Filaria* spp., *Gnathostoma* spp., *Gongylonema* spp., *Habronema* spp., *Heterakis* spp.; *Litomosoides* spp., *Loa* spp., *Onchocerca* spp., *Oxyuris* spp., *Parabronema* spp., *Parafilaria* spp., *Parascaris* spp., *Passalurus* spp., *Physaloptera* spp., *Probstmayria* spp., *Pseudofilaria* spp., *Setaria* spp., *Skjrabinema* spp., *Spirocerca* spp., *Stephanofilaria* spp., *Strongyluris* spp., *Syphacia* spp., *Thelazia* spp., *Toxascaris* spp., *Toxocara* spp., *Wuchereria* spp.

Acantocephala: from the order of the Oligacanthorhynchida, for example: *Macracanthorhynchus* spp., *Prosthenorchis* spp.; from the order of the Moniliformida, for example: *Moniliformis* spp.

from the order of the Polymorphida, for example: *Filicollis* spp.; from the order of the Echinorhynchida, for example: *Acanthocephalus* spp., *Echinorhynchus* spp., *Leptorhynchoides* spp.

Pentastoma: from the order of the Porocephalida, for example: *Linguatula* spp.

The compounds of the present invention can be used in particular in therapy and prevention, i.e. prophylaxis, of helminth infections, particularly gastro-intestinal and extra-intestinal helminth infections, more particularly gastro-intestinal and extra-intestinal infections with nematodes.

By using the compounds of the present invention to control animal parasites, in particular helminths, it is intended to reduce or prevent illness, cases of deaths and performance reductions (in the case of meat, milk, wool, hides, eggs, honey and the like), so that more economical and simpler animal keeping is made possible and better animal well-being is achievable.

The term "control" or "controlling", as used herein with regard to the animal health field, means that the compounds of the present invention are effective in reducing the incidence of the respective parasite in an animal infected with such parasites to innocuous levels. More specifically, "controlling", as used herein, means that the compounds of the present invention are effective in killing the respective parasite, inhibiting its growth, or inhibiting its proliferation.

In accordance with a further aspect, the present invention covers compounds of general formula (I), as described supra, or stereoisomers, tautomers, N-oxides, hydrates, solvates, and salts thereof, particularly pharmaceutically acceptable salts thereof, or mixtures of same, for use in the treatment or prevention of diseases, in particular of helminth infections, particularly of gastro-intestinal and extra-intestinal helminth infections, more particularly of gastro-intestinal and extra-intestinal infections with nematodes.

The pharmaceutical activity of the compounds according to the invention can be explained by their interaction with the Slo-1 ion channel.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, for the treatment or prevention of diseases, in particular of helminth infections, particularly of gastro-intestinal and extra-intestinal helminth infections, more particularly of gastro-intestinal and extra-intestinal infections with nematodes.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, in a method of treatment or prevention of diseases, in particular of helminth infections, particularly of gastro-intestinal and extra-intestinal helminth infections, more particularly of gastro-intestinal and extra-intestinal infections with nematodes.

In accordance with a further aspect, the present invention covers use of a compound of general formula (I), as described supra, or stereoisomers, tautomers, N-oxides, hydrates, solvates, and salts thereof, particularly pharmaceutically acceptable salts thereof, or mixtures of same, for the preparation of a pharmaceutical composition, preferably a medicament, for the prevention or treatment of diseases, in particular of helminth infections, particularly of gastro-intestinal and extra-intestinal helminth infections, more particularly of gastro-intestinal and extra-intestinal infections with nematodes.

In accordance with a further aspect, the present invention covers a method of treatment or prevention of diseases, in particular of helminth infections, particularly of gastro-intestinal and extra-intestinal helminth infections, more particularly of gastro-intestinal and extra-intestinal infections with nematodes, using an effective amount of a compound of general formula (I), as described supra, or stereoisomers, tautomers, N-oxides, hydrates, solvates, and salts thereof, particularly pharmaceutically acceptable salts thereof, or mixtures of same.

In accordance with a further aspect, the present invention covers compounds of general formula (I), as described supra, or stereoisomers, tautomers, N-oxides, hydrates, solvates, and salts thereof, particularly pharmaceutically acceptable salts thereof, or mixtures of same, for use as an antiendoparasitical agent.

In accordance with a further aspect, the present invention covers compounds of general formula (I), as described supra, or stereoisomers, tautomers, N-oxides, hydrates, solvates, and salts thereof, particularly pharmaceutically acceptable salts thereof, or mixtures of same, for use as a anthelmintic agent, in particular for use as a nematicidal agent, a platyhelminthicidal agent, an acanthocephalicidal agent, or a pentastomicidal agent.

In accordance with a further aspect, the present invention covers pharmaceutical compositions, in particular a veterinary formulation, comprising a compound of general formula (I), as described supra, or a stereoisomer, a tautomer, an N-oxide, a hydrate, a solvate, a salt thereof, particularly a pharmaceutically acceptable salt, or a mixture of same, and one or more excipients), in particular one or more pharmaceutically acceptable excipient(s). Conventional procedures for preparing such pharmaceutical compositions in appropriate dosage forms can be utilized.

In accordance with a further aspect, the present invention covers a method for preparing a pharmaceutical composition, in particular a veterinary formulation, comprising the step of mixing a compound of general formula (I), as described supra, or a stereoisomer, a tautomer, an N-oxide, a hydrate, a solvate, a salt thereof, particularly a pharmaceutically acceptable salt, or a mixture of same, with one or more excipients), in particular one or more pharmaceutically acceptable excipient(s).

In accordance with a further aspect, the present invention covers a method of treatment or prevention of diseases, in particular of helminth infections, particularly of gastro-intestinal and extra-intestinal helminth infections, more particularly of gastro-intestinal and extra-intestinal infections with nematodes, using a pharmaceutical composition, in particular a veterinary formulation, comprising an effective amount of a compound of general formula (I), as described supra, or stereoisomers, tautomers, N-oxides, hydrates, solvates, and salts thereof, particularly pharmaceutically acceptable salts thereof, or mixtures of same.

In accordance with a further aspect, the present invention covers a method for controlling helminth infections in humans and/or animals by administering an anthelminthically effective amount of at least one compound of general formula (I) as defined anywhere herein to a human or an animal in need thereof.

The present invention furthermore covers pharmaceutical compositions, in particular veterinary formulations, which comprise at least one compound according to the invention, conventionally together with one or more pharmaceutically suitable excipients, and to their use for the above mentioned purposes.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent. Such administration can be carried out prophylactically, methaphylactically or therapeutically.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, chewables (for example soft chewables), powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, spot-ons, dusting powders, implants or stents.

The compounds according to the invention can be incorporated into the stated administration forms. This can be effected in a manner known per se by mixing with pharmaceutically suitable excipients. Pharmaceutically suitable excipients include, inter alia, fillers and carriers (for example cellulose, microcrystalline cellulose (such as, for example, Avicel®), lactose, mannitol, starch, calcium phosphate (such as, for example, Di-Cafos®)), ointment bases (for example petroleum jelly, paraffins, triglycerides, waxes, wool wax, wool wax alcohols, lanolin, hydrophilic ointment, polyethylene glycols), bases for suppositories (for example polyethylene glycols, cacao butter, hard fat), solvents (for example water, ethanol, isopropanol, glycerol, propylene glycol, medium chain-length triglycerides fatty oils, liquid polyethylene glycols, paraffins), surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic©), buffers, acids and bases (for example phosphates, carbonates, citric acid, acetic acid, hydrochloric acid, sodium hydroxide solution, ammonium carbonate, trometamol, triethanolamine), isotonicity agents (for example glucose, sodium chloride), adsorbents (for example highly-disperse silicas), viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatine), disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)), flow regulators, lubricants, glidants and mould release agents (for example magnesium stearate, stearic acid, talc, highly-disperse silicas (such as, for example, Aerosil®)), coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)), capsule materials (for example gelatine, hydroxypropylmethylcellulose), synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

In accordance with another aspect, the present invention covers pharmaceutical combinations, in particular medicaments, comprising at least one compound of general formula (I) of the present invention and at least one or more further active ingredients, in particular for the treatment and/or prevention of an endo- and/or ectoparasiticidal infection.

The term "endoparasite" in the present invention is used as known to persons skilled in the art, and refers in particular to helminths. The term "ectoparasite" in the present invention is used as known to persons skilled in the art, and refers in particular to arthropods, particularly insects or acarids.

Particularly, the present invention covers a pharmaceutical combination, in particular a veterinary combination, which comprises:
one or more first active ingredients, in particular compounds of general formula (I) as defined supra, and
one or more further active ingredients, in particular one or more endo- and/or ectoparasiticides.

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

The compounds of the present invention can be administered as the sole pharmaceutical agent or in combination with one or more other pharmaceutically active ingredients where the combination causes no unacceptable adverse effects. The present invention also covers such pharmaceutical combinations. For example, the compounds of the present invention can be combined with known ectoparasiticides and/or endoparasiticides.

The other or further active ingredients specified herein by their common names are known and described, for example, in the Pesticide Manual ("The Pesticide Manual" 16th Ed., British Crop Protection Council 2012) or can be searched in the internet (e.g. http://www.alanwood.net/pesticides). The classification is based on the current IRAC Mode of Action Classification Scheme at the time of filing of this patent application.

Examples of ectoparasiticides and/or endoparasiticides are insecticides, acaricides and nematicides, and include in particular:

(1) Acetylcholinesterase (AChE) inhibitors, such as, for example, carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel blockers, such as, for example, cyclodiene-organochlorines, for example chlordane and endosulfan or phenylpyrazoles (fiproles), for example ethiprole and fipronil.

(3) Sodium channel modulators, such as, for example, pyrethroids, e.g. acrinathrin, allethrin, d-cis-trans allethrin, d-trans allethrin, bifenthrin, bioallethrin, bioallethrin s-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomer], deltamethrin, empenthrin [(EZ)-(1R)-isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans-isomer], prallethrin, pyrethrins (pyrethrum), resmethrin, silafluofen, tefluthrin, tetramethrin, tetramethrin [(1R)-isomer)], tralomethrin and transfluthrin or DDT or methoxychlor.

(4) Nicotinic acetylcholine receptor (nAChR) competitive modulators, such as, for example, neonicotinoids, e.g. acetamiprid, clothianidin, dinotefuran, imidacloprid, nitenpyram, thiacloprid and thiamethoxam or nicotine or sulfoxaflor or flupyradifurone.

(5) Nicotinic acetylcholine receptor (nAChR) allosteric modulators, such as, for example, spinosyns, e.g. spinetoram and spinosad.

(6) Glutamate-gated chloride channel (GluCl) allosteric modulators, such as, for example, avermectins/milbemycins, for example abamectin, emamectin benzoate, lepimectin and milbemectin.

(7) Juvenile hormone mimics, such as, for example, juvenile hormone analogues, e.g. hydroprene, kinoprene and methoprene or fenoxycarb or pyriproxyfen.

(9) Modulators of Chordotonal Organs, such as, for example pymetrozine or flonicamid.

(10) Mite growth inhibitors, such as, for example clofentezine, hexythiazox and diflovidazin or etoxazole.

(12) Inhibitors of mitochondrial ATP synthase, such as, ATP disruptors such as, for example, diafenthiuron or organotin compounds, for example azocyclotin, cyhexatin and fenbutatin oxide or propargite or tetradifon.

(13) Uncouplers of oxidative phosphorylation via disruption of the proton gradient, such as, for example, chlorfenapyr, DNOC and sulfluramid.

(14) Nicotinic acetylcholine receptor channel blockers, such as, for example, bensultap, cartap hydrochloride, thiocylam, and thiosultap-sodium.

(15) Inhibitors of chitin biosynthesis, type 0, such as, for example, bistrifluron, chlorfluazuron, diflubenzuron, flucycloxuron, flufenoxuron, hexaflumuron, lufenuron, novaluron, noviflumuron, teflubenzuron and triflumuron.

(16) Inhibitors of chitin biosynthesis, type 1, for example buprofezin.

(17) Moulting disruptor (in particular for Diptera, i.e. dipterans), such as, for example, cyromazine.

(18) Ecdysone receptor agonists, such as, for example, chromafenozide, halofenozide, methoxyfenozide and tebufenozide.

(19) Octopamine receptor agonists, such as, for example, amitraz.

(20) Mitochondrial complex III electron transport inhibitors, such as, for example, hydramethylnone or acequinocyl or fluacrypyrim.

(21) Mitochondrial complex I electron transport inhibitors, such as, for example from the group of the METI acaricides, e.g. fenazaquin, fenpyroximate, pyrimidifen, pyridaben, tebufenpyrad and tolfenpyrad or rotenone (Derris).

(22) Voltage-dependent sodium channel blockers, such as, for example indoxacarb or metaflumizone.

(23) Inhibitors of acetyl CoA carboxylase, such as, for example, tetronic and tetramic acid derivatives, e.g. spirodiclofen, spiromesifen and spirotetramat.

(25) Mitochondrial complex II electron transport inhibitors, such as, for example, beta-ketonitrile derivatives, e.g. cyenopyrafen and cyflumetofen and carboxanilides, such as, for example, pyflubumide.

(28) Ryanodine receptor modulators, such as, for example, diamides, e.g. chlorantraniliprole, cyantraniliprole and flubendiamide, further active ingredients such as, for example, Afidopyropen, Afoxolaner, Azadirachtin, Benclothiaz, Benzoximate, Bifenazate, Broflanilide, Bromopropylate, Chinomethionat, Chloroprallethrin, Cryolite, Cyclaniliprole, Cycloxaprid, Cyhalodiamide, Dicloromezotiaz, Dicofol, epsilon-Metofluthrin, epsilon-Momfluthrin, Flometoquin, Fluazaindolizine, Fluensulfone, Flufenerim, Flufenoxystrobin, Flufiprole, Fluhexafon, Fluopyram, Fluralaner, Fluxametamide, Fufenozide, Guadipyr, Heptafluthrin, Imidaclothiz, Iprodione, kappa-Bifenthrin, kappa-Tefluthrin, Lotilaner, Meperfluthrin, Paichongding, Pyridalyl, Pyrifluquinazon, Pyriminostrobin, Spirobudiclofen, Tetramethylfluthrin, Tetraniliprole, Tetrachlorantraniliprole, Tioxazafen, Thiofluoximate, Triflumezopyrim and iodomethane; furthermore preparations based on *Bacillus firmus* (I-1582, BioNeem, Votivo), and also the following compounds: 1-{2-fluoro-4-methyl-5-[(2,2,2-trifluoroethyl)sulphinyl]phenyl}-3-(trifluoromethyl)-1H-1,2,4-triazole-5-amine (known from WO2006/043635) (CAS 885026-50-6), {1'-[(2E)-3-(4-chlorophenyl)prop-2-en-1-yl]-5-fluorospiro[indol-3,4'-piperidin]-1(2H)-yl}(2-chloropyridin-4-yl)methanone (known from WO2003/106457) (CAS 637360-23-7), 2-chloro-N-[2-{1-[(2E)-3-(4-chlorophenyl)prop-2-en-1-yl]piperidin-4-yl}-4-(trifluoromethyl)phenyl]isonicotinamide (known from WO2006/003494) (CAS 872999-66-1), 3-(4-chloro-2,6-dimethylphenyl)-4-hydroxy-8-methoxy-1,8-diazaspiro[4.5]dec-3-en-2-one (known from WO 2010052161) (CAS 1225292-17-0), 3-(4-chloro-2,6-dimethylphenyl)-8-methoxy-2-oxo-1,8-diazaspiro[4.5]dec-3-en-4-yl ethyl carbonate (known from EP2647626) (CAS 1440516-42-6), 4-(but-2-yn-1-yloxy)-6-(3,5-dimethylpiperidin-1-yl)-5-fluoropyrimidine (known from WO2004/099160) (CAS 792914-58-0), PF1364 (known from JP2010/018586) (CAS 1204776-60-2), N-[(2E)-1-[(6-chloropyridin-3-yl)methyl]pyridin-2(1H)-ylidene]-2,2,2-trifluoroacetamide (known from WO2012/029672) (CAS 1363400-41-2), (3E)-3-[1-[(6-chloro-3-pyridyl)methyl]-2-pyridylidene]-1,1,1-trifluoro-propan-2-one (known from WO2013/144213) (CAS 1461743-15-6), N-[3-(benzylcarbamoyl)-4-chlorophenyl]-1-methyl-3-(pentafluoroethyl)-4-(trifluoromethyl)-1H-pyrazole-5-carboxamide (known from WO2010/051926) (CAS 1226889-14-0), 5-bromo-4-chloro-N-[4-chloro-2-methyl-6-(methylcarbamoyl)phenyl]-2-(3-chloro-2-pyridyl)pyrazole-3-carboxamide (known from CN103232431) (CAS 1449220-44-3), 4-[5-(3,5-dichlorophenyl)-4,5-dihydro-5-(trifluoromethyl)-3-isoxazolyl]-2-methyl-N-(cis-1-oxido-3-thietanyl)-benzamide, 4-[5-(3,5-dichlorophenyl)-4,5-dihydro-5-(trifluoromethyl)-3-isoxazolyl]-2-methyl-N-(trans-1-oxido-3-thietanyl)-benzamide and 4-[(5S)-5-(3,5-dichlorophenyl)-4,5-dihydro-5-(trifluoromethyl)-3-isoxazolyl]-2-methyl-N-(cis-1-oxido-3-thietanyl) benzamide (known from WO 2013/050317 A1) (CAS 1332628-83-7), N-[3-chloro-1-(3-pyridinyl)-1H-pyrazol-4-yl]-N-ethyl-3-[(3,3,3-trifluoropropyl)sulfinyl]-propanamide, (+)-N-[3-chloro-1-(3-pyridinyl)-1H-pyrazol-4-yl]-N-ethyl-3-[(3,3,3-trifluoropropyl)sulfinyl]-propanamide and (−)-N-[3-chloro-1-(3-pyridinyl)-1H-pyrazol-4-yl]-N-ethyl-3-[(3,3,3-trifluoropropyl)sulfinyl]-propanamide (known from WO 2013/162715 A2, WO 2013/162716 A2, US 2014/0213448 A1) (CAS 1477923-37-7), 5-[[(2E)-3-chloro-2-propen-1-yl]amino]-1-[2,6-dichloro-4-(trifluoromethyl) phenyl]-4-[(trifluoromethyl)sulfinyl]-1H-pyrazole-3-carbonitrile (known from CN 101337937 A) (CAS 1105672-77-2), 3-bromo-N-[4-chloro-2-methyl-6-[(methylamino)thioxomethyl]phenyl]-1-(3-chloro-2-pyridinyl)-1H-pyrazole-5-carboxamide, (Liudaibenjiaxuanan, known from CN 103109816 A) (CAS 1232543-85-9); N-[4-chloro-2-[[(1,1-dimethylethyl)amino]carbonyl]-6-methylphenyl]-1-(3-chloro-2-pyridinyl)-3-(fluoromethoxy)-1H-Pyrazole-5-carboxamide (known from WO 2012/034403 A1) (CAS 1268277-22-0), N-[2-(5-amino-1,3,4-thiadiazol-2-yl)-4-chloro-6-methylphenyl]-3-bromo-1-(3-chloro-2-pyridinyl)-1H-pyrazole-5-carboxamide (known from WO 2011/085575 A1) (CAS 1233882-22-8), 4-[3-[2,6-dichloro-4-[(3,3-dichloro-2-propen-1-yl)oxy]phenoxy]propoxy]-2-methoxy-6-(trifluoromethyl)-pyrimidine (known from CN 101337940 A) (CAS 1108184-52-6); (2E)- and 2(Z)-2-[2-(4-cyanophenyl)-1-[3-(trifluoromethyl) phenyl]ethylidene]-N-[4-(difluoromethoxy)phenyl]-hydrazinecarboxamide (known from CN 101715774 A) (CAS 1232543-85-9); 3-(2,2-dichloroethenyl)-2,2-dimethyl-4-(1H-benzimidazol-2-yl)phenyl-cyclopropanecarboxylic acid ester (known from CN 103524422 A) (CAS 1542271-46-4); (4aS)-7-chloro-2,5-dihydro-2-[[(methoxycarbonyl)[4-[(trifluoromethyl)thio] phenyl]amino]carbonyl]-indeno[1,2-e][1,3,4]oxadiazine-4a (3H)-carboxylic acid methyl ester (known from CN 102391261 A) (CAS 1370358-69-2); 6-deoxy-3-O-ethyl-2,4-di-O-methyl-, 1-[N-[4-[1-[4-(1,1,2,2,2-pentafluoroethoxy) phenyl]-1H-1,2,4-triazol-3-yl]phenyl]carbamate]-α-L-mannopyranose (known from US 2014/0275503 A1) (CAS 1181213-14-8); 8-(2-cyclopropylmethoxy-4-trifluoromethyl-phenoxy)-3-(6-trifluoromethyl-pyridazin-3-yl)-3-azabicyclo[3.2.1]octane (CAS 1253850-56-4), (8-anti)-8-(2-cyclopropylmethoxy-4-trifluoromethyl-phenoxy)-3-(6-trifluoromethyl-pyridazin-3-yl)-3-aza-bicyclo[3.2.1]octane (CAS 933798-27-7), (8-syn)-8-(2-cyclopropylmethoxy-4-trifluoromethyl-phenoxy)-3-(6-trifluoromethyl-pyridazin-3-yl)-3-aza-bicyclo[3.2.1]octane (known from WO 2007040280 A1, WO 2007040282 A1) (CAS 934001-66-8), N-[3-chloro-1-(3-pyridinyl)-1H-pyrazol-4-yl]-N-ethyl-3-[(3,3,3-trifluoropropyl)thio]-propanamide (known from WO 2015/058021 A1, WO 2015/058028 A1) (CAS 1477919-27-9), N-[4-(aminothioxomethyl)-2-methyl-6-[(methylamino) carbonyl]phenyl]-3-bromo-1-(3-chloro-2-pyridinyl)-1H-pyrazole-5-carboxamide (known from CN 103265527 A) (CAS 1452877-50-7), 5-(1,3-dioxan-2-yl)-4-[[4-(trifluoromethyl)phenyl]methoxy]-pyrimidine (known from WO 2013/115391 A1) (CAS 1449021-97-9), 3-(4-chloro-2,6-dimethylphenyl)-4-hydroxy-8-methoxy-1-methyl-1,8-diazaspiro[4.5]dec-3-en-2-one (known from WO 2010/066780 A1, WO 2011/151146 A1) (CAS 1229023-34-0), 3-(4-chloro-2,6-dimethylphenyl)-8-methoxy-1-methyl-1,8-diazaspiro[4.5]decane-2,4-dione (known from WO 2014/187846 A1) (CAS 1638765-58-8), 3-(4-chloro-2,6-dimethylphenyl)-8-methoxy-1-methyl-2-oxo-1,8-diazaspiro[4.5]dec-3-en-4-yl-carbonic acid ethyl ester (known from WO 2010/066780 A1, WO 2011151146 A1) (CAS 1229023-00-0), N-[1-[(6-chloro-3-pyridinyl)methyl]-2(1H)-pyridinylidene]-2,2,2-trifluoro-acetamide (known from DE 3639877 A1, WO 2012029672 A1) (CAS 1363400-41-2), [N(E)]-N-[1-[(6-chloro-3-pyridinyl)methyl]-2(1H)-pyridinylidene]-2,2,2-trifluoro-acetamide, (known from WO 2016005276 A1) (CAS 1689566-03-7), [N(Z)]—N-[1-[(6-chloro-3-pyridinyl)methyl]-2(1H)-pyridinylidene]-2,2,2-trifluoro-acetamide, (CAS 1702305-40-5), 3-endo-3-[2-propoxy-4-(trifluoromethyl)phenoxy]-9-[[5-(trifluoromethyl)-2-pyridinyl]oxy]-9-azabicyclo[3.3.1]nonane (known from WO 2011/105506 A1, WO 2016/133011 A1) (CAS 1332838-17-1).

Active ingredients with unknown or non-specific mode of action, e.g., fentrifanil, fenoxacrim, cycloprene, chlorobenzilate, chlordimeform, flubenzimine, dicyclanil, amidoflumet, quinomethionate, triarathene, clothiazoben, tetrasul, potassium oleate, petroleum, metoxadiazone, gossyplure, flutenzin, bromopropylate, cryolite.

Active ingredients from other classes, e.g. butacarb, dimetilan, cloethocarb, phosphocarb, pirimiphos (-ethyl), parathion (-ethyl), methacrifos, isopropyl o-salicylate, trichlorfon, sulprofos, propaphos, sebufos, pyridathion, prothoate, dichlofenthion, demeton-S-methylsulphone, isazofos, cyanofenphos, dialifos, carbophenothion, autathiofos, aromfenvinfos (-methyl), azinphos (-ethyl), chlorpyrifos (-ethyl), fosmethilan, iodofenphos, dioxabenzofos, formothion, fonofos, flupyrazofos, fensulfothion, etrimfos;
  organochlorines, e.g. camphechlor, lindane, heptachlor; or phenylpyrazoles, e.g. acetoprole, pyrafluprole, pyriprole, vaniliprole, sisapronil; or isoxazolines, e.g. sarolaner, afoxolaner, lotilaner, fluralaner;
  pyrethroids, e.g. (cis-, trans-), metofluthrin, profluthrin, flufenprox, flubrocythrinate, fubfenprox, fenfluthrin, protrifenbute, pyresmethrin, RU15525, terallethrin, cis-resmethrin, heptafluthrin, bioethanomethrin, biopermethrin, fenpyrithrin, cis-cypermethrin, cis-permethrin, clocythrin, cyhalothrin (lambda-), chlovaporthrin, or halogenated carbonhydrogen compounds (HCHs);
  neonicotinoids, e.g. nithiazine;
  dicloromezotiaz, triflumezopyrim;
  macrocyclic lactones, e.g. nemadectin, ivermectin, latidectin, moxidectin, selamectin, eprinomectin, doramectin, emamectin benzoate; milbemycin oxime;
  triprene, epofenonane, diofenolan;
  Biologicals, hormones or pheromones, for example natural products, e.g. thuringiensin, codlemone or neem components;
  dinitrophenols, e.g. dinocap, dinobuton, binapacryl;
  benzoylureas, e.g. fluazuron, penfluron;
  amidine derivatives, e.g. chlormebuform, cymiazole, demiditraz;
  Bee hive varroa acaricides, for example organic acids, e.g. formic acid, oxalic acid.

Non-limiting examples of insecticides and acaricides of particular interest for use in animal health are and include in particular [i.e. Mehlhorn et al Encyclpaedic Reference of Parasitology 4$^{th}$ edition (ISBN 978-3-662-43978-4)]:
  Effectors at arthropod ligand gated chloride channels: chlordane, heptachlor, endoculfan. Dieldrin, bromocyclen, toxaphene, lindane, fipronil, pyriprole, sisapronil, afoxolaner, fluralaner, sarolaner, lotilaner, fluxametamide, broflanilide, avermectin, doramectin, eprinomectin, ivermectin, milbemycin, moxidectin, selamectin;
  Modulators of arthropod octopaminergic receptors: amitraz, BTS27271, cymiazole, demiditraz;
  Effectors at arthropod voltage-gated sodium channels: DDT, methoxychlor, metaflumizone, indoxacarb, cinerin I, cinerin II, jasmolin I, jasmolin II, pyrethrin I, pyrethrin II, allethrin, alphacypermethrin, bioallethrin, betacyfluthrin, cyfluthrin, cyhalothrin, cypermethrin, deltamethrin, etofenprox, fenvalerate, flucythrinate, flumethrin, halfenprox, permethrin, phenothrin, resmethrin, tau-fluvalinate, tetramethrin;
  Effectors at arthropod nicotinic cholinergic synapses (acetylcholine esterase, acetylcholine receptors): bromoprypylate, bendiocarb, carbaryl, methomyl, promacyl, propoxur, azamethiphos, chlorfenvinphos, chlorpyrifos, coumaphos, cythioate, diazinon, diclorvos, dicrotophos, dimethoate, ethion, famphur, fenitrothion, fenthion, heptenophos, malathion, naled, phosmet, phoxim, phtalofos, propetamphos, temephos, tetrachlorvinphos, trichlorfon, imidacloprid, nitenpyram, dinotefuran, spinosad, spinetoram;
  Effectors on arthropod development processes: cyromazine, dicyclanil, diflubenzuron, fluazuron, lufenuron, triflumuron, fenoxycarb, hydroprene, methoprene, pyriproxyfen, fenoxycarb, hydroprene, S-methoprene, pyriproxyfen.

Exemplary active ingredients from the group of endoparasiticides, as a further or other active ingredient in the present invention, include, without limitation, anthelmintically active compounds and antiprotozoal active compounds.

Anthelmintically active compounds, including, without limitation, the following nematicidally, trematicidally and/or cestocidally active compounds:
  from the class of macrocyclic lactones, for example: eprinomectin, abamectin, nemadectin, moxidectin, doramectin, selamectin, lepimectin, latidectin, milbemectin, ivermectin, emamectin, milbemycin;
  from the class of benzimidazoles and probenzimidazoles, for example: oxibendazole, mebendazole, triclabendazole, thiophanate, parbendazole, oxfendazole, netobimin, fenbendazole, febantel, thiabendazole, cyclobendazole, cambendazole, albendazole-sulphoxide, albendazole, flubendazole;
  from the class of depsipeptides, preferably cyclic depsipetides, in particular 24-membered cyclic depsipeptides, for example: emodepside, PF1022A;
  from the class of tetrahydropyrimidines, for example: morantel, pyrantel, oxantel;
  from the class of imidazothiazoles, for example: butamisole, levamisole, tetramisole;
  from the class of aminophenylamidines, for example: amidantel, deacylated amidantel (dAMD), tribendimidine;
  from the class of aminoacetonitriles, for example: monepantel;
  from the class of paraherquamides, for example: paraherquamide, derquantel;
  from the class of salicylanilides, for example: tribromsalan, bromoxanide, brotianide, clioxanide, closantel, niclosamide, oxyclozanide, rafoxanide;
  from the class of substituted phenols, for example: nitroxynil, bithionol, disophenol, hexachlorophene, niclofolan, meniclopholan;
  from the class of organophosphates, for example: trichlorfon, naphthalofos, dichlorvos/DDVP, crufomate, coumaphos, haloxon;
  from the class of piperazinones/quinolines, for example: praziquantel, epsiprantel;
  from the class of piperazines, for example: piperazine, hydroxyzine;
  from the class of tetracyclines, for example: tetracyclin, chlorotetracycline, doxycyclin, oxytetracyclin, rolitetracyclin;
  from diverse other classes, for example: bunamidine, niridazole, resorantel, omphalotin, oltipraz, nitroscanate, nitroxynile, oxamniquine, mirasan, miracil, lucanthone, hycanthone, hetolin, emetine, diethylcarbamazine, dichlorophen, diamfenetide, clonazepam, bephenium, amoscanate, clorsulon.

Antiprotozoal active ingredients in the present invention, including, without limitation, the following active ingredients:

from the class of triazines, for example: diclazuril, ponazuril, letrazuril, toltrazuril;

from the class of polyether ionophore, for example: monensin, salinomycin, maduramicin, narasin;

from the class of macrocyclic lactones, for example: milbemycin, erythromycin;

from the class of quinolones, for example: enrofloxacin, pradofloxacin;

from the class of quinines, for example: chloroquine;

from the class of pyrimidines, for example: pyrimethamine;

from the class of sulfonamides, for example: sulfaquinoxaline, trimethoprim, sulfaclozin;

from the class of thiamines, for example: amprolium;

from the class of lincosamides, for example: clindamycin;

from the class of carbanilides, for example: imidocarb;

from the class of nitrofuranes, for example: nifurtimox;

from the class of quinazolinone alkaloids, for example: halofuginon;

from diverse other classes, for example: oxamniquin, paromomycin;

from the class of vaccines or antigenes from microorganisms, for example: *Babesia canis rossi, Eimeria tenella, Eimeria praecox, Eimeria necatrix, Eimeria mitis, Eimeria maxima, Eimeria brunetti, Eimeria acervulina, Babesia canis vogeli, Leishmania infantum, Babesia canis canis, Dictyocaulus viviparus.*

All named other or further active ingredients in the present invention can, if their functional groups enable this, optionally form salts with suitable bases or acids.

Based upon standard laboratory techniques known to evaluate compounds useful for the treatment of helminth infections, by standard toxicity tests and by standard pharmacological assays for the determination of treatment of the conditions identified above in animals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the subject treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, it is possible for "drug holidays", in which a subject is not dosed with a drug for a certain period of time, to be beneficial to the overall balance between pharmacological effect and tolerability. Furthermore, it is possible to have long-acting treatments, wherein the subject gets treated once for more than four weeks. It is possible for a unit dosage to contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each subject will vary according to the nature and severity of the condition as determined by the attending diagnostician, the activity of the specific compound employed, the age and general condition of the subject, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

EXPERIMENTAL SECTION

Abbreviations and Acronyms aq. aqueous
atm standard atmosphere
BOP benzotriazol-1-yloxy-tris(dimethylamino)-phosphonium hexafluorophosphonate
brine saturated aqueous sodium chloride
$CDCl_3$ deuterated chloroform
DAD diode array detector
DCM dichloromethane
DMF N,N-dimethylformamide
DMSO dimethyl sulfoxide
$DMSO-d_6$ deuterated dimethyl sulfoxide
ELSD evaporative light scattering detector
ESI electrospray ionization
EtOAc ethyl acetate
g gram
h hour(s)
HBTU (2-(1H-Benzotriazol-1-yl)-1,1,3,3-tetramethyluronium-hexafluorophosphat)
LC-MS liquid chromatography-coupled mass spectrometry
MeOH Methanol
min minute(s)
mg milligram
MTBE methyl-tert-butyl ether
NMR nuclear magnetic resonance spectrometry
p. page(s)
$R_t$ retention time
THF tetrahydrofuran
Tf trifluoromethanesulfonyl
TLC thin layer chromatography The various aspects of the invention described in this application are illustrated by the following examples which are not meant to limit the invention in any way.

The example testing experiments described herein serve to illustrate the present invention and the invention is not limited to the examples given.

EXPERIMENTAL SECTION—GENERAL PART

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartidges KP-Sil® or KP-NH® in combination with a Biotage autopurifier system (SP4® or Isolera Four®) and eluents such as gradients of hexane/EtOAc or DCM/mMeOH. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

Analytical and Chromatography Methods
Analytical and Preparative Liquid Chromatography Analytical (UP)LC-MS was performed by means of different equipments as described below. The masses (m/z) are reported from the positive mode electrospray ionisation unless the negative mode is indicated (ESI−).

M+1 (or M+H) means the molecular ion peak, plus or minus 1 a.m.u. (atomic mass unit) respectively, as observed in mass spectroscopy by electrospray ionization (ESI+ or −).

The determination of $[M+H]^+$ or $M^-$ by LC-MS under acidic chromatographic conditions was done with 1 ml formic acid per liter acetonitrile and 0.9 ml formic acid per liter Millipore water as eluents. A linear gradient from 10% acetonitrile to 95% acetonitrile from 0 to 1.8 minutes is applied and hold constant from 1.80-2.50 minutes at 95:5; oven temperature 55° C. Instruments:

LC-MS (Method L3):

Waters UPLC with SQD2 mass spectrometer and Sample-Manager autosampler. Linear gradient 0.0 to 1.70 minutes from 10% acetonitrile to 95% acetonitrile, from 1.70 to 2.40 minutes constant 95% acetonitrile, flow 0.85 ml/min.

LC-MS (Method L6) and LC-MS (Method L7):

Agilent 1290 LC, Agilent MSD, HTS PAL autosampler. Linear gradient 0.0 to 1.80 minutes from 10% acetonitrile to 95% acetonitrile, from 1.80 to 2.50 minutes constant 95% acetonitrile, flow 1.0 ml/min.

The determination of $[M+H]^+$ by LC-MS under neutral chromatographic conditions was done with acetonitrile and Millipore water containing 79 mg/l ammonia carbonate as eluents. Linear gradient from 10% acetonitrile to 95% acetonitrile. Instruments:

LC-MS (Method L4):

Waters IClass Acquity with QDA mass spectrometer and FTN autosampler (column Waters Acquity 1.7 μm 50 mm*2.1 mm, oven temperature 45° C., flow 0.7 ml/min, gradient 0 (10% ACN)—2.10 min (95% ACN), 2.10-3.00 min constant 95% ACN)

Calibration was done with straight-chain alkan-2-ones (with 3 to 16 carbon atoms) with known log P values (measurement of log P values using retention times with linear interpolation between successive alkanones). Lambda-max-values were determined using UV-spectra from 200 nm to 400 nm and the peak values of the chromatographic signals.

$^1$H-NMR Data $^1$H-NMR data were determined with a Bruker Avance 400 (equipped with a flow cell (60 μl volume), or with a Bruker AVIII 400 equipped with 1.7 mm cryo CPTCI probe head, or with a Bruker AVIII 400 (400.13 MHz) equipped with a 5 mm probe head, or with a Bruker AVII 600 (600.13 MHz) equipped with a 5 mm cryo TCI probe head, or with a Bruker AVIII 600 (601.6 MHz) equipped with a 5 mm cryo CPMNP probe head, or with a Bruker AVIII 500 (500.13 MHz) equipped with a 5 mm broadband head or a 5 mm Prodigy™ probe head, or a Bruker Avance NEO 600 MHz (5 mm TCI cryo probe head), with tetramethylsilane as reference (0.00 ppm) and the solvents $CD_3CN$, $CDCl_3$ or DMSO-$d_6$. Alternative $^1$H- and $^{13}$C-NMR instrument types: Bruker DMX300 ($^1$H-NMR: 300 MHz; $^{13}$C NMR: 75 MHz), Bruker Avance III 400 ($^1$H-NMR: 400 MHz; $^{13}$C NMR: 100 MHz) or Bruker 400 Ultrashield ($^1$H-NMR: 400 MHz; $^{13}$C NMR: 100 MHz).

Chemical shifts (δ) are displayed in parts per million [ppm]; the following abbreviations are used: s=singlet, d=doublet, dd=doublet of doublets, t=triplet, q=quartet, sept=septet, m=multiplet, br=broad; coupling constants are displayed in Hertz [Hz].

EXPERIMENTAL SECTION—GENERAL PROCEDURES

The synthesis of the compounds of the formula (I) can be performed according to or in analogy to the following schemes (Scheme 1, Scheme 2-1 and Scheme 2-2).

Scheme 1

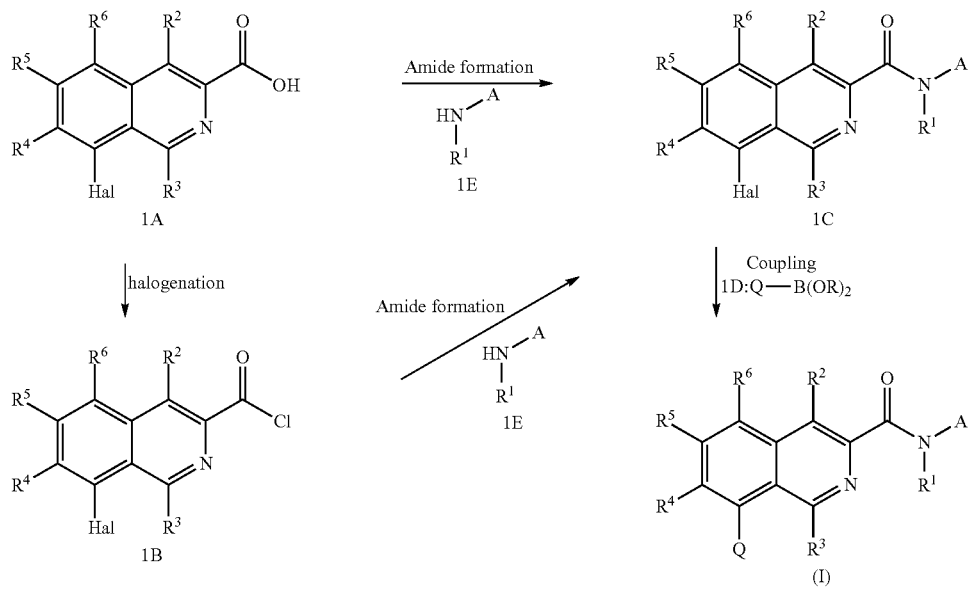

Coupling of carboxylic acids 1A with commercially available amines 1E can proceed via conventional peptide coupling procedures. This coupling reaction is typically conducted using well-known coupling reagents such as N-(3-dimethylaminoisopropyl)-N'-ethylcarbodiimide-hydrochloride (EDC), dicyclohexylcarbodiimide, 2,4,6-tripropyl-1,3,5,2,4,6-trioxatriphosphinane 2,4,6-trioxide, BOP reagent, N,N'-carbonyldiimidazole, HBTU and the like to give amides 1C. Similar syntheses are described in *Chem. Commun.*, 1999, 1847-1848, *J. Org. Chem.*, 1962, 27, 6, 2094-2099, US 20120101125 or WO 2007090068 for example. Suitable solvents are dichloromethane, chloroform, butyl acetate, ethyl acetate, toluene, tetrahydrofuran, dimethoxyethane, 1,4-dioxane, acetonitrile, N,N-dimethylformamide, N,N-dimethylacetamide, dimethyl sulfoxide, nitromethane, pyridine or the like.

Alternatively, the free carboxylic acids 1A can be converted into an acid chloride 1B which is coupled with commercially available amines 1E to provide intermediate carboxamides 1C.

The acid halide 1B can be prepared by contacting the free carboxylic acids 1A with an inorganic acid halide such as phosphorus oxychloride, phosphorus oxide bromide, thionyl chloride, phosphorous pentachloride, oxalyl chloride under conventional conditions. Generally, this reaction is conducted using about 1 to 5 molar equivalents of the inorganic acid halide or oxalyl chloride, either neat or in an inert solvent such as dichloromethane, tetrahydrofuran, toluene or the like, at temperatures in the range of about 0° C. to about 80° C. for about 1 to about 48 hours. A catalyst, such as dimethylformamide, may also be used in this reaction.

The acid chloride 1B is then contacted with at least one equivalent, preferably about 1.1 to about 1.5 equivalents, of commercially available amines 1E, under basic conditions. Suitable bases include, by way of example, tertiary amines such as trimethylamine, or N,N-diisopropylethylamine, N-methyl-morpholine, and the like as described in *Chemical Biology & Drug Design* (2015), 85(5), 549-564 or WO 2007090068. A Suzuki cross-coupling reaction of intermediate carboxamides 1C with commercially available boronic acids or boronic esters 1D Q-B(OR)$_2$ (R=H; R=Me or R,R=pinacolate) in the presence of a palladium catalyst, as described in *Chem. Soc. Rev.*, 2014, 43, 412-443, *Tetrahedron*, 58 (2002), 9633-9695 or in WO 2008148867, leads to the final products of formula (I).

The synthesis of the compounds of formula 1A can be performed according to or in analogy to the following schemes (Scheme 2-1, Scheme 2-2).

Scheme 2-1

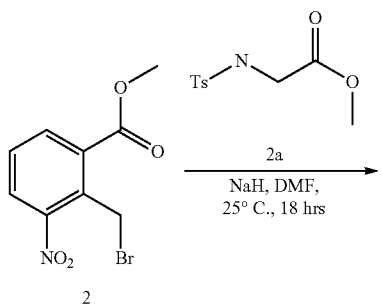

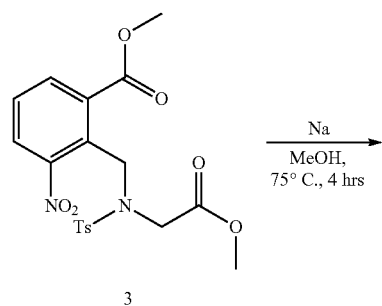

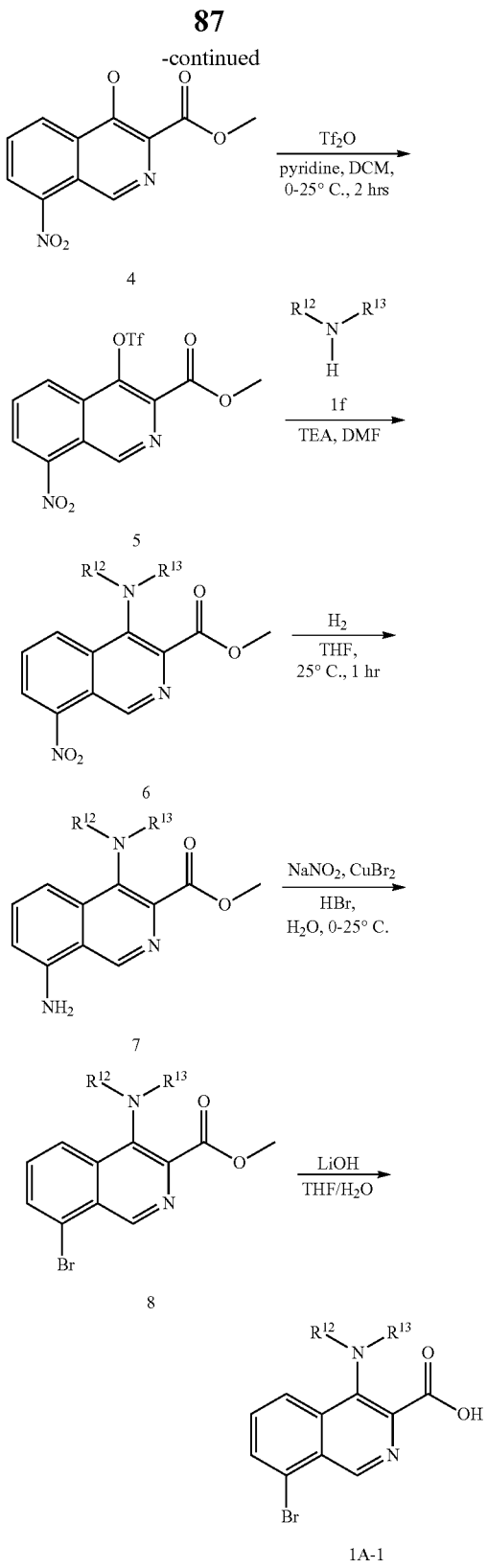

In *J. Chem. Soc.*, Perkin Trans. 1, 2002, 529-532 methyl-1-bromoisoquinoline-3-carboxylate is used as a precursor for a combinatorial approach to the core structure of new potential peripheral benzodiazepine receptor ligands.

A new synthesis of isoquinoline-3-carboxylates based on the palladium(0)-catalysed Heck-type arylation of 2-amido-acrylates with the appropriate 2-substituted iodobenzene is reported in *Tetrahedron Lett.*, 2002, 43(29), 5079-5081.

*Tetrahedron Lett.*, 2002, 43(29), 5079-5081 describes a new and general synthesis of methyl isoquinoline-3-carboxylates starting from aromatic 1,2-dialdehydes by reaction with protected phosphonoglycine derivatives, especially useful for the synthesis of new isoquinolines bearing electron withdrawing groups.

By using the key trifluoromethanesulfonate precursor 5 various substituted isoquinoline-3-carboxylic acids are available. Isoquinoline triflates are preferred building blocks in the preparation of substituted isoquinolines. More examples can be found in J. Med. Chem. 1997, 40, 18, 2910-2921 for example.

Starting from commercially available methyl 2-(bromomethyl)-3-nitrobenzoate 2 which reacts with commercially available methyl N-[(4-methylphenyl)sulfonyl]glycinate 2a intermediate 3 is obtained. The synthesis of similar protected glycine ester compounds is described in WO 2007090068 or US 2006217416.

Compound 3 can be cyclized to the isoquinoline ester 4 by treatment with a suitable base, such as, by way of example, sodium methoxide in methanol or potassium tert-butoxide as described in WO 2007090068.

In analogy to *Ann. Chim.* 1962, 52, 112-120 Compound 4 reacts with triflic anhydride in pyridine to yield key intermediate 5.

Isoquinoline triflate 5 reacts with commercially available amines 1f to yield intermediates 6. After reduction of the nitro group of intermediate 6 the amino group is then converted via the Sandmeyer reaction into the corresponding bromo ester 8. Similar reactions are performed in the course of synthesising 4,5-dibromo isoquinoline as described in *J. Het. Chem.*, 1967, 410-412. The ester intermediates 8 can be easily hydrolysed to the corresponding carboxylic acids 1A-1 with e.g. aqueous sodium hydroxide or lithium hydroxide in appropriate solvents such as alcohols or cyclic ethers as described in WO 2005014533 for example.

The synthesis of substituted isoquinoline-3-carboxylic acids are generally known in the art and are described in US 609373, US 2006217416, WO 2004099206, WO 2004108681, WO 2005014533, WO 2013030358, WO 2016129983 or in US 2007090068.

Scheme 2-2

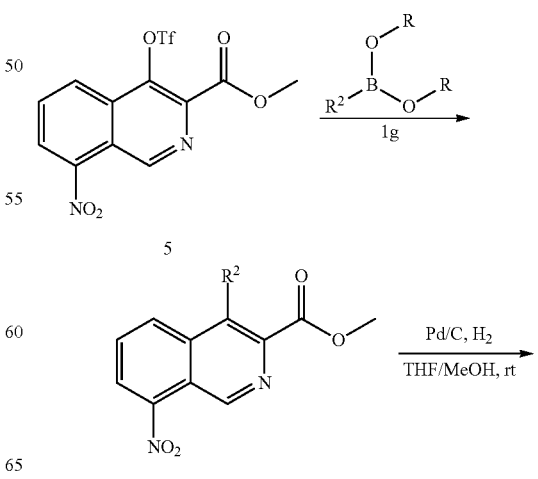

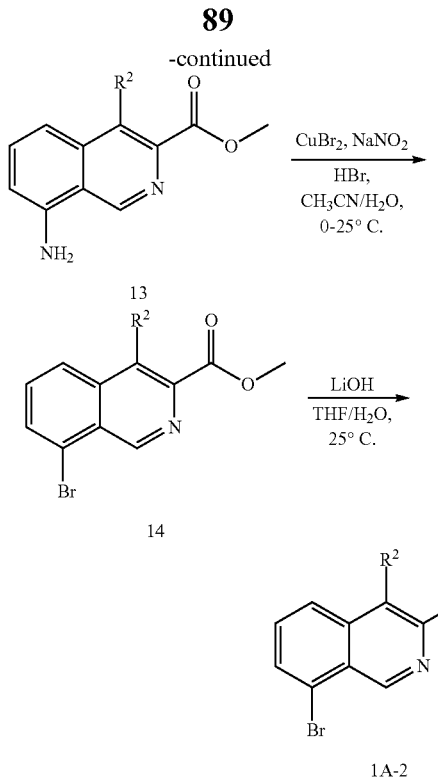

A Suzuki cross-coupling reaction of isoquinoline triflate 5 with commercially available boronic acids or boronic esters 1g $R^2$—B(OR)$_2$ (R=H; R=Me or R,R=pinacolate) as described in *Letters in Organic Chemistry*, 2007, 4 (2), 86-91, *Chem. Soc. Rev.* 2014, 43, 412-443, *Tetrahedron* 2002, 58 (48), 9633-9695 or in WO 2008148867 leads to the nitro intermediates 12.

*Organic Lett.* 2011, 13 (16), 4374-4377 describes the palladium(0)-catalysed reaction of tosylates with boronic acids.

The nitro ester 12 is transformed after hydrogenation and subsequent Sandmeyer reaction of amino ester 13 into the ester intermediates 14 in analogy to *J. Het. Chem.*, 1967, 410-412.

The esters 14 are finally hydrolysed to the carboxylic acids 1A-2 with e.g. aqueous sodium hydroxide or lithium hydroxide in appropriate solvents such as alcohols or cyclic ethers as described in WO 2005014533 for example.

EXPERIMENTAL SECTION—EXAMPLES

Synthesis of N-[(4S)-3,4-dihydro-2H-chromen-4-yl]-4-(morpholin-4-yl)-8-(2,3,5-trifluorophenyl)isoquinoline-3-carboxamide (example I-1)

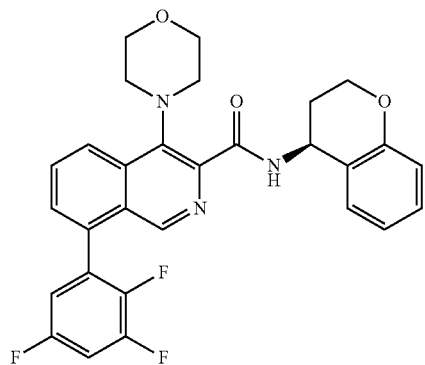 [SMILES: O=C(N[C@H]1CCOc2ccccc21)c1ncc2c(-c3cc(F)cc(F)c3F)cccc2c1N1CCOCC1]

Step 1

Methyl 2-({(2-methoxy-2-oxoethyl)[(4-methylphenyl)sulfonyl]amino}methyl)-3-nitrobenzoate 3

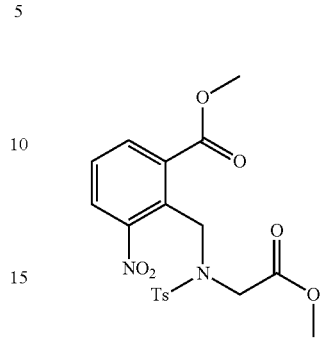

To a mixture of compound 2a methyl N-[(4-methylphenyl)sulfonyl]glycinate (170.0 g, 698.8 mmol, 1 eq) in DMF (425 mL) was added NaH (33.7 g, 841.2 mmol, 60% purity, 1.2 eq) in portions at 25° C. under nitrogen. The mixture was stirred at 25° C. for 2 h, then a solution of commercially available compound 2 methyl 2-(bromomethyl)-3-nitrobenzoate was added (212.8 g, 768.7 mmol, 1.1 eq) in DMF (425 mL). The mixture was stirred at 25° C. for 2 h. The reaction mixture was quenched by addition of 1M HCl (1 L) at 0° C., then diluted with water (1 L) and extracted three times with EtOAc (2 L). The combined organic layers were washed with brine (2 L), dried over Na$_2$SO$_4$, filtered and concentrated under reduced pressure to give a residue, which was purified by column chromatography (SiO$_2$, petroleum ether: EtOAc=50:1 to 2:1) to give compound 3 (289.0 g, 91.5% purity, 86.7% of th.) as a light yellow solid.

LCMS: R$_t$=0.839 min; m/z=437 (M+H)$^+$

Step 2

Methyl 4-hydroxy-8-nitroisoquinoline-3-carboxylate 4

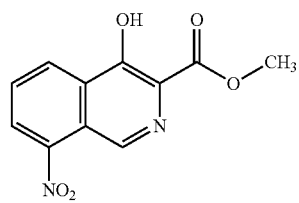 [SMILES: COC(=O)c1ncc2c([N+](=O)[O-])cccc2c1O]

To a mixture of sodium (20.4 g, 886.9 mmol, 3 eq) in MeOH (645 mL) was added compound 3 Methyl 2-({(2-methoxy-2-oxoethyl)[(4-methylphenyl)sulfonyl] amino}methyl)-3-nitrobenzoate (step 1) (129.0 g, 295.6 mmol, 1 eq) under nitrogen. The mixture was stirred at 80° C. for 12 hours. The reaction mixture was concentrated under reduced pressure to remove MeOH. The residue was changed to pH=6-7 by adding 1 N HCl (300 mL), filtered and the filter cake was concentrated under reduced pressure to give compound 4 Methyl 4-hydroxy-8-methylisoquinoline-3-carboxylate (58.35 g, 91.4% purity, 72.7% of th.) as a yellow solid.

LCMS: R$_t$=0.717 min; m/z=249 (M+H)$^+$ $^1$H-NMR (400 MHz, DMSO-d$_6$) δ=11.66 (s, 1H), 9.28 (s, 1H), 8.71 (d, J=8.2 Hz, 1H), 8.62 (dd, 1H), 8.06 (t, J=8.2 Hz, 1H), 4.01 (s, 3H).

Step 3

Methyl 8-nitro-4-{[(trifluoromethyl)sulfonyl]oxy}isoquinoline-3-carboxylate 5

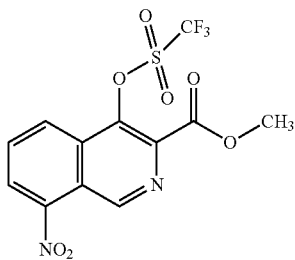 [SMILES: COC(=O)c1ncc2c([N+](=O)[O-])cccc2c1OS(=O)(=O)C(F)(F)F]

To a mixture of compound 4 (step 2) (52.0 g, 209.5 mmol, 1 eq) and pyridine (66.6 g, 842.5 mmol, 68 mL, 4.02 eq) in DCM (260 mL) was added Tf$_2$O (118.0 g, 418.2 mmol, 69 mL, 2 eq) dropwise at 0° C. under nitrogen. The mixture was stirred at 25° C. for 1 hour. The reaction mixture was diluted with water (800 mL) and extracted three times with DCM (1 L). The combined organic layers were washed with brine (1 L), and dried over Na$_2$SO$_4$, filtered and concentrated under reduced pressure to give a residue, which was purified by column chromatography (SiO$_2$, petroleum ether:EtOAc=20:1 to 10:1) to give compound 5 (67.0 g, 99.8% purity, 83.9% of th.) as a light yellow solid.

LCMS: R$_t$=0.821 min; m/z=381 (M+H)$^+$ $^1$H-NMR (400 MHz, CDCl$_3$) δ=10.11 (d, J=1.0 Hz, 1H), 8.63-8.52 (m, 2H), 8.09 (dd, J=7.8, 8.6 Hz, 1H), 4.12 (s, 3H).

Step 4

Methyl 4-(morpholin-4-yl)-8-nitroisoquinoline-3-carboxylate 6

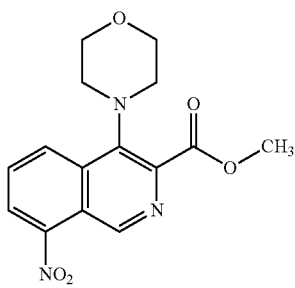 [SMILES: COC(=O)c1ncc2c([N+](=O)[O-])cccc2c1N1CCOCC1]

To a mixture of compound 5 (step 3) (30.0 g, 78.7 mmol, 1 eq) and morpholine (8.23 g, 94.5 mmol, 1.2 eq) in DMF (150 mL) was added TEA (15.9 g, 157.5 mmol, 2 eq) under nitrogen. The mixture was stirred at 80° C. for 2 hours. The reaction mixture was diluted with water (500 mL) and extracted with EtOAc (800 mL). The combined organic layers were washed with brine (500 mL), dried over Na$_2$SO$_4$, filtered and concentrated under reduced pressure to give a residue, which was washed with a mixture of petroleum ether and EtOAc (10:1, 300 mL), then filtered and the filter cake was concentrated under reduced pressure to give compound 6 (24.0 g, 100.0% purity, 96.1% of th.) as a brown solid.

LCMS: R$_t$=0.126 min; m/z=318 (M+H)$^+$ $^1$H-NMR (400 MHz, CDCl$_3$) δ=9.74 (s, 1H), 8.73 (d, J=8.6 Hz, 1H), 8.39 (d, J=7.6 Hz, 1H), 7.88 (t, J=8.2 Hz, 1H), 4.09 (s, 3H), 3.95 (t, J=4.6 Hz, 4H), 3.25 (s, 4H).

Step 5

Methyl 8-amino-4-(morpholin-4-yl)isoquinoline-3-carboxylate 7

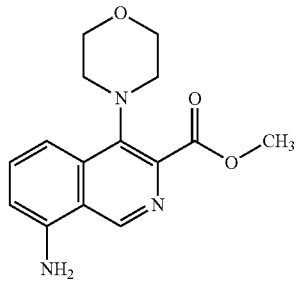 [SMILES: COC(=O)c1ncc2c(N)cccc2c1N1CCOCC1]

To a solution of compound 6 (step 4) (12.0 g, 37.8 mmol, 1 eq) in THF (60 mL) was added wet Pd/C (10%, 1.20 g) under nitrogen. The suspension was degassed under vacuum and purged with H$_2$ several times. The mixture was stirred under H$_2$ (15 psi) at 25° C. for 1 hour. The reaction mixture was filtered and the filtrate was concentrated under reduced pressure to give compound 7 (10.0 g, 99.2% purity, 91.3% of th.) as a brown solid.

LCMS: R$_t$=0.595 min; m/z=288 (M+H)$^+$ $^1$H-NMR (400 MHz, CDCl$_3$) δ=9.08 (d, J=0.8 Hz, 1H), 7.71 (d, J=8.4 Hz, 1H), 7.55 (dd, 1H), 7.27 (s, 1H), 6.88 (dd, 1H), 4.05 (s, 3H), 3.91 (t, J=4.6 Hz, 4H), 3.23 (s, 4H).

Step 6

Methyl 8-bromo-4-(morpholin-4-yl)isoquinoline-3-carboxylate, HBr salt 8

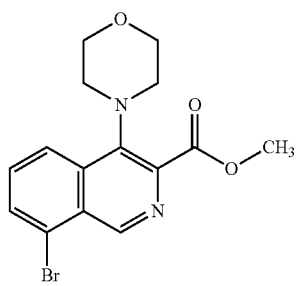 [SMILES: COC(=O)c1ncc2c(Br)cccc2c1N1CCOCC1]

To a mixture of compound 7 (step 5) (15.0 g, 51.8 mmol, 1 eq) in HBr (75 mL), water (30 mL) and MeCN (75 mL) was added a solution of NaNO$_2$ (4.64 g, 67.3 mmol, 1.3 eq) in water (30 mL) at 0° C. The mixture was stirred at 0° C. for 0.5 hour, then was added into a solution of CuBr$_2$ (6.95 g, 31.1 mmol, 0.6 eq) in HBr (120 mL) at 0° C. The mixture was stirred at 25° C. for 1 hour. The reaction mixture was poured into water (2 L) slowly, and filtered and the filter cake was concentrated under reduced pressure to give compound 8 (13.3 g as HBr salt, 81.1% purity, 48.2% of th.) as a brown solid.

LCMS: R$_t$=0.917 min; m/z=352 (M+H)$^+$ $^1$H-NMR (400 MHz, DMSO-d$_6$) δ=9.67-8.91 (m, 1H), 8.35 (d, J=8.4 Hz, 1H), 8.09 (d, J=7.4 Hz, 1H), 7.78 (t, J=8.0 Hz, 1H), 3.96 (s, 3H), 3.83-3.77 (m, 4H), 3.13-3.05 (m, 4H).

Step 7

8-Bromo-4-(morpholin-4-yl)isoquinoline-3-carboxylic acid 1A-3

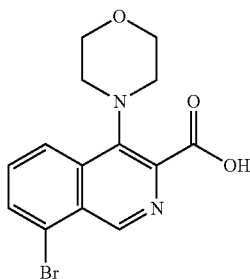 [SMILES: O=C(O)c1ncc2c(Br)cccc2c1N1CCOCC1]

To a mixture of compound 8 (step 6) (15.0 g, 34.7 mmol, 1 eq, HBr salt) in water (15 mL), THF (30 mL) and MeOH (30 mL) was added lithium hydroxide monohydrate (7.28 g, 173.6 mmol, 5 eq). The mixture was stirred at 40° C. for 1 hour. The reaction mixture was changed to pH=3-4 by addition of 1 M HCl (150 mL), and then extracted with DCM (200 mL*3). The combined organic layers were washed with brine (500 mL), dried over $Na_2SO_4$, filtered and concentrated under reduced pressure to give 1A-3 (5.50 g, 96.5% purity, 45.4% of th.) as a yellow solid.

LCMS: $R_t$=0.680 min; m/z=339 (M+H)$^+$ $^1$H-NMR (400 MHz, DMSO-d$_6$) δ=13.59 (s, 1H), 9.23 (s, 1H), 8.35 (s, 1H), 8.06 (s, 1H), 7.76 (s, 1H), 3.82 (s, 4H), 3.15 (s, 4H).

Step 8

8-Bromo-N-[(4S)-3,4-dihydro-2H-chromen-4-yl]-4-(morpholin-4-yl)quinoline-3-carboxamide 1C-1

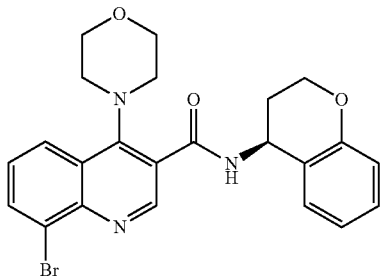 [SMILES: O=C(N[C@H]1CCOc2ccccc21)c1cnc2c(Br)cccc2c1N1CCOCC1]

To a suspension of 1A-3 (step 7) 8-bromo-4-(morpholin-4-yl)isoquinoline-3-carboxylic acid (1.0 g, 2.97 mmol) in dry toluene (25 mL) was added 2 drops of DMF. Then thionyl chloride (530 mg, 4.46 mmol) was added tropwise within 2 minutes. After stirring for 3 h at 70° C. the mixture was concentrated in vacuo, and after adding THF (25 mL), (S)-chroman-4-amine hydrochloride (550 mg, 2.96 mmol) and N,N-diisopropylethylamine (1.3 g, 10 mmol) stirring was continued overnight at room temperature.

Solvents were removed under reduced pressure and the residue was partitioned between water (50 mL) and DCM (50 mL). The combined organic layers were dried via a sodium sulfate/silica gel cartridge and concentrated in vacuo. Purification by flash chromatography with an EtOAc/cyclohexane gradient afforded 410 mg (97.6% purity, 28.8% of th.) of the title compound.

LC-MS (Method L3): Index=923; m/z=469 (M+H)$^+$ $^1$H-NMR (400 MHz, DMSO-d$_6$) δ=9.25 (s, 1H), 9.03-9.01 (m, 1H), 8.39-8.37 (m, 1H), 8.06-8.04 (m, 1H), 7.78-7.74 (m, 1H), 7.36-7.34 (m, 1H), 7.20-7.15 (m, 1H), 6.95-6.91 (m, 1H), 6.81-6.79 (m, 1H), 5.31 (m, 1H), 4.30-4.27 (m, 2H), 3.87-3.78 (m, 4H), 3.20-3.17 (m, 4H), 2.23-2.18 (m, 1H), 2.12-2.06 (m, 1H).

Step 9

N-[(4S)-3,4-dihydro-2H-chromen-4-yl]-4-(morpholin-4-yl)-8-(2,3,5-trifluorophenyl)isoquinoline-3-carboxamide (example I-1)

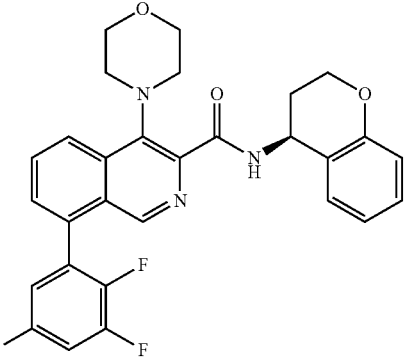

A mixture of 8-Bromo-N-[(4S)-3,4-dihydro-2H-chromen-4-yl]-4-(morpholin-4-yl)quinoline-3-carboxamide (step 8) (100 mg, 0.214 mmol) and bis(triphenylphosphine)dichloropalladium(II) (14 mg, 0.02 mmol) in 1,4-dioxane (10 mL) was stirred at room temperature for 2 h. After the addition of (2,3,5-trifluorophenyl)boronic acid (80 mg, 0.455 mmol), sodium carbonate (230 mg, 2.17 mmol) and water (0.85 mL) stirring was continued for 18 h at 90° C. The mixture was cooled to room temperature, water was added and the aqueous layer was extracted with DCM (3×20 mL). Solvents were dried and removed under reduced pressure. Purification by flash chromatography with an EtOAc/cyclohexane gradient afforded 27 mg (94.5% purity, 23% of th.) of the title compound.

LC-MS (Method L6): Index=1019; m/z=520 (M+H)$^+$ $^1$H-NMR (400 MHz, DMSO-d$_6$) δ=8.99-8.97 (m, 1H), 8.76-8.75 (m, 1H), 8.50-8.48 (m, 1H), 7.98-7.96 (m, 1H), 7.75-7.72 (m, 2H), 7.34-7.32 (m, 2H), 7.18-7.14 (m, 1H), 6.93-6.89 (m, 1H), 6.80-6.78 (m, 1H), 5.31 (m, 1H), 4.29-4.26 (m, 2H), 3.90-3.81 (m, 4H), 3.21 (m, 4H), 2.19-2.07 (m, 2H).

Intermediate 1A-4 has been prepared as a yellow solid in a similar way as described in step 7.

8-Bromo-4-(dimethylamino)isoquinoline-3-carboxylic acid 1A-4

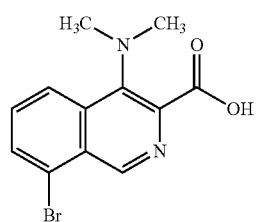 [SMILES: CN(C)c1c(C(=O)O)ncc2c(Br)cccc12]

LCMS: $R_t$=0.722 min; m/z=295 (M)$^+$ $^1$H-NMR (400 MHz, DMSO-d$_6$) δ=9.19 (s, 1H), 8.28 (d, J=8.6 Hz, 1H), 8.05 (d, J=7.0 Hz, 1H), 7.74 (t, J=8.4 Hz, 1H), 2.94 (s, 6H).

Synthesis of N-[(4S)-3,4-dihydro-2H-chromen-4-yl]-4-methyl-8-(2,3,5-trifluorophenyl)isoquinoline-3-carboxamide (example I-2)

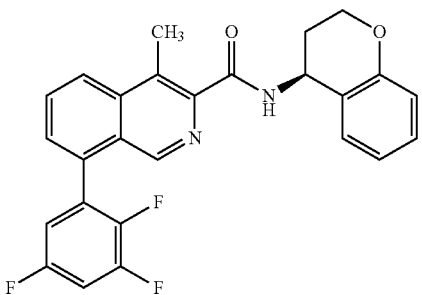 [SMILES: Cc1c(C(=O)N[C@H]2CCOc3ccccc32)ncc2c(-c3cc(F)cc(F)c3F)cccc12]

Step 1

Methyl 4-methyl-8-nitroisoquinoline-3-carboxylate 12

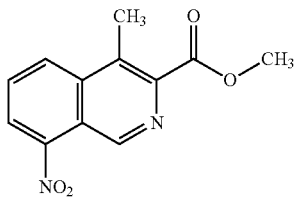

A mixture of methyl 8-nitro-4-{[(trifluoromethyl)sulfonyl]oxy}isoquinoline-3-carboxylate 5 (30.0 g, 78.9 mmol, 1.00 eq), methylboronic acid (14.2 g, 237 mmol, 3.00 eq), $K_3PO_4$ (67.0 g, 316 mmol, 4.00 eq) and Pd(dppf)Cl$_2$ (5.77 g, 7.89 mmol, 0.10 eq) was degassed under vacuum and purged with nitrogen 3 times. The reaction mixture was filtered through a pad of celite. The filtrate was concentrated under reduced pressure. The residue was triturated with petroleum ether/EtOAc/DCM (100 mL/100 mL/30 mL) to give compound 12 (17.0 g, 97.3% purity, 85.2% of th.) as a brown solid.

LCMS: $R_t$=0.889 min; m/z=247 (M+H)$^+$ $^1$H-NMR (400 MHz, DMSO-d$_6$) δ=9.60 (s, 1H), 8.66 (d, J=8.8 Hz, 1H), 8.53 (d, J=7.6 Hz, 1H), 8.08 (t, J=8.0 Hz, 1H), 3.95 (s, 3H), 2.79 (s, 3H).

Step 2

Methyl 8-amino-4-methylisoquinoline-3-carboxylate 13

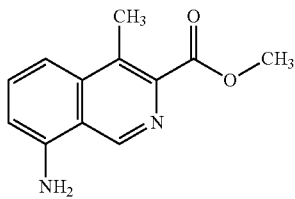

To a solution of compound 12 (step 1) (17.0 g, 69.0 mmol, 1.00 eq) in THF (63.0 mL)/MeOH (21.0 mL) was added Pd/C (10.0 g, 10.0% purity). The reaction mixture was degassed under vacuum and purged with hydrogen 3 times. The reaction mixture was stirred at 20° C. under H$_2$ (15 Psi) for 5 hrs. The reaction mixture was filtered through a pad of celite. The filter cake was washed with MeOH (100 mL) and the filtrate was concentrated under vacuum to give compound 13 (15.2 g, 93.6% purity, 95.3% of th.) as a yellow solid.

LCMS: $R_t$=0.857 min; m/z=217 (M+H)$^+$ $^1$H-NMR (400 MHz, DMSO-d$_6$) δ=9.35 (s, 1H), 7.56-7.52 (m, 1H), 7.25 (t, J=8.4 Hz, 1H), 6.86 (d, J=7.6 Hz, 1H), 6.39 (s, 2H), 3.92 (s, 3H), 2.60 (s, 3H).

Step 3

Methyl 8-bromo-4-methylisoquinoline-3-carboxylate 14

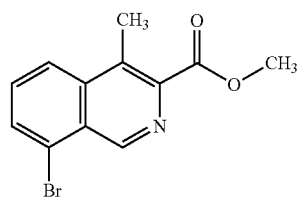 [SMILES: COC(=O)c1ncc2c(Br)cccc2c1C]

To a mixture of compound 13 (step 2) (11.4 g, 52.7 mmol, 1.00 eq) in HBr (50.0 mL, 40% purity)/water (20.0 mL)/CH$_3$CN (50.0 mL) cooled to 0° C., NaNO$_2$ (4.73 g, 68.6 mmol, 1.30 eq) in water (20.0 mL) was added and the mixture was stirred at 0° C. for 30 minutes, then the mixture was added to CuBr$_2$ (7.64 g, 34.2 mmol, 1.60 mL, 0.65 eq) in HBr (75 mL, 40% purity) at 25° C. and stirred at 25° C. for 1 hr. The reaction mixture was poured into water (200 mL), adjusted to pH=10 with 10% aqueous NaOH, extracted with DCM (500 mL) and separated. The organic phase was dried over Na$_2$SO$_4$, filtered and concentrated in vacuo. The residue was purified by silica gel chromatography (petroleum ether:EtOAc:DCM=6:1:0.2~3:1:0.2) to give compound 14 (3.20 g, 98.5% purity, 21.2% of th.) as a yellow solid.

LCMS: $R_t$=0.868 min; m/z=281 (M+H)$^+$

Step 4

8-Bromo-4-methylisoquinoline-3-carboxylic acid 1A-5

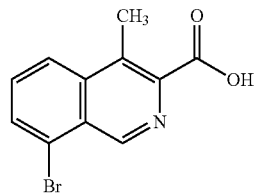

To a solution of compound 14 (step 3) (3.20 g, 11.4 mmol, 1.00 eq) in water (30.0 mL)/THF (30.0 mL) was added lithium hydroxide monohydrate (1.92 g, 45.7 mmol, 4.00 eq). The reaction mixture was stirred at 25~30° C. for 3 hrs. The reaction mixture was concentrated in vacuo. The residue was diluted with water (200 mL), adjusted to pH=3~4 with 4 N HCl, a yellow precipitate appeared. The mixture was filtered and the filter cake was dried in vacuo to give 1A-5 (2.50 g, 99.6% purity, 82.2% of th.) as a yellow solid.

LCMS: $R_t$=0.668 min; m/z=266 (M)⁺

¹H-NMR (400 MHz, DMSO-d₆) δ=13.4 (brs, 1H), 9.37 (s, 1H), 8.28 (d, J=8.4 Hz, 1H), 8.13-8.07 (m, 1H), 7.81 (t, J=8.0 Hz, 1H), 2.78 (s, 3H).

Step 5

8-Bromo-N-[(4S)-3,4-dihydro-2H-chromen-4-yl]-4-methylisoquinoline-3-carboxamide 1C-2

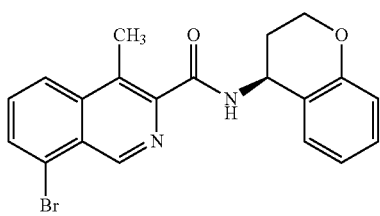 [SMILES: Cc1c(C(=O)N[C@H]2CCOc3ccccc32)ncc2c(Br)cccc12]

A suspension of 8-bromo-4-methylisoquinoline-3-carboxylic acid (step 4) (400 mg, 1.50 mmol) and di-1H-imidazol-1-ylmethanone (265 mg, 1.63 mmol) in dry THF (15 mL) was stirred overnight at 60° C. After adding (S)-chroman-4-amine hydrochloride (283 mg, 1.52 mmol) and N,N-diisopropylethylamine (900 mg, 6.96 mmol) stirring was continued overnight at 60° C.

Solvents were removed under reduced pressure and the residue was partitioned between water (50 mL) and DCM (50 mL). The combined organic layers were dried via a sodium sulfate/silica gel cartridge and concentrated in vacuo and yielded 375 mg (95% purity according to 1H-NMR, 62.8% of th.) of the title compound.

LC-MS (Method L3): Index=1027; m/z=398 (M+H)⁺

¹H-NMR (400 MHz, DMSO-d₆) δ=9.36 (s, 1H), 9.05-9.03 (m, 1H), 8.30-8.28 (m, 1H), 8.10-8.08 (m, 1H), 7.82-7.78 (m, 1H), 7.30-7.28 (m, 1H), 7.19-7.15 (m, 1H), 6.93-6.89 (m, 1H), 6.81-6.79 (m, 1H), 5.35-5.30 (m, 1H), 4.29-4.26 (m, 2H), 2.86 (s, 3H), 2.21-2.10 (m, 2H).

Step 6

N-[(4S)-3,4-dihydro-2H-chromen-4-yl]-4-methyl-8-(2,3,5-trifluorophenyl)isoquinoline-3-carboxamide (example I-2)

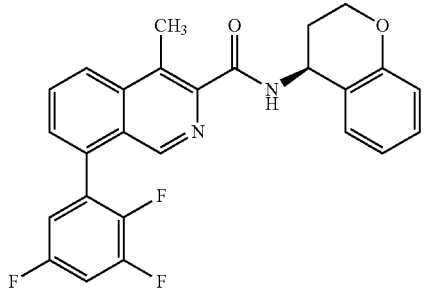 [SMILES: Cc1c(C(=O)N[C@H]2CCOc3ccccc32)ncc2c(-c3cc(F)cc(F)c3F)cccc12]

A mixture of 8-Bromo-N-[(4S)-3,4-dihydro-2H-chromen-4-yl]-4-methylisoquinoline-3-carboxamide (step 5) (150 mg, 0.378 mmol) and bis(triphenylphosphine)dichloropalladium(II) (36 mg, 0.051 mmol) in 1,4-dioxane (20 mL) was stirred at room temperature for 2 h. After the addition of (2,3,5-trifluorophenyl)boronic acid (275 mg, 1.56 mmol), sodium carbonate (730 mg, 6.89 mmol) and water (1.05 mL) stirring was continued for 18 h at 90° C. The mixture was cooled to room temperature, water was added and the aqueous layer was extracted with DCM (3×20 mL). Solvents were dried and removed under reduced pressure. Purification by flash chromatography with an EtOAc/cyclohexane gradient afforded 111 mg (100% purity, 65.6% of th.) of the title compound.

LC-MS (Method L3): Index=1109; m/z=449 (M+H)⁺

¹H-NMR (400 MHz, DMSO-d₆) δ=9.00-8.97 (m, 1H), 8.85 (m, 1H), 8.40-8.38 (m, 1H), 8.02-7.99 (m, 1H), 7.78-7.71 (m, 2H), 7.36 (br, 1H), 7.28-7.26 (m, 1H), 7.18-7.14 (m, 1H), 6.91-6.87 (m, 1H), 6.80-6.78 (m, 1H), 5.33-5.28 (m, 1H), 4.28-4.25 (m, 2H), 2.92 (s, 3H), 2.20-2.08 (m, 2H).

Synthesis of N-[(4S)-3,4-dihydro-2H-chromen-4-yl]-4-isopropyl-8-(2,3,5-trifluorophenyl)isoquinoline-3-carboxamide (example I-3)

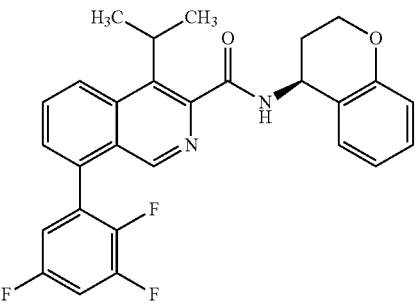 [SMILES: CC(C)c1c(C(=O)N[C@H]2CCOc3ccccc32)ncc2c(-c3cc(F)cc(F)c3F)cccc12]

Step 1

Methyl 8-nitro-4-(prop-1-en-2-yl)isoquinoline-3-carboxylate 15

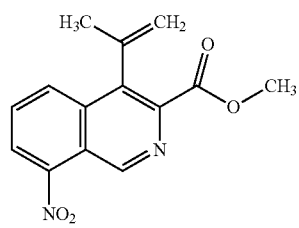 [SMILES: C=C(C)c1c(C(=O)OC)ncc2c([N+](=O)[O-])cccc12]

A mixture of methyl 8-nitro-4-{[(trifluoromethyl)sulfonyl]oxy}isoquinoline-3-carboxylate 5 (30.0 g, 78.9 mmol, 1 eq), potassium trifluoro(prop-1-en-2-yl)borate (23.4 g, 158 mmol, 2 eq), Pd(dppf)Cl₂ (5.50 g, 7.52 mmol, 0.095 eq), Na₂CO₃ (25.1 g, 237 mmol, 3.01 eq) in dioxane (150 mL) was degassed and purged with nitrogen, and then the mixture was stirred at 70° C. for 2 hr under a nitrogen atmosphere. The reaction mixture was filtered through a pad of celite. The filtrate was concentrated under reduced pressure to leave a residue which was stirred in petroleum ether/EtOAc (1:1, 150 mL) for 0.5 hr. The precipitate was filtered and dried to give compound 15 (18.5 g, 99.0% purity, 85.3% of th.) as a brown solid.

LCMS: $R_t$=0.87 min; m/z=273 (M+H)⁺

$^1$H-NMR (400 MHz, CDCl$_3$) δ=9.98 (s, 1H), 8.42 (d, J=7.6 Hz, 2H), 7.88 (t, J=8.0 Hz, 1H), 5.58-5.53 (m, 1H), 5.00 (m, 1H), 4.02 (s, 3H), 2.28 (s, 3H).

Step 2

Methyl 8-amino-4-(prop-1-en-2-yl)isoquinoline-3-carboxylate 16

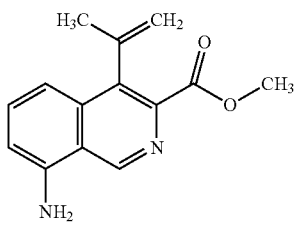 [SMILES: C=C(C)c1c(C(=O)OC)ncc2c(N)cccc12]

To a solution of methyl 8-nitro-4-(prop-1-en-2-yl)isoquinoline-3-carboxylate 15 (step 1) (18.0 g, 65.4 mmol, 1 eq) in THF (90.0 mL) and MeOH (90.0 mL) was added Pd/C (5.00 g, 10% purity, 1.00 eq) under nitrogen. The suspension was degassed under vacuum and purged with H$_2$ several times. The mixture was stirred under H$_2$ (15 psi) at 20° C. for 5 hours. The mixture was filtered through a pad of celite and the filtrate was concentrated to give compound 16 (16.5 g, 92.9% purity, 95.7 of th.) as an orange solid.

LCMS: R$_t$=0.61 min; m/z=243 (M+H)$^+$

Step 3

Methyl 8-amino-4-isopropylisoquinoline-3-carboxylate 17

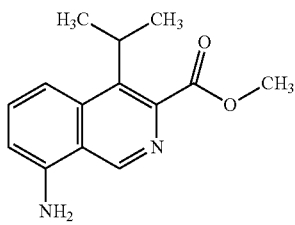 [SMILES: COC(=O)c1ncc2c(N)cccc2c1C(C)C]

To a solution of compound 16 (step 2) (16.5 g, 68.1 mmol, 1 eq) in MeOH (100 mL) and THF (50.0 mL) was added PtO$_2$ (1.65 g, 7.27 mmol, 0.107 eq) under nitrogen. The suspension was degassed under vacuum and purged with H$_2$ several times. The mixture was stirred under H$_2$ (15 psi) at 35° C. for 5 hours. The reaction mixture was filtered through a pad of celite and the filtrate was concentrated under reduced pressure to give compound 17 (16.4 g, 93.0% purity, 91.7 of th.) as a yellow solid.

LCMS: R$_t$=0.671 min; m/z=245 (M+H)$^+$

Step 4

Methyl 8-bromo-4-isopropylisoquinoline-3-carboxylate 18

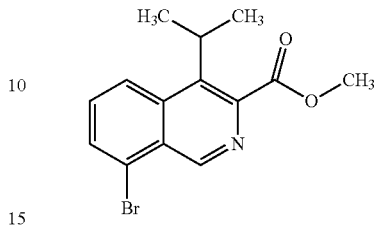

To a solution of compound 17 (step 3) (15.8 g, 64.7 mmol, 1.00 eq) in HBr (50.0 mL) and CH$_3$CN (50.0 mL) was added a solution of NaNO$_2$ (5.37 g, 77.9 mmol, 1.20 eq) in water (20.0 mL) at −5~0° C. The mixture was stirred at 0° C. for 0.5 hr. Then the reaction mixture was added to a solution of CuBr$_2$ (7.24 g, 32.4 mmol, 1.52 mL, 0.501 eq) in HBr (20.0 mL) at 20° C. The resulting mixture was stirred at 20~25° C. for 0.5 hr. The mixture was poured into water (200 mL) and diluted with DCM (150 mL). To the mixture was added 10% NaOH to adjust to pH 8~9. The organic phase was separated, washed with brine (100 mL), dried over anhydrous Na$_2$SO$_4$, filtered and concentrated in vacuum to give a residue which was purified by column chromatography (SiO$_2$, petroleum ether/EtOAc=10/1 to 4/1, R$_f$=0.6 was collected) to give compound 18 (7.40 g, 94.2% purity, 35% of th.) as a light brown oil.

LCMS: R$_t$=0.918 min; m/z=308 (M)$^+$ $^1$H-NMR (400 MHz, CDCl$_3$) δ=9.53 (s, 1H), 8.30 (d, J=8.4 Hz, 1H), 7.90 (d, J=7.6 Hz, 1H), 7.59 (dd, J=7.6, 8.8 Hz, 1H), 4.03 (s, 3H), 3.83 (m, 1H), 1.56 (d, J=7.2 Hz, 6H).

Step 5

8-Bromo-4-isopropylisoquinoline-3-carboxylic acid 1A-6

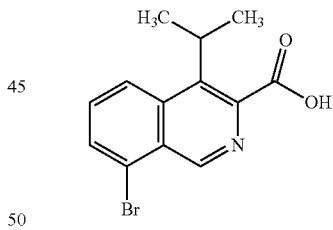

To a solution of compound 18 (step 4) (6.3 g, 19.26 mmol, 1.00 eq) in THF (20.0 mL), MeOH (10.0 mL) and water (30.0 mL) was added lithium hydroxide monohydrate (2.42 g, 57.8 mmol, 3.00 eq). The mixture was stirred at 20~25° C. for 2 hr. The reaction mixture was concentrated under reduced pressure to ~40.0 mL. Water (50.0 mL) and DCM (100 mL) was added. To the resulting mixture was added 4N HCl to adjust to pH 3~4. The organic phase was separated, washed two times with brine (50.0 mL), dried over Na$_2$SO$_4$, filtered and concentrated under reduced pressure to give 1A-6 (5.80 g, 95.9% purity, 98.2 of th.) as a brown solid.

LCMS: R$_t$=0.699 min; m/z=295 (M+H)$^+$ $^1$H-NMR (400 MHz, CDCl$_3$) δ=9.72 (br s, 1H), 9.46 (s, 1H), 8.52 (d, J=8.8 Hz, 1H), 8.00 (d, J=7.6 Hz, 1H), 7.66 (dd, J=7.6, 8.8 Hz, 1H), 5.34-5.23 (m, 1H), 1.61 (d, J=7.2 Hz, 6H).

Step 6

8-Bromo-N-[(4S)-3,4-dihydro-2H-chromen-4-yl]-4-isopropylisoquinoline-3-carboxamide 1C-3

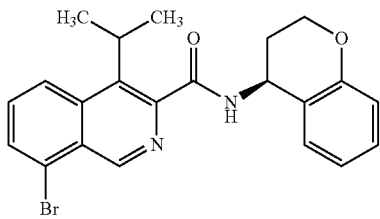 [SMILES: CC(C)c1c(C(=O)N[C@H]2CCOc3ccccc32)ncc2c(Br)cccc12]

To a suspension of 8-bromo-4-isopropylisoquinoline-3-carboxylic acid (step 5) (500 mg, 1.70 mmol) in dry toluene (20 mL) was added 2 drops of DMF. Then thionyl chloride (430 mg, 3.61 mmol) was added tropwise within 2 minutes. After stirring for 3 h at 70° C. the mixture was concentrated in vacuo, and after adding THF (20 mL), (S)-chroman-4-amine hydrochloride (320 mg, 1.72 mmol) and N,N-diisopropylethylamine (1.0 g, 7.74 mmol) stirring was continued overnight at room temperature.

Solvents were removed under reduced pressure and the residue was partitioned between water (50 mL) and DCM (50 mL). The combined organic layers were dried via a sodium sulfate/silica gel cartridge and concentrated in vacuo. Purification by flash chromatography with an EtOAc/cyclohexane gradient afforded 193 mg (100% purity, 26.7% of th.) of the title compound.

LC-MS (Method 3): Index=1000; m/z=426 (M+H)$^+$ $^1$H-NMR (400 MHz, DMSO-d$_6$) δ=9.37 (s, 1H), 8.98-8.96 (m, 1H), 8.44-8.42 (m, 1H), 8.06-8.04 (m, 1H), 7.76-7.72 (m, 1H), 7.33-7.31 (m, 1H), 7.19-7.15 (m, 1H), 6.95-6.91 (m, 1H), 6.80-6.78 (m, 1H), 5.32-5.30 (m, 1H), 4.28-4.25 (m, 2H), 3.82 (sept, 1H), 2.20-2.16 (m, 1H), 2.08-2.04 (m, 1H), 1.53 (dd, 6H).

Step 7

N-[(4S)-3,4-dihydro-2H-chromen-4-yl]-4-isopropyl-8-(2,3,5-trifluorophenyl)isoquinoline-3-carboxamide (example I-3)

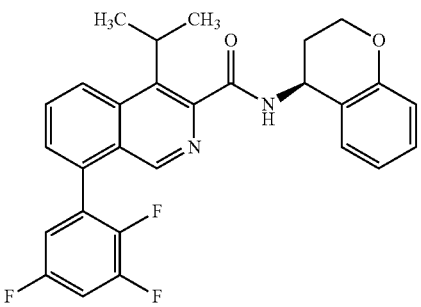 [SMILES: CC(C)c1c(C(=O)N[C@H]2CCOc3ccccc32)ncc2c(-c3cc(F)cc(F)c3F)cccc12]

A mixture of 8-bromo-N-[(4S)-3,4-dihydro-2H-chromen-4-yl]-4-isopropylisoquinoline-3-carboxamide (step 6) (90 mg, 0.212 mmol) and bis(triphenylphosphine)dichloropalladium(II) (12 mg, 0.017 mmol) in 1,4-dioxane (10 mL) was stirred at room temperature for 2 h. After the addition of (2,3,5-trifluorophenyl)boronic acid (50 mg, 0.284 mmol), sodium carbonate (220 mg, 2.08 mmol) and water (0.65 mL) stirring was continued for 18 h at 90° C. The mixture was cooled to room temperature, water was added and the aqueous layer was extracted with DCM (3×20 mL). Solvents were dried and removed under reduced pressure. Purification by flash chromatography with an EtOAc/cyclohexane gradient yielded 17 mg (95% purity, 16% of th.) of the title compound.

LC-MS (Method 3): Index=1091; m/z=477 (M+H)$^+$ $^1$H-NMR (400 MHz, DMSO-d$_6$) δ=8.95-8.93 (m, 1H), 8.83 (m, 1H), 8.53-8.51 (m, 1H), 7.95-7.91 (m, 1H), 7.77-7.69 (m, 2H), 7.33-7.29 (m, 2H), 7.17-7.13 (m, 1H), 6.93-6.89 (m, 1H), 6.79-6.77 (m, 1H), 5.33-5.29 (m, 1H), 4.27-4.25 (m, 2H), 3.90-3.84 (sept, 1H), 2.20-2.14 (m, 1H), 2.06-2.01 (m, 1H), 1.57 (dd, 6H).

TABLE 1

Examples

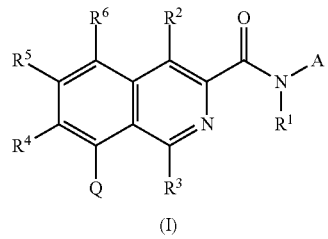

(I)

| Number | R1 | R2 | R3 | R4 | R5 | R6 | Q | A |
|---|---|---|---|---|---|---|---|---|
| I-4 | H | isopropyl | H | H | H | H | 3,5-dichlorophenyl | (4S)-3,4-dihydro-2H-chromen-4-yl |
| I-5 | H | isopropyl | H | H | H | H | 3-tert-butyl-5-fluorophenyl | (1S)-2,3-dihydro-1H-inden-1-yl |
| I-6 | H | dimethylamino | H | H | H | H | 3-tert-butyl-5-fluorophenyl | (1S)-1,2,3,4-tetrahydronaphthalen-1-yl |
| I-7 | H | methyl | H | H | H | H | 2,3,5-trifluorophenyl | (1S)-2,3-dihydro-1H-inden-1-yl |
| I-8 | H | morpholin-4-yl | H | H | H | H | 3,5-dichlorophenyl | (1S)-1,2,3,4-tetrahydronaphthalen-1-yl |

TABLE 1-continued

Examples

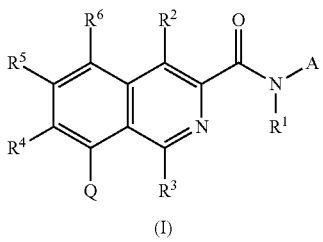

(I)

| Number | R1 | R2 | R3 | R4 | R5 | R6 | Q | A |
|---|---|---|---|---|---|---|---|---|
| I-9 | H | morpholin-4-yl | H | H | H | H | 2,3,5-trifluorophenyl | (1S)-1,2,3,4-tetrahydronaphthalen-1-yl |
| I-10 | H | morpholin-4-yl | H | H | H | H | 3-tert-butyl-5-fluorophenyl | (1S)-1,2,3,4-tetrahydronaphthalen-1-yl |
| I-11 | H | morpholin-4-yl | H | H | H | H | 3,5-dichlorophenyl | (4S)-3,4-dihydro-2H-chromen-4-yl |
| I-12 | H | morpholin-4-yl | H | H | H | H | 3-tert-butyl-5-chlorophenyl | (4S)-3,4-dihydro-2H-chromen-4-yl |
| I-13 | H | methyl | H | H | H | H | 3,5-dichlorophenyl | (4S)-3,4-dihydro-2H-chromen-4-yl |
| I-14 | H | methyl | H | H | H | H | 2-fluoro-4-methyl-5-(2,2,2-trifluoroethyl)sulfanyl | (4S)-3,4-dihydro-2H-chromen-4-yl |
| I-15 | H | morpholin-4-yl | H | H | H | H | 2,3,5-trifluorophenyl | 6-fluoro-3,4-dihydro-2H-thiochromen-4-yl |

TABLE 1a $^1$H-NMR Data

| Number | $^1$H-NMR [δ ppm]; solvent DMSO-$d_6$ |
|---|---|
| I-4 | 8.93-8.91 (m, 2H), 8.48-8.46 (m, 1H), 7.92-7.88 (m, 1H), 7.79-7.78 (m, 1H), 7.68-7.66 (m, 1H), 7.60 (s, 2H), 7.31-7.29 (m, 1H), 7.17-7.13 (m, 1H), 6.93-6.89 (m, 1H), 6.79-6.77 (m, 1H), 5.33-5.28 (m, 1H), 4.28-4.25 (m, 2H), 3.91 (sept, 1H), 2.20-2.15 (m, 1H), 2.07-2.04 (m, 1H), 1.56 (dd, 6H) |
| I-5 | 8.93 (s, 1H), 8.80-8.78 (m, 1H), 8.45-8.43 (m, 1H), 7.91-7.87 (m, 1H), 7.65-7.63 (m, 1H), 7.38-7.18 (m, 7H), 5.57-5.55 (m, 1H), 3.93 (sept, 1H), 3.02-2.96 (m, 1H), 2.90-2.81 (m, 1H), 1.95 (m, 1H), 1.57 (dd, 6H), 1.33 (s, 9H) |
| I-6 | 8.81 (s, 1H), 8.74-8.71 (m, 1H), 8.34-8.32 (m, 1H), 7.90-7.86 (m, 1H), 7.66-7.64 (m, 1H), 7.37-7.12 (m, 7H), 5.25 (m, 1H), 2.98 (s, 6H), 2.76 (m, 2H), 1.90 (m, 4H), 1.33 (s, 9H) |
| I-7 | 8.88-8.85 (m, 2H), 8.40-8.38 (m, 1H), 8.02-7.98 (m, 1H), 7.78-7.77 (m, 2H), 7.38-7.20 (m, 5H), 5.56 (m, 1H), 3.02-2.96 (m, 1H), 2.86 (m, 1H), 2.03-2.01 (m, 2H), 1.99 (s, 3H) |
| I-8 | 8.85 (s, 1H), 8.83-8.81 (m, 1H), 8.47-8.45 (m, 1H), 7.94-7.62 (m, 5H), 7.37 (m, 1H), 7.19-7.12 (m, 3H), 5.26 (m, 1H), 3.86 (m, 4H), 3.20 (m, 4H), 2.76 (m, 2H), 2.09-1.79 (m, 4H) |
| I-9 | 8.83-8.81 (m, 1H), 8.76-8.75 (m, 1H), 8.50-8.48 (m, 1H), 7.98-7.94 (m, 1H), 7.75-7.10 (m, 7H), 5.26 (m, 1H), 3.90-3.82 (m, 4H), 3.23 (m, 4H), 2.78-2.76 (m, 2H), 2.04-1.79 (m, 4H) |
| I-10 | 8.86 (s, 1H), 8.82-8.79 (m, 1H), 8.44-8.42 (m, 1H), 7.93-7.89 (m, 1H), 7.67-7.66 (m, 1H), 7.39-7.12 (m, 7H), 5.27 (m, 1H), 3.88-3.84 (m, 4H), 3.22 (m, 4H), 2.75 (m, 2H), 1.95 (m, 4H), 1.33 (s, 9H) |
| I-11 | 8.99-8.96 (m, 1H), 8.85 (s, 1H), 8.47-8.44 (m, 1H), 7.94-7.90 (m, 1H), 7.78-7.77 (m, 1H), 7.71-7.70 (m, 1H), 7.62 (m, 2H), 7.34-7.30 (m, 1H), 7.16-7.14 (m, 1H), 6.93-6.89 (m, 1H), 6.80-6.78 (m, 1H), 5.32 (m, 1H), 4.29-4.27 (m, 2H), 3.88-3.84 (m, 4H), 3.24-3.19 (m, 4H), 2.18-2.08 (m, 2H) |
| I-12 | 8.98-8.96 (m, 1H), 8.84 (s, 1H), 8.44-8.42 (m, 1H), 7.93-7.90 (m, 1H), 7.68-7.67 (m, 1H), 7.56 (m, 1H), 7.48-7.47 (m, 1H), 7.42-7.41 (m, 1H), 7.34-7.32 (m, 1H), 7.16 (m, 1H), 6.91 (m, 1H), 6.80-6.78 (m, 1H), 5.31 (m, 1H), 4.29-4.26 (m, 2H), 3.88-3.84 (m, 4H), 3.20 (m, 4H), 2.24-2.05 (m, 2H), 1.34 (s, 9H) |
| I-13 | 9.01-8.99 (m, 1H), 8.96 (s, 1H), 8.36-8.33 (m, 1H), 7.99-7.95 (m, 1H), 7.78-7.73 (m, 2H), 7.63-7.62 (m, 2H), 7.27-7.25 (m, 1H), 7.18-7.13 (m, 1H), 6.91-6.87 (m, 1H), 6.80-6.78 (m, 1H), 5.34-5.29 (m, 1H), 4.28-4.25 (m, 2H), 2.95 (s, 3H), 2.18-2.07 (m, 2H) |
| I-14 | 9.00-8.97 (m, 1H), 8.75-8.74 (m, 1H), 8.36-8.33 (m, 1H), 8.01-7.97 (m, 1H), 7.72-7.69 (m, 2H), 7.42-7.39 (m, 1H), 7.28-7.26 (m, 1H), 7.17-7.13 (m, 1H), 6.91-6.87 (m, 1H), 6.80-6.78 (m, 1H), 5.33-5.28 (m, 1H), 4.28-4.25 (m, 2H), 4.03-3.95 (q, 2H), 2.91 (s, 3H), 2.50 (s, 3H), 2.19-2.07 (m, 2H) |
| I-15 | 9.10-9.08 (m, 1H), 8.79-8.78 (m, 1H), 8.51-8.48 (m, 1H), 7.99-7.95 (m, 1H), 7.77-7.71 (m, 2H), 7.34 (br, 1H), 7.24-7.15 (m, 2H), 7.08-7.03 (m, 1H), 5.31-5.26 (m, 1H), 3.89-3.80 (m, 4H), 3.23-3.14 (m, 6H), 2.24-2.22 (m, 2H) |

TABLE 2

Intermediates

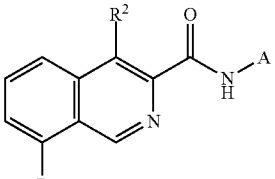

1C-1 to 1C-9

| Number | R2 | A |
|---|---|---|
| 1C-1 | morpholin-4-yl | (4S)-3,4-dihydro-2H-chromen-4-yl |
| 1C-2 | methyl | (4S)-3,4-dihydro-2H-chromen-4-yl |

TABLE 2-continued

Intermediates

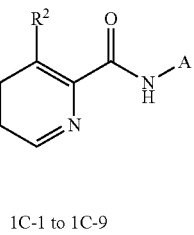

1C-1 to 1C-9

| Number | R2 | A |
|---|---|---|
| 1C-3 | isopropyl | (4S)-3,4-dihydro-2H-chromen-4-yl |
| 1C-4 | methyl | (1S)-2,3-dihydro-1H-inden-1-yl |
| 1C-5 | isopropyl | (1S)-2,3-dihydro-1H-inden-1-yl |
| 1C-6 | dimethylamino | (1S)-1,2,3,4-tetrahydronaphthalen-1-yl |
| 1C-7 | morpholin-4-yl | (1S)-1,2,3,4-tetrahydronaphthalen-1-yl |
| 1C-8 | dimethylamino | (4S)-3,4-dihydro-2H-chromen-4-yl |
| 1C-9 | morpholin-4-yl | 6-fluoro-3,4-dihydro-2H-thiochromen-4-yl |

TABLE 2a

1H-NMR Data intermediates

| Number | $^1$H-NMR [δ ppm]; solvent DMSO-$d_6$ |
|---|---|
| 1C-1 | 9.25 (s, 1H), 9.03-9.01 (m, 1H), 8.39-8.37 (m, 1H), 8.06-8.04 (m, 1H), 7.78-7.74 (m, 1H), 7.36-7.34 (m, 1H), 7.20-7.15 (m, 1H), 6.95-6.91 (m, 1H), 6.81-6.79 (m, 1H), 5.31 (m, 1H), 4.30-4.27 (m, 2H), 3.87-3.78 (m, 4H), 3.20-3.17 (m, 4H), 2.23-2.18 (m, 1H), 2.12-2.06 (m, 1H) |
| 1C-2 | 9.36 (s, 1H), 9.05-9.03 (m, 1H), 8.30-8.28 (m, 1H), 8.10-8.08 (m, 1H), 7.82-7.78 (m, 1H), 7.30-7.28 (m, 1H), 7.19-7.15 (m, 1H), 6.93-6.89 (m, 1H), 6.81-6.79 (m, 1H), 5.35-5.30 (m, 1H), 4.29-4.26 (m, 2H), 2.86(s, 3H), 2.21-2.10 (m, 2H) |
| 1C-3 | 9.37 (s, 1H), 8.98-8.96 (m, 1H), 8.44-8.42 (m, 1H), 8.06-8.04 (m, 1H), 7.76-7.72 (m, 1H), 7.33-7.31 (m, 1H), 7.19-7.15 (m, 1H), 6.95-6.91 (m, 1H), 6.80-6.78 (m, 1H), 5.32-5.30 (m, 1H), 4.28-4.25 (m, 2H), 3.82 (sept, 1H), 2.20-2.16 (m, 1H), 2.08-2.04 (m, 1H), 1.53 (dd, 6H) |
| 1C-4 | 9.36 (m, 1H), 8.94-8.92 (m, 1H), 8.30-8.28 (m, 1H), 8.10-8.08 (m, 1H), 7.82-7.78 (m, 1H), 7.34-7.21 (m, 4H), 5.61-5.55 (q, 1H), 3.03-2.97 (m, 1H), 2.89-2.85 (m, 1H), 2.88 (s, 3H), 2.50 (m, 1H), 2.07-2.00 (m, 1H) |
| 1C-5 | 9.37 (m, 1H), 8.85-8.83 (m, 1H), 8.45-8.42 (m, 1H), 8.06-8.04 (m, 1H), 7.76-7.72 (m, 1H), 7.35-7.33 (m, 1H), 7.29-7.22 (m, 3H), 5.60-5.54 (q, 1H), 3.88-3.84 (m, 1H), 2.99-2.84 (m, 2H), 2.48-2.46 (m, 1H), 1.98-1.93 (m, 1H), 1.53 (dd, 6H) |
| 1C-6 | 9.19 (m, 1H), 8.80-8.78 (m, 1H), 8.30-8.28 (m, 1H), 8.03-8.01 (m, 1H), 7.75-7.71 (m, 1H), 7.40-7.38 (m, 1H), 7.20-7.17 (m, 2H), 7.13-7.11 (m, 1H), 5.25 (m, 1H), 2.95 (s, 6H), 2.78-2.74 (m, 2H), 2.05-1.78 (m, 4H) |
| 1C-7 | 9.25 (m, 1H), 8.87-8.85 (m, 1H), 8.39-8.37 (m, 1H), 8.05-8.04 (m, 1H), 7.77-7.73 (m, 1H), 7.41-7.39 (m, 1H), 7.21-7.11 (m, 3H), 5.27 (m, 1H), 3.87-3.80 (m, 4H), 3.21-3.17 (m, 4H), 2.79-2.75 (m, 2H), 2.10-1.75 (m, 4H) |
| 1C-8 | 9.19 (m, 1H), 8.96-8.94 (m, 1H), 8.30-8.28 (m, 1H), 8.04-8.02 (m, 1H), 7.75-7.73 (m, 1H), 7.34-7.32 (m, 1H), 7.19-7.15 (m, 2H), 7.04 (s, 1H), 5.30 (m, 1H), 4.29-4.27 (m, 2H), 2.95 (s, 6H), 2.17-2.09 (m, 2H) |
| 1C-9 | 9.27(s, 1H), 9.13-9.11 (m, 1H), 8.39-8.37 (m, 1H), 8.07-8.05 (m, 1H), 7.79-7.75 (m, 1H), 7.26-7.16 (m, 2H), 7.10-7.05 (m, 1H), 5.32-5.27 (m, 1H), 3.88-3.77 (m, 4H), 3.18-3.15 (m, 6H), 2.26-2.22 (m, 2H) |

EXPERIMENTAL SECTION—BIOLOGICAL ASSAYS

Examples were tested in selected biological assays one or more times. When tested more than once, data are reported as either average values or as median values, wherein
the average value, also referred to as the arithmetic mean value, represents the sum of the values obtained divided by the number of times tested, and
the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

The in vitro activity of the compounds of the present invention can be demonstrated in the following assays:

In Vitro Assay 1: *C. elegans* Slo-1a—Action at a Recombinant *C. elegans* Cell Line Generation of a Stable *Caenorhabditis elegans* CHO Cell Line A CHO cell line was obtained from ATCC, code ATCC CRL-9096. For transfection with plasmid DNA to express *C. elegans* Slo-1a (accession number AAL28102)CHO cells were passaged to 40% confluence before adding the transfection solution to the cell culture. The transfection solution included 300 μL OptiMEM (Life Technologies, Nr.: 31985), 2 μL (=6 μg) of plasmid DNA containing the *C. elegans* Slo 1a gene and 9 μL FugeneHD (Promega, Nr.: E2311), and was added to the cells prior to incubation for 48 hours at 37° C., 5% $CO_2$. The transfection medium was exchanged for the selection medium which contains additional G418 (2 mg/ml, Invitrogen, Nr.: 10131) and the cells were seeded into 384 well plates (300 cells/well). After a few weeks, the remaining surviving cells were tested with a voltage sensitive dye (Membrane Potential Assay Kit, Molecular Devices Nr.: R8034) for K+ channel expression. Positive cell clones were purified by the limited dilution technique. For this the clone with the highest and most robust signal in the voltage sensitive dye assay was further subcloned (incubated) in 384 well plates (0.7 cells/well) in order to obtain clonal purity. This generated a final stable CHO cell line expressing the *C. elegans* Slo-1a.

Cell Culture Conditions

Cells were cultured at 37° C. and 5% $CO_2$ in MEMalpha with Glutamax I (Invitrogen, Nr.: 32571), supplemented with 10% (v/v) heat inactivated fetal bovine serum (Invitrogen, Nr.: 10500), G418 (1 mg/ml, Invitrogen, Nr.: 10131). Cells were detached using Accutase (Sigma, Nr.: A6964).

Membrane Potential Measurements

Laboratory compound testing was performed on 384-well microtiter plates (MTPs, Greiner, Nr.: 781092). 8000 cells/well were plated onto 384-well MTPs and cultured for 20 to 24 hours at 37° C. and 5% $CO_2$. After removal of the cell culture medium, the cells were washed once with tyrode (150 mM NaCl, 0.3 mM KCl, 2 mM $CaCl_2$, 1 mM $MgCl_2$, 0.8 mM $NaH_2PO_4$, 5 mM Glucose, 28 mM Hepes, pH 7.4) and then loaded with the voltage sensitive dye of the Membrane Potential Assay Kit diluted in tyrode for 1 h at room temperature.

After starting the measurement of fluorescence using a FLIPR Tetra (Molecular Devices, Exc. 510-545 nm, Emm.

565-625 n), test compounds were added followed by the addition of KCl tyrode (final assay concentration: 70 mM KCl, 2 mM $CaCl_2$, 1 mM $MgCl_2$, 0.8 mM $NaH_2PO_4$, 5 mM Glucose, 28 mM Hepes, pH 7.4, including the voltage sensitive dye). The measurement was completed after 7 minutes.

Statistics

The data were evaluated by using the ActivityBase XLfit software (IDBS) for curve fitting and calculation of the half-maximal effective concentration ($EC_{50}$) and are reported as negative decadic logarithm ($pE_{50}$).

For the following examples, $pE_{50}$>6.5-7.5 has been found: I-13.

For the following examples, $pE_{50}$>7.5-8.5 has been found: I-8.

In Vitro Assay 2: *D. immitis* Slo-1—Action at a Recombinant *D. immitis* Cell Line Generation of a Stable *D. immitis* Slo-1 CHO Cell Line A CHO cell line was obtained from ATCC, code ATCC CRL-9096. For transfection with plasmid DNA to express *Dirofilaria immitis* Slo-1 (based on Protein sequence JQ730003, codon optimized for hamster) CHO cells were passaged to 40% confluence before adding the transfection solution to the cell culture. The transfection solution included 300 μL OptiMEM (Life Technologies, Nr.: 31985), 2 μL (=6 μg) of plasmid DNA containing the *D. immitis* Slo 1 gene and 9 μL FugeneHD (Promega, Nr.: E2311), and was added to the cells prior to incubation for 48 hours at 37° C., 5% $CO_2$. The transfection medium was exchanged for the selection medium which contains additional G418 (2 mg/ml, Invitrogen, Nr.: 10131) and the cells were seeded into 384 well plates (300 cells/well). After a few weeks, the remaining surviving cells were tested with a voltage sensitive dye (Membrane Potential Assay Kit, Molecular Devices Nr.: R8034) for K+ channel expression. Positive cell clones were purified by the limited dilution technique. For this the clone with the highest and most robust signal in the voltage sensitive dye assay was further subcloned (incubated) in 384 well plates (0.7 cells/well) in order to obtain clonal purity. This generated a final stable CHO cell line expressing the *D. immitis* Slo-1.

Cell Culture Conditions

Cells were cultured at 37° C. and 5% $CO_2$ in MEMalpha with Glutamax I (Invitrogen, Nr.: 32571), supplemented with 10% (v/v) heat inactivated fetal bovine serum (Invitrogen, Nr.: 10500), G418 (1 mg/ml, Invitrogen, Nr.: 10131). Cells were detached using Accutase (Sigma, Nr.: A6964).

Membrane Potential Measurements

Laboratory compound testing was performed on 384-well microtiter plates (MTPs, Greiner, Nr.: 781092). 8000 cells/well were plated onto 384-well MTPs and cultured for 20 to 24 hours at 37° C. and 5% $CO_2$. After removal of the cell culture medium, the cells were washed once with tyrode (150 mM NaCl, 0.3 mM KCl, 2 mM $CaCl_2$, 1 mM $MgCl_2$, 0.8 mM $NaH_2PO_4$, 5 mM Glucose, 28 mM Hepes, pH 7.4) and then loaded with the voltage sensitive dye of the Membrane Potential Assay Kit diluted in tyrode for 1 h at room temperature.

After starting the measurement of fluorescence using a FLIPR Tetra (Molecular Devices, Exc. 510-545 nm, Emm. 565-625 nm), test compounds were added followed by the addition of KCl tyrode (final assay concentration: 70 mM KCl, 2 mM $CaCl_2$, 1 mM $MgCl_2$, 0.8 mM $NaH_2PO_4$, 5 mM Glucose, 28 mM Hepes, pH 7.4, including the voltage sensitive dye). The measurement was completed after 7 minutes.

Statistics

The data were evaluated by using the ActivityBase XLfit software (IDBS) for curve fitting and calculation of the half-maximal effective concentration ($EC_{50}$) and are reported as negative decadic logarithm ($pE_{50}$).

For the following examples, $pE_{50}$>5.3-6.5 has been found: I-2, I-7, I-8, I-11, I-12, I-15.

For the following examples, $pE_{50}$>6.5-7.5 has been found: I-3, I-4, I-9.

For the following examples, $pE_{50}$>7.5-8.5 has been found: I-1.

In Vitro Assay 3: *Nippostrongylus brasiliensis* (NIPOBR)

Adult *Nippostrongylus brasiliensis* were washed with saline buffer containing 100 U/ml penicillin, 0.1 mg/ml streptomycin and 2.5 μg/ml amphotericin B. Test compounds were dissolved in DMSO and worms were incubated in medium in a final concentration of 10 μg/ml (10 ppm). An aliquot of the medium was used to determine the acetylcholine esterase activity in comparison to a negative control. The principle of measuring acetylcholine esterase as readout for anthelmintic activity was described in Rapson et al (1986) and Rapson et al (1987).

For the following examples, activity (reduction of AChE compared to negative control) was higher than 80% at 10 μg/ml: I-1, I-2, I-3, I-4, I-7, I-8, I-9, I-11, I-12, I-13.

In Vitro Assay 4: *Dirofilaria immitis* Microfilariae (DIROIM L1)

≥250 *Dirofilaria immitis* microfilariae, which were freshly purified from blood, were added to wells of a microtitre plate containing a nutrient medium and the test compound in DMSO. Compounds were tested in concentration-response assay in duplicate. Larvae exposed to DMSO and no test compounds were used as negative controls. Larvae were evaluated after 72 h of incubation with the compound. Efficacy was determined as the reduction of motility in comparison to the negative control. Based on the evaluation of a wide concentration range, concentration-response curves as well as $EC_{50}$-values were calculated.

For the following examples, the $EC_{50}$ was <10 ppm: I-6, I-14, IC-1, IC-2, IC-3, IC-4, IC-5, IC-7, IC-9.

For the following examples, the $EC_{50}$ was <1 ppm: I-5, I-10, I-15.

For the following examples, the $EC_{50}$ was <0.1 ppm: I-1, I-2, I-3, I-4, I-7, I-8, I-9, I-11, I-12, I-13.

In Vitro Assay 5: *Dirofilaria immitis* (DIROIM L4)

10 *Dirofilaria immitis* third-stage larvae which were freshly isolated from their vector (intermediate host) were added to wells of a microtitre plate containing a nutrient medium and the test compound in DMSO. Compounds were tested in concentration-response assay in duplicate. Larvae exposed to DMSO and no test compounds were used as negative controls. Larvae were evaluated after 72 h of incubation with the compound. Within these 72 h of incubation the majority of larvae in negative control moult to fourth-stage larvae. Efficacy was determined as the reduction of motility in comparison to the negative control. Based on the evaluation of a wide concentration range, concentration-response curves as well as EC50-values were calculated.

For the following examples, the $EC_{50}$ was <1 ppm: I-5, I-7, I-10, I-13.

For the following examples, the $EC_{50}$ was <0.1 ppm: I-1, I-2, I-3, I-4, I-8, I-9, I-11, I-12, I-15.

Formulation Examples F-1 to F-15

Exemplary formulations consist of the active substance in 10% Transcutol, 10% Cremophor EL and 80% isotonic saline solution. First the active substance is dissolved in Transcutol. After solution in Transcutol, Cremophor and isotonic saline solution are added.

Examples for a formulation according to the present invention are the following formulation Examples F-1 to F-15. Therein, an active substance according to Examples I-1 to I-15 is dissolved in Transcutol to form a stock solution A-1 to A-15. Then 0.100 mL of this stock solution A-1 to A-15 are taken and 0.100 mL Cremophor EL and 0.800 mL isotonic saline solution are added. The resulting liquid formulations (formulation examples F-1 to F-15) have a volume of 1 mL.

Stock solution A-1 to A-15:

| 4.0 mg | compound of example I-1 to 1-15 |
| 0.100 Ml | Transcutol. |

Formulation Example I-1 to I-15

| 0.100 mL | stock solution A-1 to A-15, |
| 0.100 mL | Cremophor EL, and |
| 0.800 mL | isotonic saline solution. |

The invention claimed is:

1. A compound of formula (I):

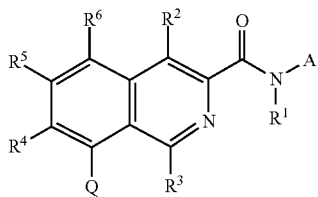

(I)

in which:

A is A1 or A2,

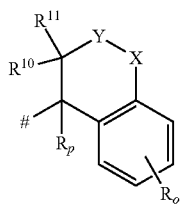

A1

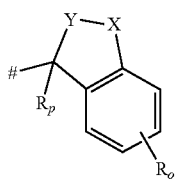

A2 o is 0, 1, 2, 3 or 4,

R is selected from the group consisting of hydrogen, halogen, cyano, nitro, OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —$NH(C_1$-$C_4$-alkyl), —$N(C_1$-$C_4$-alkyl)$_2$, —S—$C_1$-$C_4$-alkyl, —S(O)—$C_1$-$C_4$-alkyl, —$SO_2$-$C_1$-$C_4$-alkyl, —S—$C_1$-$C_4$-halogenoalkyl, —S(O)—$C_1$-$C_4$-halogenoalkyl and —$SO_2$—$C_1$-$C_4$-halogenoalkyl having 1 to 5 halogen atoms, $R_p$ is selected from the group consisting of hydrogen and $C_1$-$C_4$-alkyl, X, Y are independently selected from the group consisting of $C^7R^8$, O, S, and N-$R^9$, wherein at least one of X and Y is $CR^7R^8$, or X, Y form together a ring member selected from the group consisting of —C(O)—O—, —C(O)—$NR^9$—, —S(O)—$NR^9$—, —$SO_2$—$NR^9$— and —$SO_2$—O—, $R^1$ is selected from the group consisting of hydrogen, cyano, —CHO, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, $C_3$-$C_6$-halogenocycloalkyl having 1 to 5 halogen atoms, $C_3$-$C_4$-alkenyl, $C_3$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, —NH—$C_1$-$C_4$-alkyl, —N($C_1$-$C_4$-alkyl)$_2$, $NH_2$-$C_1$-$C_4$-alkyl-, $C_1$-$C_4$-alkyl-NH—$C_1$-$C_4$-alkyl-, ($C_1$-$C_4$-alkyl)$_2$N—$C_1$-$C_4$-alkyl-, $C_1$-$C_4$-alkyl-C(O)—, $C_1$-$C_4$-halogenoalkyl-C(O)— having 1 to 5 halogen atoms, $C_1$-$C_4$-alkoxy-C(O)—, benzyloxy-C(O)—, $C_1$-$C_4$-alkoxy-$C_1$-$C_4$-alkyl-C(O)—, —$SO_2$—$C_1$-$C_4$-alkyl, and —$SO_2$—$C_1$-$C_4$-halogenoalkyl having 1 to 5 halogen atoms;

phenyl-$C_1$-$C_4$-alkyl, optionally substituted by 1, 2, 3, 4 or 5 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —$NH(C_1$-$C_4$-alkyl), —$N(C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and heterocyclyl-$C_1$-$C_4$-alkyl, wherein the heterocyclyl substituent of the heterocyclyl-$C_1$-$C_4$-alkyl is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —$NH(C_1$-$C_4$-alkyl), —$N(C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^2$ is selected from the group consisting of hydrogen, halogen, cyano, —COOH, $C_1$-$C_4$-alkoxy-C(O)—, —C(O)—$NH_2$, —C(O)—$NH(C_1$-$C_4$-alkyl), —C(O)—$N(C_1$-$C_4$-alkyl)$_2$;

—$NR^{12}R^{13}$;

—$OR^{14}$;

—$SR^{15}$, —$S(O)R^{15}$, —$SO_2R^{15}$;

$C_1$-$C_6$-alkyl, $C_3$-$C_6$-cycloalkyl, $C_2$-$C_4$-alkenyl, $C_3$-$C_6$-cycloalkenyl, $C_2$-$C_4$-alkynyl, phenyl-$C_1$-$C_4$-alkyl, each of which is optionally substituted by 1, 2, 3, 4 or 5 substituents independently selected from the group consisting of halogen, —OH, —NO$_2$, cyano, C$_1$-C$_4$-alkyl-C(O)—, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, C$_1$-C$_4$-alkyl, C$_1$-C$_4$-halogenoalkyl having 1 to 5 halogen atoms, C$_1$-C$_4$-alkoxy, —NH$_2$, —NH(C$_1$-C$_4$-alkyl), —N(C$_1$-C$_4$-alkyl)$_2$, —NH(C(O)—C$_1$-C$_4$-alkyl), —N(C$_1$-C$_4$-alkyl)(C(O)—C$_1$-C$_4$-alkyl), —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms;

heterocyclyl-C$_1$-C$_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —NO$_2$, cyano, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms;

phenyl which is optionally substituted by 1, 2 or 3 substituents independently selected from the group consisting of halogen, cyano, nitro, —OH, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$-C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms; and a monocyclic or a bicyclic heterocycle selected from the group consisting of 4- to 10-membered heterocycloalkyl, heterospirocycloalkyl, 5-membered heteroaryl and 6-membered heteroaryl, each of which is optionally substituted by 1, 2, 3 or 4 substituents independently selected from the group consisting of halogen, cyano, nitro, —OH, oxo, thiono, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, C$_1$-C$_4$-alkyl, C$_1$-C$_4$-alkyl-C(O)—, C$_1$-C$_4$-halogenoalkyl having 1 to 5 halogen atoms, C$_1$-C$_4$-alkoxy, hydroxy-C$_1$-C$_4$-alkyl, C$_1$-C$_4$-alkoxy-C$_1$-C$_4$-alkyl-, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms, —SO$_2$—C$_1$-C$_4$-halogenoalkyl having 1 to 5 halogen atoms, and 4- to 10-membered heterocycloalkyl, R$^3$ is hydrogen or C$_1$-C$_4$-alkyl, R$^4$ is selected from the group consisting of hydrogen, halogen, —OH, cyano, C$_1$-C$_4$-alkyl, C$_3$-C$_6$-cycloalkyl, C$_1$-C$_4$-halogenoalkyl having 1 to 5 halogen atoms, C$_1$-C$_4$-alkoxy-C$_1$-C$_4$-alkyl, C$_1$-C$_4$-alkoxy, C$_1$-C$_4$-halogenoalkoxy having 1 to 5 halogen atoms, C$_1$-C$_4$-alkyl-C(O)—, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, and —SO$_2$—C$_1$-C$_4$-alkyl, R$^5$ is selected from the group consisting of hydrogen, halogen, —OH, cyano, C$_1$-C$_4$-alkyl, C$_3$-C$_6$-cycloalkyl, C$_1$-C$_4$-halogenoalkyl having 1 to 5 halogen atoms, C$_1$-C$_4$-alkoxy-C$_1$-C$_4$-alkyl, C$_1$-C$_4$-alkoxy, C$_1$-C$_4$-halogenoalkoxy having 1 to 5 halogen atoms, C$_1$-C$_4$-alkyl-C(O)—, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, and —SO$_2$—C$_1$-C$_4$-alkyl, R$^6$ is selected from the group consisting of hydrogen, halogen, —OH, cyano, C$_1$-C$_4$-alkyl, C$_3$-C$_6$-cycloalkyl, C$_1$-C$_4$-halogenoalkyl having 1 to 5 halogen atoms, C$_1$-C$_4$-alkoxy-C$_1$-C$_4$-alkyl, C$_1$-C$_4$-alkoxy, C$_1$-C$_4$-halogenoalkoxy having 1 to 5 halogen atoms, C$_1$-C$_4$-alkyl-C(O)—, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, and —SO$_2$—C$_1$-C$_4$-alkyl, R$^7$ is selected from the group consisting of hydrogen, —OH, fluorine, C$_1$-C$_4$-alkyl and C$_1$-C$_4$-alkoxy, R$^8$ is selected from the group consisting of hydrogen, —OH, fluorine, C$_1$-C$_4$-alkyl and C$_1$-C$_4$-alkoxy, or R$^7$ and R$^8$ together form an oxo group (=O), or R$^7$ and R$^8$ form, together with the carbon atom to which they are attached, a 3- to 6-membered ring selected from the group consisting of C$_3$-C$_6$-cycloalkyl and 3- to 6-membered heterocycloalkyl, R$^9$ is selected from the group consisting of hydrogen, C$_1$-C$_4$-alkyl, C$_1$-C$_4$-halogenoalkyl having 1 to 5 halogen atoms and C$_1$-C$_4$-alkoxy, R$^{10}$ is selected from the group consisting of hydrogen, —OH, C$_1$-C$_4$-alkyl and C$_1$-C$_4$-alkoxy, R$^{11}$ is selected from the group consisting of hydrogen, C$_1$-C$_4$-alkyl and C$_1$-C$_4$-alkoxy, or R$^{10}$ and R$^{11}$ form, together with the carbon atom to which they are attached, a 3- to 6-membered ring selected from the group consisting of C$_3$-C$_6$-cycloalkyl and 3- to 6-membered heterocycloalkyl, R$^{12}$ and R$^{13}$ are independently selected from the group consisting of
hydrogen, —OH, —NH$_2$, —NH(C$_1$-C$_4$-alkyl), —N(C$_1$-C$_4$-alkyl)$_2$, —NH(—C(O)—C$_1$-C$_4$-alkyl), —N(C$_1$-C$_4$-alkyl)(-C(O)—C$_1$-C$_4$-alkyl), C$_1$-C$_4$-alkoxy, C$_1$-C$_4$-alkoxy-C(O)—;

C$_3$-C$_6$-cycloalkyl, phenyl-C$_1$-C$_4$-alkyl, each of which is optionally substituted by 1, 2 or 3 substituents independently selected from the group consisting of halogen, —OH, cyano, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, —NH—C(O)—C$_1$-C$_4$-alkyl, —N(C$_1$-C$_4$-alkyl)(-C(O)—C$_1$-C$_4$-alkyl), C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms, —SO$_2$—C$_1$-C$_4$-halogenoalkyl having 1 to 5 halogen atoms and (C$_1$-C$_4$-alkoxy)$_2$P(=O)—;

heterocyclyl-C$_1$-C$_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, benzo-$C_5$-$C_6$-cycloalkyl, each of which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$-$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^{14}$ is selected from the group consisting of
—$NH_2$, —NH($C_1$-$C_4$-alkyl), —N($C_1$-$C_4$-alkyl)$_2$;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$-$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$-$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^{15}$ is selected from the group consisting of
hydrogen;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$-$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$-$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, Q is selected from the group consisting of 6- or 10-membered aryl and 5- to 10-membered heteroaryl, each of which is optionally substituted by 1, 2, 3, 4 or 5 substituents selected from the group consisting of halogen, $SF_5$, cyano, —CHO, nitro, oxo, $C_1$-$C_4$-alkyl, $C_1$-$C_4$-hydroxyalkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH—$SO_2$—($C_1$-$C_4$-alkyl), —N($SO_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocyclyl, which is optionally substituted with 1 or 2 substituents selected from the group consisting of fluorine, chlorine, bromine, methyl and cyano, —$CH_2$—O—($C_1$-$C_4$-alkyl), —$CH_2$—NH($C_1$-$C_4$-alkyl), —$CH_2$—N($C_1$-$C_4$-alkyl)$_2$, methyl substituted with a 4- to 6-membered heterocyclyl which itself is optionally substituted with 1 or 2 substituents selected from the group consisting of fluorine, chlorine, bromine, methyl and cyano, —$CH_2$—S—($C_1$-$C_4$-alkyl), —$CH_2$—S(O)—($C_1$-$C_4$-alkyl), —$CH_2$—$SO_2$—($C_1$-$C_4$-alkyl), —S—($C_1$-$C_4$-alkyl), —S(O)—($C_1$-$C_4$-alkyl), —$SO_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), —NHCO($C_1$-$C_4$-halogenoalkyl) having 1 to 5 halogen atoms, wherein when Y is O, S or N—$R^9$, none of $R^7$, $R^8$, $R^{10}$ and $R^{11}$ is —OH or $C_1$-$C_4$-alkoxy, and wherein when X is O, S or N—$R^9$, none of $R^7$ and $R^8$ is —OH or $C_1$-$C_4$-alkoxy;

or a stereoisomer, tautomer, N-oxide, hydrate, solvate, or salt thereof, or a mixture thereof.

2. The compound of claim 1, wherein:

A is A1 or A2,

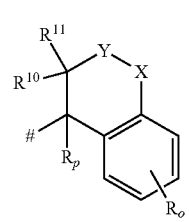

A1

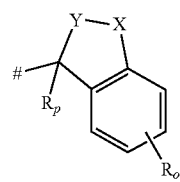

A2 o is 0, 1, 2, 3 or 4,

R is selected from the group consisting of hydrogen, halogen, cyano, nitro, OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$-$C_1$-$C_4$-alkyl, —S—$C_1$-$C_4$-halogenoalkyl, —S(O)—$C_1$-$C_4$-halogenoalkyl and —$SO_2$—$C_1$-$C_4$-halogenoalkyl having 1 to 5 halogen atoms, $R_p$ is selected from the group consisting of hydrogen and $C_1$-$C_4$-alkyl, X, Y are independently selected from the group consisting of $C^7R^8$, O, S, and N-$R^9$, wherein at least one of X and Y is $CR^7R^8$, or X, Y form together a ring member selected from the group consisting of —C(O)—O—, —C(O)—$NR^9$—, —S(O)—$NR^9$—, —$SO_2$—$NR^9$— and —$SO_2$—O—, $R^1$ is selected from the group consisting of hydrogen, cyano, —CHO, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, $C_3$-$C_6$-halogenocycloalkyl having 1 to 5 halogen atoms, $C_3$-$C_4$-alkenyl, $C_3$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, —NH—$C_1$-$C_4$-alkyl, —N($C_1$-$C_4$-alkyl)$_2$, $NH_2$-$C_1$-$C_4$-alkyl-, $C_1$-$C_4$-alkyl-NH—$C_1$-$C_4$-alkyl-, ($C_1$-$C_4$-alkyl)$_2$N—$C_1$-$C_4$-alkyl-, $C_1$-$C_4$-alkyl-C(O)—, $C_1$-$C_4$-halogenoalkyl-C(O)— having 1 to 5 halogen atoms, $C_1$-$C_4$-alkoxy-C(O)—, benzyloxy-C(O)—, $C_1$-$C_4$-alkoxy-$C_1$-$C_4$-alkyl-C(O)—, —$SO_2$—$C_1$-$C_4$-alkyl, and —$SO_2$—$C_1$-$C_4$-halogenoalkyl having 1 to 5 halogen atoms;

phenyl-$C_1$-$C_4$-alkyl, optionally substituted by 1, 2, 3, 4 or 5 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent of the heterocyclyl-$C_1$-$C_4$-alkyl is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^2$ is selected from the group consisting of hydrogen, halogen, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$;

—$NR^{12}R^{13}$;

—$OR^{14}$;

—$SR^{15}$, —S(O)$R^{15}$, —$SO_2R^{15}$;

$C_1$-$C_6$-alkyl, $C_3$-$C_6$-cycloalkyl, $C_2$-$C_6$-alkenyl, $C_3$-$C_6$-cycloalkenyl, $C_2$-$C_4$-alkynyl, phenyl-$C_1$-$C_4$-alkyl, each of which is optionally substituted by 1, 2, 3, 4 or 5 substituents independently selected from the group consisting of halogen, —OH, —$NO_2$, cyano, $C_1$-$C_4$-alkyl-C(O)—, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, —$NH_2$, —NH($C_1$-$C_4$-alkyl), —N($C_1$-$C_4$-alkyl)$_2$, —NH(C(O)—$C_1$-$C_4$-alkyl), —N($C_1$-$C_4$-alkyl)(C(O)—$C_1$-$C_4$-alkyl), —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent of the heterocyclyl-$C_1$-$C_4$-alkyl is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$-$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_1$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, heterospirocycloalkyl, 5-membered heteroaryl and 6-membered heteroaryl, each of which is optionally substituted by 1, 2, 3 or 4 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl), $C_1$-$C_4$-alkyl, $C_1$-$C_4$-alkyl-C(O)—, $C_1$-$C_4$-halogenoalkyl having 1 to 5 halogen atoms, $C_1$-$C_4$-alkoxy, hydroxy-$C_1$-$C_4$-alkyl, $C_1$-$C_4$-alkoxy-$C_1$-$C_4$-alkyl-, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms and 4- to 10-membered heterocycloalkyl, $R^3$ is hydrogen, or $C_1$-$C_4$-alkyl, $R^4$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), and —N($C_1$-$C_4$-alkyl)$_2$, $R^5$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), and —N($C_1$-$C_4$-alkyl)$_2$, $R^6$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), and —N($C_1$-$C_4$-alkyl)$_2$, $R^7$ is selected from the group consisting of hydrogen, —OH, fluorine, $C_1$-$C_4$-alkyl and $C_1$-$C_4$-alkoxy, $R^8$ is selected from the group consisting of hydrogen, —OH, fluorine, $C_1$-$C_4$-alkyl and $C_1$-$C_4$-alkoxy, or $R^7$ and $R^8$ together form an oxo group (=O), $R^9$ is selected from the group consisting of hydrogen, $C_1$-$C_4$-alkyl, $C_1$-$C_4$-halogenoalkyl having 1 to 5 halogen atoms and $C_1$-$C_4$-alkoxy, $R^{10}$ is selected from the group consisting of hydrogen, —OH, $C_1$-$C_4$-alkyl and $C_1$-$C_4$-alkoxy, $R^{11}$ is selected from the group consisting of hydrogen, $C_1$-$C_4$-alkyl and $C_1$-$C_4$-alkoxy, $R^{12}$ and $R^{13}$ are independently selected from the group consisting of hydrogen, —OH, —NH$_2$, —NH(C$_1$-C$_4$-alkyl), —N(C$_1$-C$_4$-alkyl)$_2$, —NH(—C(O)—C$_1$-C$_4$-alkyl), C$_1$-C$_4$-alkoxy;

C$_3$-C$_6$-cycloalkyl, phenyl-C$_1$-C$_4$-alkyl, each of which is optionally substituted by 1, 2 or 3 substituents independently selected from the group consisting of halogen, —OH, cyano, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, —NH—C(O)—C$_1$-C$_4$-alkyl, —N(C$_1$-C$_4$-alkyl)-(—C(O)—C$_1$-C$_4$-alkyl), C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms, —SO$_2$—C$_1$-C$_4$-halogenoalkyl having 1 to 5 halogen atoms and (C$_1$-C$_4$-alkoxy)$_2$P(=O)-;

heterocyclyl-C$_1$-C$_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl), C$_1$-C$_4$-alkyl, C$_1$-C$_4$-halogenoalkyl having 1 to 5 halogen atoms, C$_1$-C$_4$-alkoxy, hydroxy-C$_1$-C$_4$-alkyl, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_4$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms;

phenyl, benzo-C$_5$-C$_8$-cycloalkyl, each of which is optionally substituted by 1, 2 or 3 substituents independently selected from the group consisting of halogen, cyano, nitro, —OH, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms; and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, C$_1$-C$_4$-alkyl, C$_1$-C$_4$-halogenoalkyl having 1 to 5 halogen atoms, C$_1$-C$_4$-alkoxy, hydroxy-C$_1$-C$_4$-alkyl, C$_1$-C$_4$-halogenoalkoxy having 1 to 5 halogen atoms, Ca-Co-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms, R$^{14}$ is selected from the group consisting of
—NH$_2$, —NH(C$_1$-C$_4$-alkyl), —N(C$_1$-C$_4$-alkyl)$_2$;

C$_1$-C$_4$-alkyl, C$_3$-C$_6$-cycloalkyl, phenyl-C$_1$-C$_4$-alkyl, each of which is optionally substituted by 1, 2 or 3 substituents independently selected from the group consisting of halogen, —OH, cyano, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, C$_3$-C$_6$-cycloalkyl, —NH$_2$, —NH(C$_1$-C$_4$-alkyl), -N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms;

heterocyclyl-C$_1$-C$_4$-alkyl, wherein the heterocyclyl substitutent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, C$_1$-C$_4$-alkyl, C$_1$-C$_4$-halogenoalkyl having 1 to 5 halogen atoms, C$_1$-C$_4$-alkoxy, hydroxy-C$_1$-C$_4$-alkyl, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms;

phenyl, which is optionally substituted by 1, 2 or 3 substituents independently selected from the group consisting of halogen, cyano, nitro, —OH, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, C$_1$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms; and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, C$_1$-C$_4$-alkyl, C$_1$-C$_4$-halogenoalkyl having 1 to 5 halogen atoms, C$_1$-C$_4$-alkoxy, hydroxy-C$_1$-C$_4$-alkyl, C$_1$-C$_4$-halogenoalkoxy having 1 to 5 halogen atoms, C$_1$-C$_4$-cycloalkyl, —NH$_2$, —NH(C$_1$-C$_4$-alkyl), —N(C)—C$_4$-alkyl)$_2$, —S-C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^{15}$ is selected from the group consisting of hydrogen;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, ~C(O)—$NH_2$, —C(O)—NH($C_1$-$C_4$-alkyl), —C(O)—N($C_1$-$C_4$-alkyl), $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)-, —C(O)-$NH_2$, C(O)-NH($C_1$-$C_4$-alkyl), —C(O)-N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_1$-$C_4$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, Q is a substituted phenyl ring of formula (Q1)

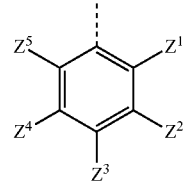

(Q1)

in which:

$Z^1$, $Z^2$, $Z^3$, $Z^4$, and $Z^5$ are independently selected from the group consisting of hydrogen, halogen, $SF_5$, cyano, —CHO, nitro, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH—$SO_2$—($C_1$-$C_4$-alkyl), —N($SO_2$-[$C_1$-$C_4$-alkyl])($C_1$-$C_4$-alkyl), ($C_1$-$C_4$-alkoxyimino)-$C_1$-$C_4$-alkyl, 4- to 6-membered heterocyclyl, which is optionally substituted with 1 or 2 substituents selected from the group consisting of fluorine, chlorine, bromine, methyl and cyano, —$CH_2$—O—($C_1$-$C_4$-alkyl), —$CH_2$—NH($C_1$-$C_4$-alkyl), —$CH_2$-N($C_1$-$C_4$-alkyl)$_2$, methyl substituted with a 4- to 6-membered heterocyclyl which itself is optionally substituted with 1 or 2 substituents selected from the group consisting of fluorine, chlorine, bromine, methyl and cyano, —$CH_2$—S—($C_1$-$C_4$-alkyl), —$CH_2$—S(O)—($C_1$-$C_4$-alkyl), —$CH_2$—$SO_2$—($C_1$-$C_4$-alkyl), —S—($C_1$-$C_4$-alkyl), —S(O)—($C_1$-$C_4$-alkyl), —$SO_2$—($C_1$-$C_4$-alkyl), —$S_2$—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), and NHCO($C_1$-$C_4$-halogenoalkyl) having 1 to 5 halogen atoms, or $Z^2$ and $Z^4$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two substituents selected from the group consisting of methyl, fluorine and oxo, and $Z^3$, $Z^4$, and $Z^5$ are independently selected from the group consisting of hydrogen, halogen, $SF_5$, cyano, CHO, nitro, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-alkoxy-C(O)—, $C_1$-$C_4$-halogenoalkoxy having 1 to 5 halogen atoms, —NH($C_1$-$C_4$-alkyl), —N($C_1$-$C_4$-alkyl)$_2$, —NH—$SO_2$—($C_1$-$C_4$-alkyl), —N($SO_2$—[$C_1$-$C_4$ alkyl]) ($C_1$-$C_4$-alkyl), ($C_1$-$C_4$-alkoxyimino)-$C_1$-$C_4$-alkyl, 4- to 6-membered heterocycloalkyl which is optionally substituted with 1 or 2 substituents selected from the group consisting of fluorine, methyl and cyano, —$CH_2$—O-($C_1$-$C_4$-alkyl), —$CH_2$—NH($C_1$-$C_4$-alkyl), —$CH_2$—N($C_1$-

$C_4$-alkyl)$_2$, methyl substituted with a 4- to 6-membered heterocycloalkyl which itself is optionally substituted with 1 or 2 substituents selected from the group consisting of fluorine, methyl and cyano, —CH$_2$—S—($C_1$-$C_4$-alkyl), —CH$_2$—S(O)—($C_1$-$C_4$-alkyl), —CH$_2$—SO$_2$—($C_1$-$C_4$-alkyl), —S—($C_1$-$C_4$-alkyl), —S(O)—($C_1$-$C_4$-alkyl), —SO$_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —SO$_2$—($C_1$-$C_4$-halogenoalkyl) having 1 to 5 halogen atoms, —CONH($C_1$-$C_4$-alkyl), —CONH($C_1$-$C_4$-cycloalkyl), —NHCO($C_1$-$C_4$-alkyl), —NHCO($C_3$-$C_6$-cycloalkyl), and —NHCO($C_1$-$C_4$-halogenoalkyl) having 1 to 5 halogen atoms, or $Z^2$ and $Z^3$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two substituents selected from the group consisting of methyl, fluorine and oxo, and $Z^1$, $Z^4$, and $Z^5$ are independently selected from the group consisting of hydrogen, halogen, SF$_5$, cyano, CHO, nitro, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH—SO$_2$—($C_1$-$C_4$-alkyl), —N(SO$_2$-[$C_1$-$C_4$-alkyl]) ($C_1$-$C_4$-alkyl), ($C_1$-$C_4$-alkoxyimino)-$C_1$-$C_4$-alkyl, 4- to 6-membered heterocycloalkyl which is optionally substituted with 1 or 2 substituents selected from the group consisting of fluorine, methyl and cyano, —CH$_2$-O-($C_1$-$C_4$-alkyl), —CH$_2$—NH($C_1$-$C_4$-alkyl), —CH$_2$-N($C_1$-$C_4$-alkyl)$_2$, methyl substituted with a 4- to 6-membered heterocycloalkyl which itself is optionally substituted with 1 or 2 substituents selected from the group consisting of fluorine, methyl and cyano, —CH$_2$—S—($C_1$-$C_4$-alkyl), —CH$_2$—S(O)—($C_1$-$C_4$-alkyl), —CH$_2$—SO$_2$—($C_1$-$C_4$-alkyl), —S-($C_1$-$C_4$-alkyl), —S(O)—($C_1$-$C_4$-alkyl), —SO$_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —SO$_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), halogenoalkyl) having 1 to 5 halogen atoms, or Q is a pyridine ring of formula (Q2)

(Q2)

in which:

$Z^6$, $Z^7$, $Z^8$ and $Z^9$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, and —NH($C_1$-$C_4$-alkyl), —N($C_1$-$C_4$-alkyl)$_2$, or Q is a pyrimidine ring of formula (Q3)

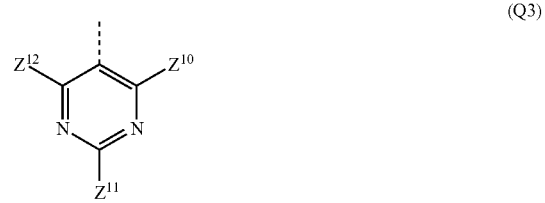

(Q3)

in which:

$Z^{10}$, $Z^{11}$ and $Z^{12}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), and —N($C_1$-$C_4$-alkyl)$_2$, or Q is a pyridine ring of formula (Q4)

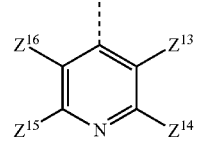

(Q4)

in which:

$Z^{13}$, $Z^{14}$, $Z^{15}$ and $Z^{16}$ are independently selected from the group consisting of hydrogen halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_1$-$C_4$-hydroxyalkyl, NH$_2$, —NH($C_1$-$C_4$-alkyl), —N($C_1$-$C_4$-alkyl)$_2$, —NH—CO-$C_1$-$C_4$-alkyl, and monocyclic heterocycles selected from the group consisting of 4- to 7-membered heterocycloalkyl or 5-membered heteroaryls having at least one nitrogen atom via which the heteroaryl ring is connected to the pyridine ring, each of which is optionally substituted with 1, 2 or 3 substituents independently selected from the group consisting of halogen, cyano, nitro, —OH, oxo, thiono, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_5$-$C_6$-cycloalkyl, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, —S—($C_1$-$C_4$-halogenoalkyl) having 1 to 5 halogen atoms, —S(O)—($C_1$-$C_4$-halogenoalkyl) having 1 to 5 halogen atoms, and —SO$_2$—($C_1$-$C_4$-halogenoalkyl) having 1 to 5 halogen atoms, or Q is a pyridine ring of formula (Q5)

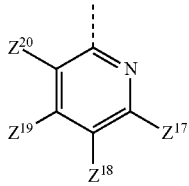

(Q5)

in which:
$Z^{17}$, $Z^{18}$, $Z^{19}$ and $Z^{20}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), and —N($C_1$-$C_4$-alkyl)$_2$, or Q is a 5-membered aromatic heterocycle of formula (Q6)

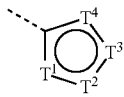

(Q6)

in which:
$T^1$-$T^4$ are independently selected from the group consisting of N, O, S, C-$Z^{21}$ and N-$Z^{22}$, wherein not more than one of $T^1$-$T^4$ is O, not more than one of $T^1$-$T^4$ is S, not more than one of $T^1$-$T^4$ is N-$Z^{22}$, and wherein
each $Z^{21}$ is independently selected from the group consisting of hydrogen, halogen, cyano, $C_1$-$C_4$-alkyl, $C_1$-$C_4$-halogenoalkyl having 1 to 5 halogen atoms, and $C_1$-$C_4$-alkoxy, $C_1$-$C_4$-halogenoalkoxy having 1 to 5 halogen atoms, and
each $Z^{22}$ is independently selected from the group consisting of hydrogen, $C_1$-$C_4$-alkyl, $C_1$-$C_4$-halogenoalkyl having 1 to 5 halogen atoms, $C_1$-$C_4$-alkyl-$C_5$-$C_6$-cycloalkyl, and $C_1$-$C_4$-alkoxy-$C_1$-$C_4$-alkyl, or Q is a 5-membered aromatic heterocycle of formula (Q7)

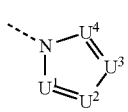

(Q7)

in which:
$U^1$-$U^4$ are independently selected from the group consisting of N and C-$Z^{23}$, wherein not more than three of $U^1$-$U^4$ are N, and wherein
each $Z^{23}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms,
wherein when Y is O, S or N-$R^9$, none of $R^7$, $R^8$, $R^{10}$ and $R^{11}$ is —OH, and wherein when X is O, S or N—$R^9$, none of $R^7$ and $R^8$ is —OH,
or a stereoisomer, tautomer, N-oxide, hydrate, solvate, or salt thereof, or a mixture thereof.

3. The compound of claim 1, wherein:
A is A1 or A2,

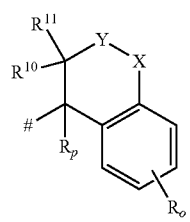

A1

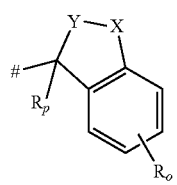

A2 o is 0, 1 or 2,
R is selected from the group consisting of halogen, $C_1$-$C_4$-alkyl and $C_1$-$C_4$-alkoxy, cyano, and $C_1$-$C_4$-halogenoalkyl having 1 to 5 halogen atoms,
$R_p$ is selected from the group consisting of hydrogen and $C_1$-$C_4$-alkyl,
X, Y are independently selected from the group consisting of CR RN, O, S, and N-R°, wherein at least one of X and Y is $CR^7R^8$,
$R^1$ is selected from the group consisting of hydrogen, $C_1$-$C_4$-alkyl, $C_3$-$C_6$-cycloalkyl, $C_3$-$C_4$-alkenyl, $C_3$-$C_4$-alkynyl, $C_1$-$C_4$-alkoxy-$C_1$-$C_4$-alkyl, $C_3$-$C_6$-cycloalkyl-$C_1$-$C_3$-alkyl, and cyano-$C_1$-$C_4$-alkyl,
$R^2$ is selected from the group consisting of
hydrogen, halogen, cyano, —COOH, $C_1$-$C_4$-alkoxy-C(O)—, —C(O)—NH$_2$, —C(O)—NH($C_1$-$C_4$-alkyl), C(O)—N($C_1$-$C_4$-alkyl)$_2$,
—NR$^{12}$R$^{13}$,
—OR$^{14}$;
—SR$^{15}$, —S(O)R$^{15}$, —SO$_2$R$^{15}$;
$C_1$-$C_4$-alkyl, $C_3$-$C_6$-cycloalkyl, $C_2$-$C_4$-alkenyl, $C_5$-$C_6$-cycloalkenyl, $C_2$-$C_4$-alkynyl, phenyl-$C_1$-$C_4$-alkyl, each of which is optionally substituted by 1, 2, 3, 4 or 5 substituents independently selected from the group consisting of halogen, —OH, cyano, $C_1$-$C_4$-alkoxy —C(O)-, —C(O)—NH$_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy; —NH$_2$, —NH($C_1$-$C_4$-alkyl), —N($C_1$-$C_4$-alkyl)$_2$, —NH(C(O)—$C_1$-$C_4$-alkyl), —N($C_1$-$C_4$-alkyl) (C(O)—$C_1$-$C_4$-alkyl), —S—$C_1$-$C_4$-alkyl, —S(O)—$C_1$-$C_4$-alkyl, —SO$_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —SO$_2$-$C_4$-$C_4$-halogenoalkyl having 1 to 5 halogen atoms; and
a monocyclic or a bicyclic heterocycle selected from the group consisting of 4- to 10-membered heterocycloalkyl, heterospirocycloalkyl, 5-membered heteroaryl and 6-membered heteroaryl, each of which is optionally substituted by 1, 2, 3 or 4 substituents independently selected from the group consisting of halogen, cyano, —OH, oxo, —COOH, $C_1$-$C_4$-alkoxy-C(O)—, —C(O)—NH$_2$, —C(O)—NH($C_1$-$C_4$-alkyl), —C(O)—N($C_1$-$C_4$-alkyl)$_2$, $C_1$-$C_4$-alkyl, $C_1$-$C_4$-alkyl-C(O)—, $C_1$-$C_4$-halogenoalkyl having 1 to 5 halogen atoms, $C_1$-$C_4$-alkoxy, hydroxy-$C_1$-$C_4$-alkyl, $C_1$-$C_4$-alkoxy-$C_1$-$C_4$-alkyl-, $C_1$-$C_4$-halogenoalkoxy having 1 to 5 halogen atoms, $C_3$-$C_6$-cycloalkyl, —$NH_2$, —$NH(C_1$-$C_4$-alkyl), —$N(C_1$-$C_4$-alkyl)$_2$, and 4- to 10-membered heterocycloalkyl, $R^3$ is hydrogen or $C_1$-$C_4$-alkyl, $R^4$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH(C)-$C_4$-alkyl), and —N(C)-$C_4$-alkyl)$_2$, $R^5$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —$NH(C_1$-$C_4$-alkyl), and —$N(C_1$-$C_4$-alkyl)$_2$, $R^6$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —$NH(C_1$-$C_4$-alkyl), and —$N(C_1$-$C_4$-alkyl)$_2$, $R^7$ is selected from the group consisting of hydrogen and $C_1$-$C_4$-alkyl, $R^8$ is selected from the group consisting of hydrogen and $C_1$-$C_4$-alkyl, or $R^7$ and $R^8$ together form an oxo group (=O), $R^9$ is $C_1$-$C_4$-alkyl, $R^{10}$ is selected from the group consisting of hydrogen, —OH, $C_1$-$C_4$-alkyl and $C_1$-$C_4$-alkoxy, $R^{11}$ is hydrogen, $R^{12}$ and $R^{13}$ are independently selected from the group consisting of hydrogen, —NH(—C(O)—$C_1$-$C_4$-alkyl), $C_1$-$C_4$-alkoxy;

$C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, —NH—C(O)—$C_1$-$C_4$-alkyl, —N($C_1$-$C_4$-alkyl)-(—C(O)—$C_1$-$C_4$-alkyl), $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, Ca-Ce-cycloalkyl, —$NH_2$, —$NH(C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms and ($C_1$-$C_4$-alkoxy)$_2$P(=O)—;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms;

phenyl, benzo-$C_5$-$C_6$-cycloalkyl, each of which is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms; and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, $R^{14}$ is selected from the group consisting of $C_1$-$C_4$-alkyl, $C_3$-$C_6$-cycloalkyl, and phenyl-$C_1$-$C_4$-alkyl, each of which is optionally substituted by 1, 2 or 3 substituents independently selected from the group consisting of halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, and heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms;

$R^{15}$ is selected from the group consisting of hydrogen;

$C_1$-$C_4$-alkyl, phenyl-$C_1$-$C_4$-alkyl, each of which is optionally substituted by 1, 2 or 3 substituents independently selected from the group consisting of halogen, —OH, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms;

Q is a substituted phenyl ring of formula (Q1)

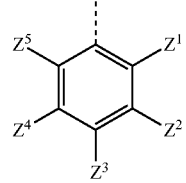

(Q1)

in which;

$Z^1$, $Z^2$, $Z^3$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, hydroxy, $C_1$-$C_4$-alkoxy, $C_1$-$C_4$-halogenoalkoxy having 1 to 5 halogen atoms, —NH($C_1$-$C_4$-alkyl), ~N($C_1$-$C_4$-alkyl) 2, 4- to 6-membered heterocyclyl, which is optionally substituted with 1 or 2 substituents selected from the group consisting of fluorine, chlorine, bromine, methyl and cyano, —S—($C_1$-$C_4$-alkyl), —S(O)—($C_1$-$C_4$-alkyl), —$SO_2$—($C_1$-$C_4$-alkyl), S-($C_1$-$C_4$-halogenoalkyl) having 1 to 5 halogen atoms, —S(O)—($C_1$-$C_4$-halogenoalkyl) having 1 to 5 halogen atoms, and —$SO_2$($C_1$-$C_4$-halogenoalkyl) having 1 to 5 halogen atoms, or $Z^1$ and $Z^2$ form, together with the carbon atoms that they are connected to, a 5- or 6-membered heterocycloalkyl, a 5-membered heteroaryl, or a 6-membered heteroaryl, each of which may be optionally substituted with one or two substituents selected from the group consisting of methyl, fluorine and oxo, and $Z^3$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-alkoxy-C(O)—, and $C_1$-$C_4$-halogenoalkoxy having 1 to 5 halogen atoms, or $Z^2$ and $Z^3$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two substituents selected from the group consisting of methyl, fluorine and oxo, and $Z^1$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, and/or a stereoisomer, tautomer, N-oxide, hydrate, solvate, and/or salt thereof, and/or a mixture thereof.

4. The compound according to of claim 1, wherein:
A is A1 or A2,

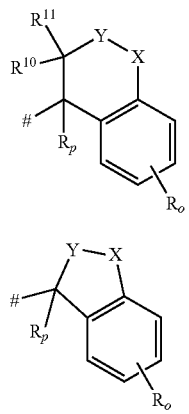

o is 0, 1 or 2,
R is selected from the group consisting of halogen, $C_1$-$C_4$-alkyl and $C_1$-$C_4$-alkoxy,
$R_p$ is selected from the group consisting of hydrogen and $C_1$-$C_4$-alkyl,
X is selected from the group consisting of $CR^7R^8$, O, S, and N—$R^9$,
Y is $CR^7R^8$ or O,
$R^1$ is hydrogen or $C_1$-$C_4$-alkyl,
$R^2$ is selected from the group consisting of
hydrogen, halogen, —C(O)—N($C_1$-$C_4$-alkyl);
—$NR^{12}R^{13}$;
—$OR^{14}$;
—$SR^{15}$, —S(O)$R^{15}$, —$SO_2R^{15}$;
$C_1$-$C_4$-alkyl, $C_3$-$C_6$-cycloalkyl, $C_2$-$C_4$-alkenyl, $C_3$-$C_6$-cycloalkenyl, each of which is optionally substituted by 1, 2, 3, 4 or 5 substituents independently selected from the group consisting of halogen, —OH, cyano, $C_1$-$C_4$-alkoxy-C(O)-and-C(O)—$NH_2$, $C_1$-$C_4$-alkoxy, —$NH_2$, —N(C)-$C_4$-alkyl)$_2$, —N($C_1$-$C_4$-alkyl) (C(O)—$C_1$-$C_4$-alkyl); and
a monocyclic or a bicycle heterocycle selected from the group consisting of 4- to 10-membered heterocycloalkyl, heterospirocycloalkyl, 5-membered heteroaryl, and 6-membered heteroaryl, each of which is optionally substituted by 1, 2, 3 or 4 substituents independently selected from the group consisting of halogen, —OH, oxo, —COOH, $C_1$-$C_4$-alkoxy-C(O)—, —C(O)—$NH_2$, $C_1$-$C_4$-alkyl, $C_1$-$C_4$-alkyl-C(O)—, $C_1$-$C_4$-halogenoalkyl having 1 to 5 halogen atoms, hydroxy-$C_4$-$C_4$-alkyl-, $C_1$-$C_4$-alkoxy-$C_1$-$C_4$-alkyl-, —$NH_2$, —N($C_1$-$C_4$-alkyl)$_2$, and 4- to 10-membered heterocycloalkyl, $R^3$ is hydrogen or $C_1$-$C_4$-alkyl,
$R^4$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, and —$NH_2$,
$R^5$ is selected from the group consisting of hydrogen, halogen, —OH, cyano, $C_1$-$C_4$-alkyl, $C_1$-$C_4$-halogenoalkyl having 1 to 5 halogen atoms, and $C_1$-$C_4$-alkoxy,
$R^6$ is selected from the group consisting of hydrogen, halogen, —OH, cyano, $C_1$-$C_4$-alkyl, $C_1$-$C_4$-halogenoalkyl having 1 to 5 halogen atoms, and $C_1$-$C_4$-alkoxy,
$R^7$ is selected from the group consisting of hydrogen and $C_1$-$C_4$-alkyl,
$R^8$ is selected from the group consisting of hydrogen and $C_1$-$C_4$-alkyl,
or $R^7$ and $R^8$ together form an oxo group (═O),
$R^9$ is $C_1$-$C_4$-alkyl,
$R^{10}$ is selected from the group consisting of hydrogen, —OH and $C_1$-$C_4$-alkyl, is hydrogen,
$R^{12}$ and $R^{13}$ are independently selected from the group consisting of
hydrogen, —NH(—C(O)—$C_1$-$C_4$-alkyl), $C_1$-$C_4$-alkoxy;
$C_3$-$C_6$-cycloalkyl, phenyl-$C_1$-$C_4$-alkyl, each of which is optionally substituted by 1, 2 or 3 substituents independently selected from the group consisting of halogen, —OH, —COOH, $C_1$-$C_4$-alkoxy-C(O)—, —C(O)—$NH_2$, —C(O)—N($C_1$-$C_4$-alkyl)$_2$, —NH—C(O)—$C_1$-$C_4$-alkyl, $C_1$-$C_4$-alkyl, $C_1$-$C_4$-alkoxy, $C_3$-$C_6$-cycloalkyl, —$NH_2$, —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, and ($C_1$-$C_4$-alkoxy)$_2$P(═O)-;
heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms and $C_1$-$C_4$-alkoxy;
phenyl and benzo-$C_3$-$C_6$-cycloalkyl, each of which is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms; and a monocyclic or a bicyclic heterocycle selected from the group consisting of 4- to 10-membered heterocycloalkyl, 5-membered heteroaryl and 6-membered heteroaryl each of which is optionally substituted by 1, 2 or 3 substituents independently selected from the group consisting of halogen, —OH, oxo, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, $R^{14}$ is selected from the group consisting of
$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, $C_1$-$C_4$-alkyl, $C_1$-$C_4$-alkoxy and $C_3$-$C_6$-cycloalkyl; and
4- to 10-membered heterocycloalkyl, $R^{15}$ is selected from the group consisting of
hydrogen;
$C_1$-$C_4$-alkyl, which is optionally substituted by 1, 2 or 3 substituents independently selected from the group consisting of —OH and —COOH; and
a 6-membered heteroaryl, Q is a substituted phenyl ring of formula (Q1)

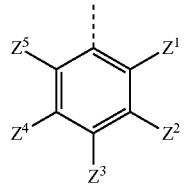

(Q1)

in which:
$Z^1$ and $Z^5$ are independently selected from the group consisting of hydrogen, halogen, $C_1$-$C_4$-alkyl, $C_1$-$C_4$-alkoxy, and $C_1$-$C_4$-halogenoalkyl having 1 to 5 halogen atoms $Z^2$ and $Z^4$ are independently selected from the group consisting of hydrogen, halogen, cyano, —OH, $C_1$-$C_4$-alkyl, $C_1$-$C_4$-alkoxy, —NH($C_1$-$C_4$-alkyl), —N($C_1$-$C_4$-alkyl)$_2$, $C_1$-$C_4$-halogenoalkyl having 1 to 5 halogen atoms, $C_1$-$C_4$-halogenoalkoxy having 1 to 5 halogen atoms, —S—($C_1$-$C_4$-alkyl)S-($C_1$-$C_4$-halogenoalkyl) having 1 to 5 halogen atoms, and a 4- to 6-membered heterocycloalkyl, and $Z^3$ is selected from the group consisting of hydrogen, halogen, $C_1$-$C_4$-alkyl, $C_1$-$C_4$-alkoxy, $C_1$-$C_4$-halogenoalkoxy having 1 to 5 halogen atoms, and —N($C_1$-$C_4$-alkyl)$_2$, or $Z^1$ and $Z^2$ form, together with the carbon atoms that they are connected to, a 5-membered heterocycloalkyl or a 5-membered heteroaryl, each of which may be optionally substituted with one or two substituents selected from the group consisting of methyl, fluorine and oxo, $Z^3$ and $Z^5$ are hydrogen, and $Z^4$ is selected from the group consisting of hydrogen and $C_1$-$C_4$-alkoxy-C(O)— or a stereoisomer, tautomer, N-oxide, hydrate, solvate, or salt thereof, or a mixture thereof.

5. The compound of claim 1, wherein:

A is selected from the group consisting of

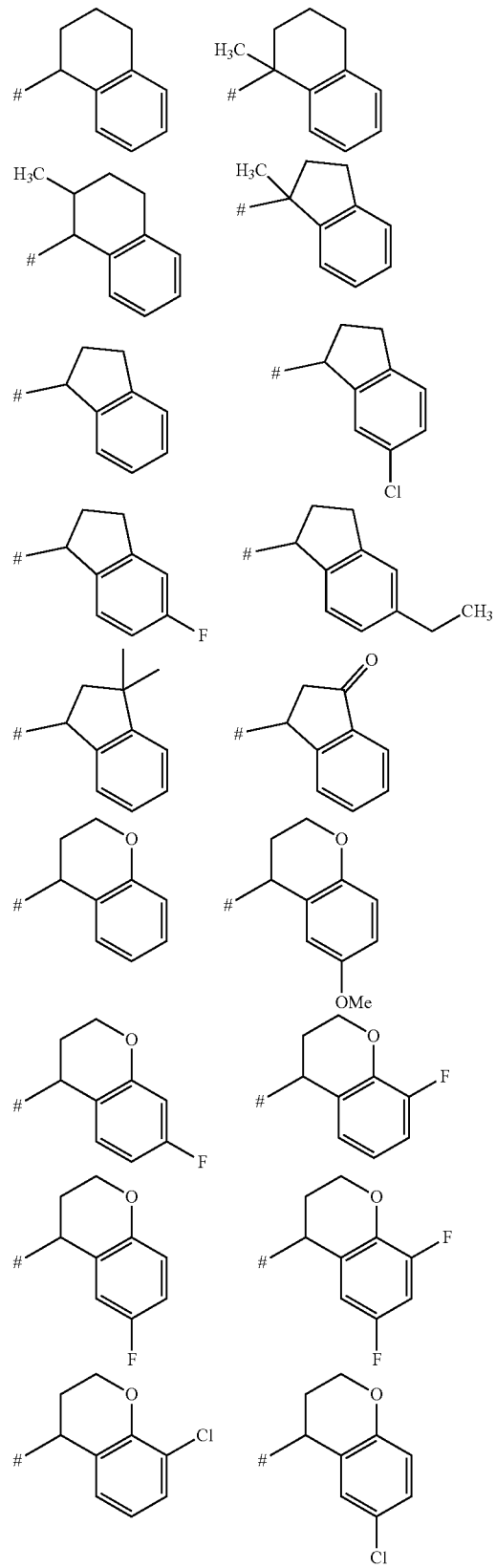

-continued

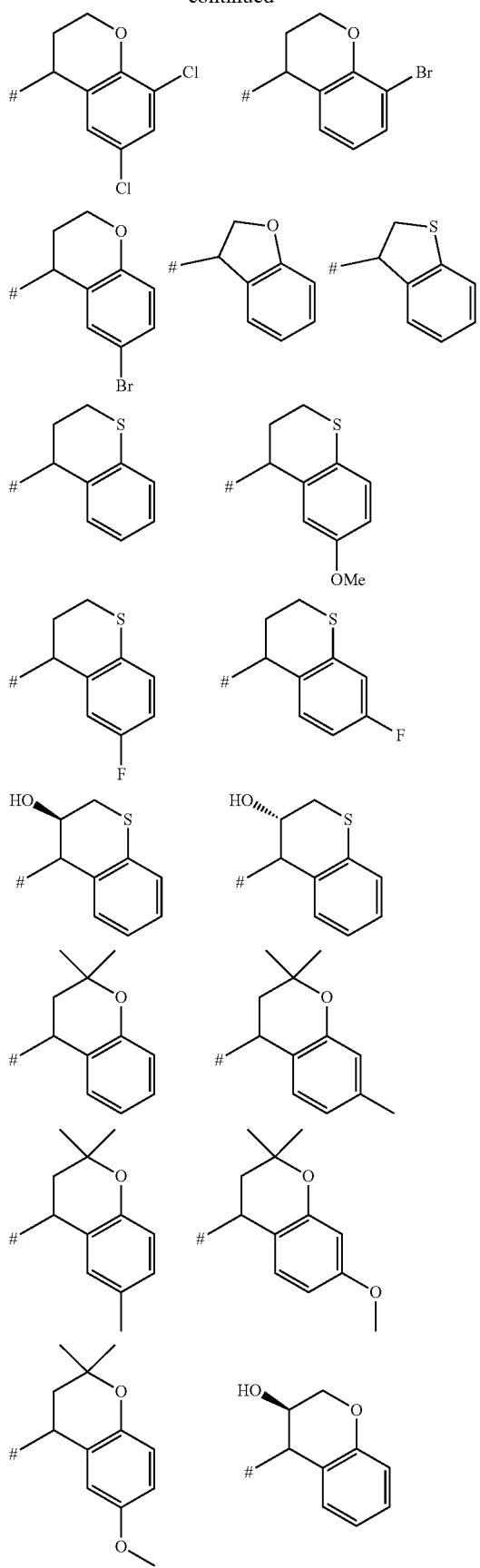

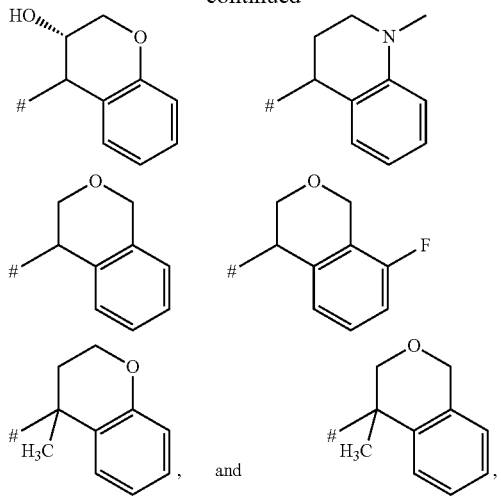

R[1] is hydrogen or methyl,
R[2] is selected from the group consisting of
    hydrogen, chlorine, iodine, —C(O)—N(CH$_3$)$_2$,
    —NR[12]R[13];
    —OR[14];
    —SR[15], —S(O)R[15], —SO$_2$R[15];
    methyl, ethyl, propyl, isopropyl, cyclopropyl, cyclobutyl, cyclopentyl, cyclohexyl, ethenyl, propenyl, cyclopentenyl, cyclohexenyl, each of which is optionally substituted by 1 or 2 substituents independently selected from the group consisting of —OH, cyano, ethoxy —C(O)—, —C(O)—NH$_2$, methoxy, NH$_2$, N(CH$_3$)$_2$, and N(CH$_3$)(C(O)CH$_3$); and
    a monocyclic or a bicyclic heterocycle selected from the group consisting of azetidine, oxetane, pyrrolidine, tetrahydrofurane, pyrazolidine, imidazolidine, 1,2,4-triazolidine, piperidine, piperazine, tetrahydropyrane, tetrahydropyridine, dihydro-2H-pyrane, 1,2-oxazolidine, 1,2-oxazine, morpholine, thiomorpholine, 3,4-dihydroisoquinoline, 2,3-dihydro-indole, 1,3-dihydro-isoindoel, 3,9-dioxa-7-azabicyclo[3.3.1]nonane, 6-oxa-3-azabicyclo[3.1.1]heptane, 8-oxa-3-azabicyclo[3.2.1]octane, thiophene, imidazole, pyrazole, 1,2,4-triazole, 1,2,3 triazole, 1,2,3,4-tetrazole, pyridine, dihydropyridine, pyrimidine, tetrahydropyrimidine, and 4-oxa-7-azaspiro[2.5]octane, each of which is optionally substituted by 1, 2, 3 or 4 substituents independently selected from the group consisting of fluorine, chlorine, cyano, —OH, oxo, —COOH, methoxy-C(O)—, ethoxy-C(O)—, tert-butoxy-C(O)—, —C(O)—NH$_2$, methyl, methyl-C(O)—, difluoromethyl, trifluoromethyl, hydroxymethyl-, methoxymethyl-, —NH$_2$, —NMe$_2$, and pyrrolidine,
R[3] is hydrogen or methyl,
R[4] is selected from the group consisting of hydrogen, fluorine, chlorine, —OH, cyano, methyl, methoxy, trifluoromethyl, trifluoromethoxy and NH$_2$,
R[5] is selected from the group consisting of hydrogen, fluorine, chlorine, —OH, cyano, methyl, methoxy and trifluoromethyl,
R[6] is selected from the group consisting of hydrogen, fluorine, chlorine, —OH, cyano, methyl and methoxy, $R^{12}$ and $R^{13}$ are independently selected from the group consisting of hydrogen, —NH(—C(O)-methyl), methoxy;

cyclopropyl, cyclobutyl, benzyl, 1-phenylethyl, each of which is optionally substituted by 1, 2 or 3 substituents independently selected from the group consisting of fluorine, —OH, —COOH, methoxy-C(O)—, ethoxy —C(O)—, tert-butoxy-C(O)—, —C(O)—NH$_2$, —C(O)—NMe$_2$, —NH—C(O)-methyl, methyl, methoxy, cyclopropyl, —NH$_2$, NMe$_2$, S-methyl, S(O)-methyl, SO$_2$-methyl, and (EtO)$_2$P(=O)—;

heterocyclyl-methyl, heterocyclyl-ethyl, wherein the heterocyclyl substituent is selected from the group consisting of oxetane, tetrahydrofurane, tetrahydropyrane pyrrolidine, morpholine, pyrazole, imidazole, 1,2,4-oxadiazole, and pyridine, each of which is optionally substituted by 1 substituent independently selected from the group consisting of fluorine, chlorine, —OH, oxo and methyl;

phenyl;

2,3-dihydro-1H-indene, and a monocyclic heterocycle selected from the group consisting of oxetane, thietane, pyrrolidine, morpholine, tetrahydropyrane, pyridine and pyrazole, each of which is optionally substituted by 1 or 2 substituents independently selected from the group consisting of fluorine, chlorine, —OH, oxo, and methyl;

$R^{14}$ is selected from the group consisting of methyl, ethyl, isopropyl, butyl, cyclopentyl, benzyl, each of which is optionally substituted by 1 or 2 substituents independently selected from the group consisting of fluorine, —OH, methyl, methoxy and cyclopentyl; and a monocyclic heterocycle selected from the group consisting of pyrrolidin and tetrahydropyran, $R^{15}$ is selected from the group consisting of methyl and ethyl, each of which is optionally substituted by 1 substituent independently selected from the group consisting of —OH and —COOH; and pyridine, Q is a substituted phenyl ring of formula (Q1)

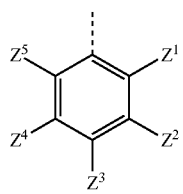

(Q1)

in which:

$Z^1$ and $Z^5$ are independently selected from the group consisting of hydrogen, fluorine, chlorine, methyl, trifluoromethyl and methoxy, $Z^2$ and $Z^4$ are independently selected from the group consisting of hydrogen, fluorine, chlorine, —OH, cyano, methyl, ethyl, tert-butyl, —NHMe, —NMe$_2$, trifluoromethyl, methoxy, trifluoromethoxy, —SMe, 2,2,2-trifluoroethyl) sulfanyl and morpholinyl, and $Z^3$ is independently selected from the group consisting of hydrogen, fluorine, chlorine, methyl, methoxy, difluoromethoxy and —NMe$_2$, or a stereoisomer, tautomer, N-oxide, hydrate, solvate, or salt thereof, or a mixture thereof.

6. The compound of claim 1, wherein:

A is selected from the group consisting of

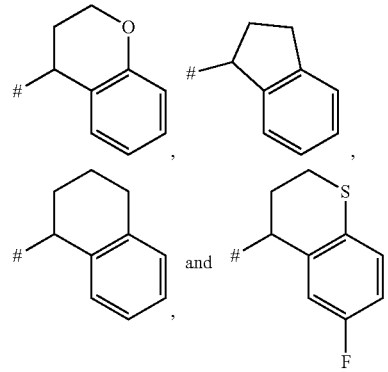

or a stereoisomer, tautomer, N-oxide, hydrate, solvate, or salt thereof, or a mixture thereof.

7. The compound of claim 1, wherein:

$R^2$ is selected from the group consisting of hydrogen, chlorine, iodine, —C(O)—N(CH$_3$)$_2$, —NR$^{12}$R$^{13}$;

—OR$^{14}$;

—SR$^{15}$, —S(O) R$^{15}$, —SO$_2$R$^{15}$;

methyl, ethyl, propyl, isopropyl, cyclopropyl, cyclobutyl, cyclopentyl, cyclohexyl, ethenyl, propenyl, cyclopentenyl, cyclohexenyl, each of which is optionally substituted by 1 or 2 substituents independently selected from the group consisting of —OH, cyano, ethoxy —C(O)—, —C(O)—NH$_2$, methoxy, NH$_2$, N(CH$_3$)$_2$, and N(CH$_3$)(C(O)CH$_3$); and a monocyclic or a bicyclic heterocycle selected from the group consisting of azetidine, oxetane pyrrolidine, tetrahydrofurane, pyrazolidine, imidazolidine, 1,2,4-triazolidine, piperidine, piperazine, tetrahydropyridine, dihydro-2H-pyrane, 1,2-oxazolidine, 1,2-oxazine, morpholine, thiomorpholine, 3,4-dihydroisoquinoline, 2,3-dihydro-indole, 1,3-dihydroisoindoel, 3,9-dioxa-7-azabicyclo[3.3.1]nonane, 6-oxa-3-azabicyclo[3.1.1]heptane, 8-oxa-3-azabicyclo[3.2.1]octane, thiophene, imidazole pyrazole, 1,2,4-triazole, 1,2,3-triazole, 1,2,3,4-tetrazole, pyridine, dihydropyridine pyrimidine, tetrahydropyrimidine, and 4-oxa-7-azaspiro[2.5]octane, each of which is optionally substituted by 1, 2, 3 or 4 substituents independently selected from the group consisting of fluorine, chlorine, cyano-OH, oxo, —COOH, methoxy-C(O)—, ethoxy-C(O)— tert-butoxy-C(O)—, —C(O)—NH$_2$, methyl, methyl-C(O))—, difluoromethyl, trifluoromethyl, hydroxymethyl-, methoxymethyl-, —NH$_2$, —NMe$_2$, and pyrrolidine, $R^{12}$ and $R^{13}$ are independently selected from the group consisting of hydrogen, —NH(—C(O)-methyl), methoxy;

cyclopropyl, cyclobutyl, benzyl, 1-phenylethyl, each of which is optionally substituted by 1, 2 or 3 substituents independently selected from the group consisting of fluorine, —OH, COOH, methoxy-C(O)—, ethoxy —C(O)—, tert-butoxy-C(O)—, —C(O)—NH$_2$, —C(O)—NMe$_2$, —NH—C(O)-methyl, methyl, methoxy, cyclopropyl, —NH$_2$, NMe$_2$, S-methyl, S(O)-methyl, SO$_2$-methyl, and (EtO)$_2$P(=O)-;

heterocyclyl-methyl, heterocyclyl-ethyl, wherein the heterocyclyl substituent is selected from the group consisting of oxetane, tetrahydrofurane, tetrahydropyrane pyrrolidine, morpholine, pyrazole, imidazole, 1,2,4-oxadiazole, and pyridine, each of which is optionally substituted by 1 substituent independently selected from the group consisting of fluorine, chlorine, —OH, oxo and methyl;

phenyl;

2,3-dihydro-1H-indene, and a monocyclic heterocycle selected from the group consisting of oxetane, thietane, pyrrolidine, morpholine, tetrahydropyrane, pyridine and pyrazole, each of which is optionally substituted by 1 or 2 substituents independently selected from the group consisting of fluorine, chlorine, —OH, oxo, and methyl;

R$^{14}$ is selected from the group consisting of methyl, ethyl, isopropyl, butyl, cyclopentyl, benzyl, each of which is optionally substituted by 1 or 2 substituents independently selected from the group consisting of fluorine, —OH, methyl, methoxy and cyclopentyl; and a monocyclic heterocycle selected from the group consisting of pyrrolidin and tetrahydropyran, R$^{15}$ is selected from the group consisting of methyl and ethyl, each of which is optionally substituted by 1 substituent independently selected from the group consisting of —OH and —COOH; and pyridine, or a stereoisomer, tautomer, N-oxide, hydrate, solvate, or salt thereof, or a mixture thereof.

8. The compound of claim 1, wherein:

Q is a substituted phenyl ring of formula (Q1)

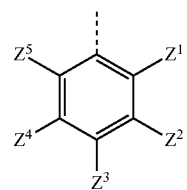

(Q1)

in which:

Z$^1$, Z$^2$, Z$^3$, Z$^4$, and Z$^5$ are independently selected from the group consisting of hydrogen, halogen, cyano, C$_1$-C$_4$-alkyl, C$_1$-C$_4$-halogenoalkyl having 1 to 5 halogen atoms, hydroxy, C$_1$-C$_4$-alkoxy, C$_1$-C$_4$-halogenoalkoxy having 1 to 5 halogen atoms, —NH(C$_1$-C$_4$-alkyl), —N(C$_1$-C$_4$-alkyl)$_2$, 4- to 6-membered heterocyclyl, which is optionally substituted with 1 or 2 substituents selected from the group consisting of fluorine, chlorine, bromine, methyl and cyano, —S—(C$_1$-C$_4$-alkyl), —S(O)—(C$_1$-C$_4$-alkyl), —SO$_2$—(C$_1$-C$_4$-alkyl), —S—(C$_1$-C$_4$-halogenoalkyl) having 1 to 5 halogen atoms, —S(O)—(C$_1$-C$_4$-halogenoalkyl) having 1 to 5 halogen atoms, and —SO$_2$—(C$_1$-C$_4$-halogenoalkyl) having 1 to 5 halogen atoms, or Z$^1$ and Z$^2$ form, together with the carbon atoms that they are connected to, a 5- or 6-membered heterocycloalkyl, a 5-membered heteroaryl, or a 6-membered heteroaryl, each of which may be optionally substituted with one or two substituents selected from the group consisting of methyl, fluorine and oxo, and Z$^3$, Z$^4$, and Z$^5$ are independently selected from the group consisting of hydrogen, halogen, cyano, C$_1$-C$_4$-alkyl, C$_1$-C$_4$-halogenoalkyl having 1 to 5 halogen atoms, C$_1$-C$_4$-alkoxy, C$_1$-C$_4$-alkoxy-C(O)—, and C$_1$-C$_4$-halogenoalkoxy having 1 to 5 halogen atoms, or Z$^2$ and Z$^3$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two substituents selected from the group consisting of methyl, fluorine and oxo, and Z$^1$, Z$^4$, and Z$^5$ are independently selected from the group consisting of hydrogen, halogen, cyano, C$_1$-C$_4$-alkyl, C$_1$-C$_4$-halogenoalkyl having 1 to 5 halogen atoms, C$_1$-C$_4$-alkoxy, and C$_1$-C$_4$-halogenoalkoxy having 1 to 5 halogen atoms, or a stereoisomers, tautomers, N-oxides, hydrates, solvates, or salts thereof, or mixtures of same.

9. The compound of claim 1, wherein:

Q is a substituted phenyl ring of formula (Q1)

(Q1)

in which:

Z$^1$ and Z$^5$ are independently selected from the group consisting of hydrogen, fluorine, chlorine, methyl, methoxy and trifluoromethyl, Z$^2$ and Z$^4$ are independently selected from the group consisting of hydrogen, fluorine, chlorine, —OH, cyano, methyl, ethyl, tert-butyl, —NHMe, —NMe$_2$, trifluoromethyl, methoxy, trifluoromethoxy, —SMe, 2,2,2-trifluoroethyl) sulfanyl and morpholinyl, and Z$^3$ is independently selected from the group consisting of hydrogen, fluorine, chlorine, methyl, methoxy, difluoromethoxy and —NMe$_2$, or a stereoisomer, tautomer, N-oxide, hydrate, solvate, or salt thereof, or a mixture thereof.

10. The compound of claim 1, wherein:

A is A3 or A4

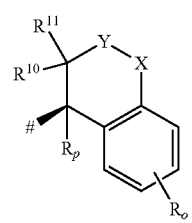

A3

-continued

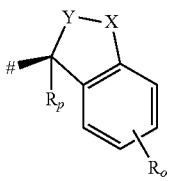

A4 wherein $R_p$ is selected from the group consisting of hydrogen and $C_1$-$C_4$-alkyl;

or a stereoisomer, tautomer, N-oxide, hydrate, solvate, or salt thereof, or a mixture thereof.

11. A method of preparing the compound of formula (I) of claim 1, said method comprising allowing an intermediate compound of formula 1C:

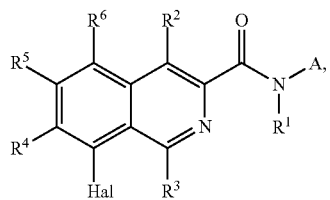

1C wherein Hal is halogen, to react with a compound of formula 1D:

Q-B(OR)$_2$     1D in which each R may be individually H or Me or both R are pinacolate, thereby giving a compound of formula (I):

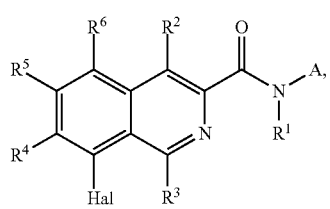

(I)

12. A compound of formula 1C:

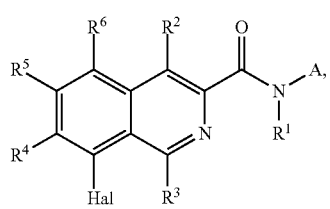

1C in which:

$R^2$ is as defined for the compound of formula (I) according to claim 1, wherein A, $R^1$, $R^3$, $R^4$, $R^5$, and $R^6$ are is A1 or A2,

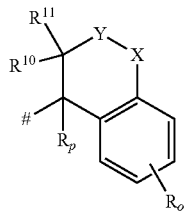

A1

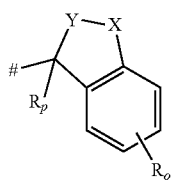

A2 o is 0, 1, 2, 3 or 4,

R is selected from the group consisting of hydrogen, halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_1$-$C_6$-cycloalkyl, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, —S—$C_1$-$C_4$-halogenoalkyl, —S(O)—$C_1$-$C_4$-halogenoalkyl and —SO$_2$—$C_1$-$C_4$-halogenoalkyl having 1 to 5 halogen atoms, $R_p$ is selected from the group consisting of hydrogen and $C_1$-$C_4$-alkyl, X, Y are independently selected from the group consisting of $CR^7R^8$, O, S, and N—$R^9$, wherein at least one of X and Y is $CR^7R^8$, or X, Y form together a ring member selected from the group consisting of —C(O)—O—, —C(O)—NR$^9$—, —S(O)—NR$^9$—, —SO$_2$—NR$^9$— and —SO$_2$—O—, $R^1$ is selected from the group consisting of hydrogen, cyano, ~CHO, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, $C_3$-$C_6$-halogenocycloalkyl having 1 to 5 halogen atoms, $C_5$-$C_4$-alkenyl, $C_1$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, —NH—$C_1$-$C_4$-alkyl, —N($C_1$-$C_4$-alkyl)$_2$, NH$_2$-$C_1$-$C_4$-alkyl-, $C_1$-$C_4$-alkyl-NH—$C_1$-$C_4$-alkyl-, ($C_1$-$C_4$-alkyl)$_2$N—$C_1$-$C_4$-alkyl-, $C_1$-$C_4$-alkyl-C(O)—, $C_1$-$C_4$-halogenoalkyl-C(O)-having 1 to 5 halogen atoms, $C_1$-$C_4$-alkoxy-C(O)—, benzyloxy-C(O)—$C_1$-$C_4$-alkoxy-$C_1$-$C_4$-alkyl-C(O)—, —SO$_2$—$C_1$-$C_4$-alkyl, and —SO$_2$—$C_1$-$C_4$-halogenoalkyl having 1 to 5 halogen atoms;

phenyl-$C_1$-$C_4$-alkyl, optionally substituted by 1, 2, 3, 4 or 5 substituents independently selected from the group consisting of halogen, —OH, —NO$_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —SO$_2$—$C_1$-$C_4$-halogenoalkyl having 1 to 5 halogen atoms; and heterocyclyl-$C_1$-$C_4$-alkyl, wherein the heterocyclyl substituent of the heterocyclyl-$C_1$-$C_4$-alkyl is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^2$ is selected from the group consisting of
hydrogen, halogen, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$;
—$NR^{12}R^{13}$;
—$OR^{14}$;
—$SR^{15}$, —S(O)$R^{15}$, —$SO_2R^{15}$;
$C_1$-$C_6$-alkyl, $C_3$-$C_6$-cycloalkyl, $C_2$-$C_4$-alkenyl, $C_3$-$C_6$-cycloalkenyl, $C_2$-$C_4$-alkynyl, phenyl-$C_1$-$C_4$-alkyl, each of which is optionally substituted by 1, 2, 3, 4 or 5 substituents independently selected from the group consisting of halogen, —OH, —$NO_2$, cyano, $C_1$-$C_4$-alkyl-C(O)—, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, —$NH_2$, —NH($C_1$-$C_4$-alkyl), —N($C_1$-$C_4$-alkyl)$_1$, —NH(C(O)—$C_1$-$C_4$-alkyl), —N($C_1$-$C_4$-alkyl)(C(O)—$C_1$-$C_4$-alkyl), —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;
heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO-$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;
phenyl which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_1$-$C_6$-cycloalkyl, —$NH_2$, —NH($C_1$-$C_4$-alkyl), -N($C_1$-$C_4$-alkyl)$_2$, —S-$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, heterospirocycloalkyl, 5-membered heteroaryl and 6-membered heteroaryl, each of which is optionally substituted by 1, 2, 3 or 4 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl), $C_1$-$C_4$-alkyl, $C_1$-$C_4$-alkyl-C(O)—, $C_1$-$C_4$-halogenoalkyl having 1 to 5 halogen atoms, $C_1$-$C_4$-alkoxy, hydroxy-$C_1$-$C_4$-alkyl, $C_1$-$C_4$-alkoxy-$C_1$-$C_4$-alkyl-, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms, and 4- to 10-membered heterocycloalkyl, $R^3$ is hydrogen or $C_1$-$C_4$-alkyl, $R^4$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-halogenoalkoxy having 1 to 5 halogen atoms, $C_1$-$C_4$-alkyl—C(O)—, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, and —$SO_2$—$C_1$-$C_4$-alkyl, optionally hydrogen and halen, optionally fluorine and chlorine;

$R^5$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-halogenoalkoxy having 1 to 5 halogen atoms, $C_1$-$C_4$-alkyl—C(O)—, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, and —$SO_2$—$C_1$-$C_4$-alkyl, $R^6$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-halogenoalkoxy having 1 to 5 halogen atoms, $C_1$-$C_4$-alkyl—C(O)—, —$NH_2$, —NH(C)-$C_4$-alkyl), —N($C_1$-$C_4$-alkyl)$_2$, —S—$C_1$-$C_4$-alkyl, —S(O)—$C_1$-$C_4$-alkyl, and —$SO_2$—$C_1$-$C_4$-alkyl, $R^7$ is selected from the group consisting of hydrogen, —OH, fluorine, $C_1$-$C_4$-alkyl and $C_1$-$C_4$-alkoxy, $R^8$ is selected from the group consisting of hydrogen, —OH, fluorine, $C_1$-$C_4$-alkyl and $C_1$-$C_4$-alkoxy, or $R^7$ and $R^8$ together form an oxo group (=O), or $R^7$ and $R^8$ form, together with the carbon atom to which they are attached, a 3- to 6-membered ring selected from the group consisting of $C_3$-$C_6$-cycloalkyl and 3- to 6-membered heterocycloalkyl, $R^9$ is selected from the group consisting of hydrogen, $C_1$-$C_4$-alkyl, $C_1$-$C_4$-halogenoalkyl having 1 to 5 halogen atoms and $C_1$-$C_4$-alkoxy, $R^{10}$ is selected from the group consisting of hydrogen, —OH, $C_1$-$C_4$-alkyl and $C_1$-$C_4$-alkoxy, $R^{11}$ is selected from the group consisting of hydrogen, $C_1$-$C_4$-alkyl and $C_1$-$C_4$-alkoxy, or $R^{10}$ and $R^{11}$ form, together with the carbon atom to which they are attached, a 3- to 6-membered ring selected from the group consisting of $C_3$-$C_6$-cycloalkyl and 3- to 6-membered heterocycloalkyl, $R^{12}$ and $R^{13}$ are independently selected from the group consisting of hydrogen, —OH, —$NH_2$, —NH($C_1$-$C_4$-alkyl), —N($C_1$-$C_4$-alkyl)$_2$, —NH(—C(O)—$C_1$-$C_4$-alkyl), —N($C_1$-$C_4$-alkyl)(—C(O)—$C_1$-$C_4$-alkyl), $C_1$-$C_4$-alkoxy, $C_1$-$C_4$-alkoxy-C(O)—;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, —NH—C(O)—$C_1$-$C_4$-alkyl, —N($C_1$-$C_4$-alkyl)(—C(O)—$C_1$-$C_4$-alkyl), $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —SO=$C_1$-$C_4$-halogenoalkyl having 1 to 5 halogen atoms and ($C_1$-$C_4$-alkoxy)$_2$P(=O)—;

heterocyclyl-$C_1$-$C_4$-alkyl, wherein the heterocyclyl substituent of the heterocyclyl-$C_1$-$C_4$-alkyl is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl), $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, benzo-$C_1$-$C_4$-cycloalkyl, each of which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, Ca-Cr-cycloalkyl, —$NH_2$, —NH(C)-$C_4$-alkyl), ~N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —SO—$C_1$-$C_4$-halogenoalkyl having 1 to 5 halogen atoms; and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^{14}$ is selected from the group consisting of
—$NH_2$, —NH($C_1$-$C_4$-alkyl), —N($C_1$-$C_4$-alkyl)$_2$;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, ~C(O)—$NH_2$, —C(O)—NH($C_1$-$C_4$-alkyl), —C(O)—N($C_1$-$C_4$-alkyl), $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_5$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substitutent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_3$-cycloalkyl, —$NH_2$, —NH($C_1$-$C_4$-alkyl), —N($C_1$-$C_4$-alkyl)$_2$, —S-$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH(C)-$C_4$-alkyl), —C(O)—N(C)-$C_4$-alkyl)$_1$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_1$-$C_6$- cycloalkyl, —$NH_2$, —$NH(C_1-C_4$-alkyl), —$N(C_1-C_4$alkyl$)_2$, —S—$C_1-C_4$-alkyl, —S(O)—$C_1-C_4$alkyl, —$SO_2$—$C_1-C_4$-alkyl, —S—$C_1-C_4$-halogenoalkyl having 1 to 5 halogen atoms, —S(O)—$C_1-C_4$-halogenoalkyl having 1 to 5 halogen atoms and —$SO_2$—$C_1-C_4$-halogenoalkyl having 1 to 5 halogen atoms, $R^{15}$ is selected from the group consisting of hydrogen;

$C_1-C_4$-alkyl, $C_3-C_6$-cycloalkyl, phenyl-$C_1-C_4$-alkyl, each of which is optionally substituted by 1, 2 or 3 substituents independently selected from the group consisting of halogen, —OH, cyano, —COOH, $C_1-C_4$-alkoxy-C(O)—, —C(O)—$NH_2$, —C(O)—NH($C_1-C_4$-alkyl), —C(O)—N($C_1-C_4$-alkyl$)_2$, $C_1-C_4$-alkyl, $C_1-C_4$-halogenoalkyl having 1 to 5 halogen atoms, $C_1-C_4$-alkoxy, $C_1-C_4$-halogenoalkoxy having 1 to 5 halogen atoms, $C_3-C_6$-cycloalkyl, —$NH_2$, —$NH(C_1-C_4$-alkyl), —$N(C_1-C_4$-alkyl$)_2$, —S—$C_1-C_4$-alkyl, —S(O)—$C_1-C_4$-alkyl, —$SO_2$—$C_1-C_4$-alkyl, —S—$C_1-C_4$-halogenoalkyl having 1 to 5 halogen atoms, —S(O)—$C_1-C_4$-halogenoalkyl having 1 to 5 halogen atoms and —$SO_2$—$C_1-C_4$-halogenoalkyl having 1 to 5 halogen atoms;

heterocyclyl-$C_1-C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1-C_4$-alkoxy-C(O)—, —C(O)—$NH_2$, —C(O)—NH($C_1-C_4$-alkyl), —C(O)—N($C_1-C_4$-alkyl$)_2$, $C_1-C_4$-alkyl, $C_1-C_4$-halogenoalkyl having 1 to 5 halogen atoms, $C_1-C_4$-alkoxy, hydroxy-$C_1-C_4$-alkyl, $C_1-C_4$-halogenoalkoxy having 1 to 5 halogen atoms, $C_3-C_6$-cycloalkyl, —$NH_2$, —$NH(C_1-C_4$-alkyl), —$N(C_1-C_4$-alkyl$)_2$, —S—$C_1-C_4$-alkyl, —S(O)—$C_1-C_4$-alkyl, $SO_2$—$C_1-C_4$-alkyl, —S—$C_1-C_4$-halogenoalkyl having 1 to 5 halogen atoms, —S(O)—$C_1-C_4$-halogenoalkyl having 1 to 5 halogen atoms and —$SO_2$—$C_1-C_4$-halogenoalkyl having 1 to 5 halogen atoms;

phenyl, which is optionally substituted by 1, 2 or 3 substituents independently selected from the group consisting of halogen, cyano, nitro, —OH, $C_1-C_4$-alkyl, $C_1-C_4$-halogenoalkyl having 1 to 5 halogen atoms, $C_1-C_4$-alkoxy, $C_1-C_4$-halogenoalkoxy having 1 to 5 halogen atoms, $C_3-C_6$-cycloalkyl, —$NH_2$, —$NH(C_1-C_4$-alkyl), —$N(C_1-C_4$-alkyl$)_2$, —S—$C_1-C_4$-alkyl, —S(O)—$C_1-C_4$-alkyl, —$SO_2$—$C_1-C_4$-alkyl, —S—$C_1-C_4$-halogenoalkyl having 1 to 5 halogen atoms, —S(O)—$C_1-C_4$-halogenoalkyl having 1 to 5 halogen atoms and —$SO_2$—$C_1-C_4$-halogenoalkyl having 1 to 5 halogen atoms; and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1-C_4$-alkoxy-C(O)—, —C(O)—$NH_2$—C(O)—NH($C_1-C_4$-alkyl), —C(O)—N($C_1-C_4$-alkyl$)_2$, $C_1-C_4$-alkyl, $C_1-C_4$-halogenoalkyl having 1 to 5 halogen atoms, $C_1-C_4$-alkoxy, hydroxy-$C_1-C_4$-alkyl, $C_1-C_4$-halogenoalkoxy having 1 to 5 halogen atoms, $C_3-C_6$-cycloalkyl, —$NH_2$, —$NH(C_1-C_4$-alkyl), —$N(C_1-C_4$-alkyl$)_2$, —S—$C_1-C_4$-alkyl, —S(O)—$C_1-C_4$-alkyl, —$SO_2$—$C_1-C_4$-alkyl, —S—$C_1-C_4$-halogenoalkyl having 1 to 5 halogen atoms, —S(O)—$C_1-C_4$-halogenoalkyl having 1 to 5 halogen atoms and —$SO_2$—$C_1-C_4$-halogenoalkyl having 1 to 5 halogen atoms, wherein when Y is O, S or N-$R^9$, none of $R^7$, $R^8$, $R^{10}$ and $R^{11}$ is —OH or $C_1-C_4$-alkoxy, and wherein when X is O, S or N—$R^9$, none of $R^7$ and $R^8$ is —OH or $C_1-C_4$-alkoxy;

and

Hal is halogen, or a stereoisomer, tautomer, N-oxide, hydrate, solvate, or salt thereof, or a mixture thereof.

13. A pharmaceutical composition comprising the compound of formula (I) of claim 1 or a stereoisomer, tautomer, N-oxide, hydrate, solvate, or salt thereof, or a mixture thereof and one or more pharmaceutically acceptable excipients.

14. A method for the control or treatment of a helminthic infection comprising administering an effective amount of the compound of formula (I) claim 1 to a subject in need thereof.

15. A method for the control or treatment of a helminthic infection comprising administering an effective amount of the pharmaceutical composition of claim 13.

* * * * *